US007529718B2

(12) United States Patent
Lambert

(10) Patent No.: US 7,529,718 B2
(45) Date of Patent: May 5, 2009

(54) FAST COMPUTER DATA SEGMENTING TECHNIQUES

(76) Inventor: Christophe Gerard Lambert, 716 S. 20th Ave., Suite 102, Bozeman, MT (US) 59718

( * ) Notice: Subject to any disclaimer, the term of this patent is extended or adjusted under 35 U.S.C. 154(b) by 233 days.

(21) Appl. No.: 10/367,053

(22) Filed: Feb. 14, 2003

(65) Prior Publication Data
US 2003/0149554 A1 Aug. 7, 2003

Related U.S. Application Data

(63) Continuation-in-part of application No. PCT/US01/25519, filed on Aug. 14, 2001.

(60) Provisional application No. 60/358,631, filed on Feb. 20, 2002, provisional application No. 60/255,113, filed on Aug. 14, 2000.

(51) Int. Cl.
*G06F 15/18* (2006.01)
(52) U.S. Cl. .................. 706/20; 706/12; 706/45
(58) Field of Classification Search ............ 706/20
See application file for complete search history.

(56) References Cited

U.S. PATENT DOCUMENTS

| 6,434,542 | B1 | 8/2002 | Farmen et al. | |
| 6,647,508 | B2* | 11/2003 | Zalewski et al. | 714/3 |
| 6,904,423 | B1* | 6/2005 | Nicolaou et al. | 706/46 |
| 2002/0016892 | A1* | 2/2002 | Zalewski et al. | 711/153 |
| 2002/0032850 | A1* | 3/2002 | Kauffman | 712/31 |
| 2003/0061186 | A1* | 3/2003 | Farmen et al. | 706/20 |

FOREIGN PATENT DOCUMENTS

| EP | 0938055 A2 | 8/1999 |
| EP | 1149346 | 10/2001 |
| WO | PCT/US98/07899 | 10/1998 |
| WO | PCT/US99/25922 | 5/2000 |

OTHER PUBLICATIONS

S.S. Young; D.M. Hawkins ("Using Recurisve Partitioning to Analyze a Large Sar Data Set" SAR andQSAR in Environmental Research, vol. 8, Issue 3 & 4, Jan. 1998).*
JSM 2000 Exhibitors p. 1-3.*
Hawkins; On the choice of Segments in Piecewise Approximation; J. Inst. Maths Applic. (1972) 9, 250-256.
Hawkins and Merriam; Optimal Zonation of Digitized Sequential Data; Mathematical Geology, vol. 5, No. 4, 1973, pp. 389-394.

(Continued)

*Primary Examiner*—David R Vincent
*Assistant Examiner*—Lut Wong
(74) *Attorney, Agent, or Firm*—Robert McGinnis

(57) ABSTRACT

Versions of the invention are directed to computer-based methods, apparatus and software (programs) for fast, dynamic programming and recursive partitioning techniques to segment data, especially real-world data, into data structures for display as nodal trees. These techniques and displayed data in segmented form have numerous applications, especially for the analysis and understanding of real-world data. Some particular applications are in the area of computational high throughput screening of molecular drug (or pharmaceutical) candidates using a quantitative structure activity relationship (QSAR) approach. Another particular application is in the areas of pharmacogenomics and pharmacogenetics.

47 Claims, 5 Drawing Sheets

OTHER PUBLICATIONS

Hawkins and Merriam; Zonation of Muttivariate Sequences of Digitized Geologic Data; Mathematical Geology, vol. 6, No. 3, 1974 pp. 263-269.

Hawkins; Point Estimation of the Parameters of Piecewise Regression Models; Appl. Statist. (1976), 25, No. i, pp. 51-56.

Hawkins, et. al.; Zonation of Sequences of Heteroscedastic Multivariate Data; Computers & Geosciences; vol. 5, pp. 189-194.

Hawkins and Kass; "Automatic Interaction Detection" in Topics in Applied Multivariate Analysis, ed. D.M. Hawkins, Cambridge Univ. Press (1982), pp. 269-302.

Hawkins, et. al.; Analysis of a Large Structure-Activity Data Set Using Recursive Partitioning; Quant. Struct.-Act. Relat. 16; 296-302 (1997).

Chen, et. al.; Recursive Partitioning Analysis of a Large Structure Activity Data Set Using Three Dimensional Descriptors; J. Chem Inf. Comput. Sci., 1998, 38, pp. 1054-1062.

Chen, et. al.; Automated Pharmacophore Indentification for Large Chemical Data Sets; J. Chem. Inf. Comput. Sci., 1999, 39—pp. 887-896.

Rusinko, et. al.; Analysis of a Large Structure/Biological Activity Data Set Using Recursive Partitioning; J. Chem. Inf. Comput. Sci., 1999; 39, pp. 1017-1026.

Hawkins; Firm (manual) release 2.2, (1999) pp. 1-68, Dept. of Applied Statistics, Univ. of Minnesota, 352 COB, 1994 Buford Ave.; St. Paul, MN 55108 (downloaded off internet).

Musser; Extensions To Recursive Partitioning; PhD Thesis Dept. Appl. Statistics, Univ. of Minnesota, St. Paul, MN 55108.

Young, et. al.; Mixture Deconvolution and analysis of Ames Mutagenecity data, Chemometrics and Intelligent Laboratory Systems, 60, (2002) pp. 5-11.

Young, et. al.; So many targets, so many compounds, but so few resources; Current Drug Discovery, Dec. 2002 pp. 17-22.

Lambert; Compound Selection & Pharmacogenetics Tools; Genetic Engineering News, vol. 23, No. 1, Jan. 1, 2003 pp. 30-32.

Lambert, et. al.; Data Mining Interactions of Disease and Drug Response with Multiple Genes and Environmental Factors; Abstract of poster session; Midwest Biopharmaceutical Statistics Workshop; Muncie, Indiana, May 25, 1999; p. 29.

Unknown Author; Analysis of Genomic Data in Drug Discovery; Candidate Gene Analysis; Abstract 1999 Joint Statistical Meeting of the ASA; Baltimore, Md.; Aug. 12, 1999, p. 9.

Are you still taking a "brute force" approach to High Through-put Screening, Golden Helix Sales brochure, (distributed Aug. 14, 2000 for first time at ASA meeting Indianapolis, Indiana).

Is your company taking full advantage of the revolution in pharmacogenomics, Golden Helix Sales brochure, (distributed Aug. 14, 2000 for first time at ASA meeting Indianapolis, Indiana).

Helix tree Features, Golden Helix Sales flyer, Jun. 4, 2001 (4 pages).

Chem tree Features, Golden Helix sales flyer, latter half 2002, (4 pages).

* cited by examiner

FAST COMPUTER DATA SEGMENTING TECHNIQUES

The present patent application claims priority from U.S. provisional patent application 60/225,113, filed 14 Aug. 2000 and all of the contents 60/225,113 are incorporated herein by reference and to the fullest extent of the law. The present application is a CIP of PCT/US01/25519 (having the same title) filed 14 Aug. 2001 and PCT/US01/25519 is incorporated herein by reference in its entirety and to the fullest extent of the law. The present application claims priority from U.S. provisional patent application 60/358,631 filed 20 Feb. 2002 and all of the contents 60/358,631 are incorporated herein by reference and to the fullest extent of the law.

TECHNICAL FIELD

Versions of the invention are in the field of computer-based methods and techniques for segmenting data into homogeneous segments (similar subgroups). Such data includes for example, real-world data that represents real-world objects and phenomena. Applications in numerous fields exist (for example, see below). Versions of the invention are generally in areas that are often referred to as recursive partitioning, data mining, data processing or cluster analysis.

Some versions are specifically in the areas of computational chemistry, pharmaceutical high throughput screening and genetics. Some such versions of the invention segment molecules such as drug candidate molecules into homogeneous segments, wherein each homogeneous segment is essentially a subgroup of drug candidates having a similar property and similar characteristics (or descriptor values). Some versions of the invention display data in segmented form (on a monitor or equivalent device) for practical use by a human operator. One such practical use is for research and development purposes in the pharmaceutical industry. Some versions of the invention display data in segmented form for purposes of research and development.

BACKGROUND

Computer-Based Segmenting Algorithms

The use of computer-based segmenting algorithms to segment a group of sequential data into like parts (similar subgroups) is a known technique.[I] Such segmenting algorithms collect data values into similar subgroups, wherein each subgroup corresponds or belongs to a segment. These algorithms and methods essentially "segment" the data, so that data (or data values) within each segment are essentially homogeneous (see FIG. 5 in the Appendix as an example). And a measure of the homogeneity of the data in each segment is frequently calculated. And an overall (for all the segments combined) measure of the homogeneity of the data (or data values) in each segment is frequently calculated. An important advantage of these segmenting algorithms is for correlation purposes. (Ref 1 endnotes, page 390)

[I] Hawkins D M, Merriam D F, Optimal Zonation of Digitized Sequential Data. Mathematical Geology, vol 5, No. 4, 1973, pp. 389-394.

Data or data points in such a segmented form is often easier to work with and easier to understand. For this reason computer-based processes that "segment" such data, as well as data in segmented form have great utility. Applications of such data segmenting processes, as well as data in segmented form occur in a multitude of fields. Even in the field of geology there are many such applications to geological data, these include mechanical logs of bore holes, x-ray data, seismic traces, magnetic profiles, and land-resource observations made along transects. (see reference 1 endnotes, p. 390).

A dynamic programming (DP) segmenting algorithm was developed by Hawkins. This Hawkins DP algorithm finds one or more essentially optimal data segmentations or "coverings" by essentially calculating an overall measure of segment homogeneity for each possible segmentation (or covering).[II] One or more coverings with the optimal value of overall homogeneity are then selected by the algorithm. This DP algorithm was an improvement, in terms of running time, over non-DP approaches. (see Reference 1, pp. 390-391 and Description section for more details)

[II] In this patent application, the terms "segmentation", "covering" and "split" are equivalent or essentially equivalent.

Recursive Segmenting, Methods of Recursive Partitioning

Segmenting techniques have continued to evolve. For example, one or more segmenting algorithms have frequently been used to segment data recursively (or repeatedly). Such recursive techniques result in a recursive partitioning (RP) of data into subgroups. One known computer-based scheme that uses a combination of segmenting algorithms and RP techniques is FIRM. FIRM stands for Formal Inference-based Recursive Modeling. FIRM was developed by Professor Hawkins and is publicly available (see Description section for more details).

Conventional Segmenting Techniques Limited by Long Computer Running Times

Despite continued evolution of segmenting techniques, these techniques continue to have a major limitation. This major limitation of conventional segmenting algorithms is that they frequently work slowly with large amounts of data or large numbers of data points. The Hawkins DP algorithm also has this limitation.

The long running times of conventional segmenting algorithms are a significant problem for many potential applied fields of usage of segmenting techniques. This significant problem exists in the area of computational chemistry, high-throughput screening of pharmaceuticals and genetics analysis, where the amount of data to be segmented is enormous.

The Great Need for Better High Throughput Screening of Pharmaceuticals

A veritable explosion in the number of compounds available as potential pharmaceuticals has recently taken place. Large numbers of different types of compounds are being physically tested for biological, medical and pharmaceutical properties. And a vast amount of information or data on both tested and untested compounds is being accumulated. Such data is being stored in large chemical libraries. Such libraries have both general and specific (focused) data on chemical compounds that are potential pharmaceuticals.

In addition, the number of potential pharmaceuticals will be greatly increased by the Human Genome Project. This project will identify numerous new "drug targets". These targets are places at the molecular level for a drug to act or exert its effect. Such an increase in drug targets will also greatly increase the number of potential pharmaceutical compounds.

Research and development to find new and useful pharmaceuticals has usually required sifting through large numbers of candidate compounds in order to find promising candidates. One method of screening candidate compounds is to physically test the candidate compounds. In it's simplest form, screening by physical testing is essentially "trial and error" and requires testing essentially every candidate. Even more sophisticated physical testing procedures require a great deal of effort, time and expense.

Current methods of screening large numbers of candidates are known as high throughput screening (HTS). Significant advances in the technology for the testing of compounds for desirable pharmaceutical properties have occurred, yet HTS still has great deficiencies.

Current HTS techniques simply cannot screen the number of newly available potential candidate pharmaceuticals. Limitations in current HTS methods cause delays in bringing drugs to market, resulting in great losses in potential profits. And many large-scale high throughput screening attempts still fail to identify a good lead compound (prototype drug molecule) to stimulate further research.

Computer-Based Methods of Screening Pharmaceutical Candidates have the Potential to Save Expense, Time and Work in High Throughput Screening.

Computer-based methods of screening molecules (or compounds) are methods of reducing the workload, time and expense of screening by physical testing. Such computational approaches attempt to identify promising candidate compounds (or molecules) with desirable pharmaceutical properties.

For example, a certain group of compounds may be known to possess a desirable pharmaceutical property. A computer or human judgment then identifies molecular or chemical characteristics of the compounds in this group. A computer-based identification of other compounds that have the same (or similar) molecular characteristics is then done to form a new group of promising candidate pharmaceutical compounds. The candidate compounds (or molecules) in this new group has an increased probability of possessing the desired property, despite having not been actually physically tested.

Thus, a promising new group of candidate pharmaceuticals has been identified without the actual physical testing of the compounds in the group. And much work, time and expense have been saved. The compounds in the group can then be subjected to further investigation.

Computational HTS Using QSAR

Most important computational screening approaches are based on the idea that a particular pharmaceutical property of a compound is due to the compound's molecular structure. In effect these approaches assume that the property is due to the compound's shape at the molecular level. Such "quantitative structure-activity relationship" or QSAR approaches attempt to characterize the parts of a molecule's shape that contribute to the pharmaceutical property or "activity". Such important molecular parts (pieces of a molecule) are sometimes referred to as pharmacophores. Just as keys fit into a lock, molecular parts such as pharmacophores of the right shape cause their effects by fitting into other "target molecules" in the human body. (These target molecules are sometimes called receptors.) In effect, QSAR approaches are similar to looking for "molecular puzzle pieces"—pharmacophores or molecular parts having about the same molecular shape or characteristics.

Most Computational HTS Methods Using QSAR Approaches are too Idealized to Handle Real-World Situations Most computational QSAR approaches use idealized mathematical and statistical models. However, these idealized models are too simplistic to accommodate the complexities of real world molecular structure and the structure-activity relationship between a drug and it's target. Real world molecular structures (and QSARs) exhibit complexities that are not idealized. Therefore there is a great need for more realistic methods of computational high throughput screening using QSAR approaches.

Methods of Recursive Partitioning are Realistic and Can Deal with Realities of Computational HTS Methods of recursive partitioning (RP) can deal with realities of computational HTS, including those of computation HTS methods that use QSAR approaches. Methods of RP are able, for example, to handle realities such as interaction effects, threshold effects and nonlinearities. This realization has spawned the development of new methods of RP in high throughput screening.

Some Recent Methods of RP in Computational HTS

One such recent method uses RP techniques to separate drug candidates into subgroups (or nodes of a tree), wherein drugs in nodes are similar in terms of number of specific molecular fragments and potency.[III] A second RP method generates binary trees, wherein each node is split into two daughter nodes. In this method drugs are grouped into nodes, wherein drugs in nodes are similar in terms biological activity and only one of the two categories of (1) presence or (2) absence of specific chemical descriptors.[IV]

[III] Hawkins, et. al. Analysis of Large Structure-Activity Data Set Using Recursive Partitioning. Quant. Struct.—Act.Relat. 16, 296-302 (1997).
[IV] Published PCT patent application PCT/US98/07899, publication date Oct. 22, 1998.

Even New RP Methods of HTS (Including those that Use QSAR Approaches) are often Essentially Limited to Binary Splitting or Small Data Sets.

A third RP method uses chemical or molecular descriptors that are generated from 2D topological representations of molecular structures. Such descriptors include atom pairs separated by minimal topological distance, topological torsions and atom triples employing shortest path lengths between atoms in a triple. This third method while using distance and topological type descriptors also generates only binary trees. Thus the method is also essentially limited to a presence or absence type of categorization (or splitting). This reference indicates that segmenting into more than two daughter nodes using techniques such as FIRM is essentially limited to working with small amounts of data, because of increases in computer run time.[V] This reference essentially indicates that viable general RP packages for HTS are limited-to small data sets. See also related U.S. Pat. No. 6,434,542.

[V] Rusinko, et. al., Analysis of a Large Structure/Biological Activity Data Set Using Recursive Partitioning. J. Chem. Inf. Comput. Sci. 1999, 39, 1017-1026. "In contrast to data partitioning via continuous variables, binary classification trees can be computed very quickly and efficiently since there are far fewer and much simpler calculations involved. For example, FIRM develops rules for splitting based on "binning" of continuous variables and amalgamating contiguous groups. These procedures add considerably to execution time and hence limit the interactive nature of most general recursive partitioning packages to data sets much smaller than those under consideration. With binary data, on the other hand, a parent node can only be split into two and only two daughter nodes." (p. 1019)

There is a Great, Unmet need for Faster Computational HTS-QSAR, RP Techniques Employing Multi-Way Splitting Using Geometry-Based Molecular Descriptors.

Binary splitting is essentially a two category, (1) presence or (2) absence type approach. Such binary splitting cannot take full advantage of the dimensional measurement information present in continuous variables or descriptors such as distance type descriptors.

By contrast, multi-way splitting (or categorization) is generally more versatile than mere binary splitting. Like an ordinary ruler, multi-way splitting divides quantities such as distances into gradated segments based on number measurement. If such multi-way splitting could be done using geometry-based molecular descriptors (such as molecular descriptors based on distances between parts of a molecule), there would be a fuller and more natural use of the actual dimensional measurement information present in geometry-based molecular descriptors. Molecules could then be sorted into segments wherein the molecules in each segment have about the same actual geometric measurements of like molecular parts.

However, this great need of multi-way segmenting using geometry-based descriptors has remained unfulfilled. This is because conventional HTS-QSAR, RP techniques with distance type descriptors are essentially only viable with binary splitting. These conventional techniques, which use conventional segmenting algorithms, are too slow to do multi-way splitting.

Fast Segmenting Algorithms make Possible Computational HTS-QSAR Approaches that Employ Multi-Way Splitting RP Techniques with Geometry-Based Molecular Descriptors.

The inventor's novel Fast Segmenting Algorithms make multi-way splitting using geometry-based molecular descriptors a reality by greatly increasing speed and decreasing computer run times. These Fast Segmenting Algorithms (FSAs) lead to inventions that fulfill the great unmet need.

Versions of the Invention Fulfill the Great Need of True Segmenting Using Geometry-Based Descriptors in Computational HTS Versions of the present invention are computer-based methods that perform multi-way segmenting on molecules (such as drug candidates) using geometry-based molecular descriptors. These computer-based methods use, or have the potential to use, one or more fast segmenting algorithms to perform their segmenting. Versions of the invention are viable RP software packages for multi-way segmenting of large data sets of drug candidates and the candidates' geometry-based molecular descriptors. These software packages are fast enough to allow a researcher to interact meaningfully with a package program during operation. Thus versions of the invention fulfill the great need for a computational RP segmenting method in pharmaceutical HTS that makes full and natural use of the dimensional measurement information present in geometry-based molecular descriptors.

Versions of the Invention Sort Candidate Molecules into Subgroups. The Molecules in Each Subgroup have Molecular Parts with About the Same Geometric Measurements. Pharmacophores Sought by HTS Methods are Important Examples of Such Molecular Parts.

Fast Segmenting Algorithms (FSAs) using geometry-based descriptors sort a group of candidate drug molecules into segments (or subgroups). The molecules in each segment (or subgroup) have molecular parts with about the same geometric measurements. When segmenting using geometry-based descriptors is done repeatedly (or recursively) group molecules are sorted into segments (or subgroups) on the basis of multiple geometric measurements. Such recursive segmenting or partitioning of a group of molecules generates a nodal tree (similar to the tree in FIG. 2). Group molecules are sorted into nodes (or subgroups) so that the molecules in each node have similar molecular parts, these parts have about the same actual geometric measurements. In effect, the nodal tree effectively sorts the molecules, so that molecules in some nodes have a molecular part or parts that are pharmacophores with about the same geometric measurements. This fuller, more natural use of geometric information makes for more powerful methods of finding molecules that are sought by computational HTS-QSAR procedures. In effect HTS-QSAR approaches that employ RP techniques and multi-way splitting with geometry-based descriptors can find (and predict) more exact and better fitting "molecular puzzle pieces" and molecules. These candidate drug molecules with molecular parts or pharmacophores are the "better fitting molecular puzzle pieces" that are the ultimate pursuit of computational HTS-QSAR procedures.

Some Details of the Operation of Versions of Fast Segmenting Algorithms

Conventional segmenting algorithms essentially compute an overall measure of segment homogeneity (sometimes referred to as a score) for all possible segmentations or splits of a data set. Versions of Fast Segmenting Algorithms (FSAS) achieve their increased speed by computing an overall measure of segment homogeneity (or a score value) for only some of the possible splits of a data set. In addition, some versions of FSAs compute a score value for only some select splits. These selected splits have a high probability of being a (or the) split with an optimal score value. FSAs also make use of techniques of dynamic programming such as running sums and updating. Thus versions of FSAs are fast DP algorithms that find one or more splits of a data set, wherein the splits are probable optimal splits.

There is a Multitude of Potential Applied Uses for Fast Segmenting Algorithms and Special Score Functions.

Just as there is a great need for fast segmenting techniques and FSAs in pharmaceutical high throughput screening, these techniques and algorithms have great potential in general chemistry or general computational chemistry. In addition, potential uses of fast segmenting techniques and algorithms are present in a multitude of fields. A few other examples of fields in which real-world data in segmented form has great utility include clinical trials analysis (relating physiological and environmental factors to clinical outcomes, genetics (relating genetic descriptions of organisms to other organism characteristics), geology (finding minerals and oil), modeling nosocomial infections in hospitals, market research (market segmentation), industrial quality improvement (wherein data are frequently "messy" or nonidealized), and demographic studies. (No reference, technique or invention is admitted to being prior art with respect to the present invention by it's mention in this background or summary.) Professor Hawkins has also invented novel measures of segment (or intra-segment) data homogeneity, special score functions (see below).

SUMMARY

The inventor has invented new Fast Segmenting Algorithms. These Fast Segmenting Algorithms are fast computer methods that "split" or "segment" data into segments (or subgroups) so that the data (or data values) within each segment are similar (or homogeneous). Conventional, slower DP segmenting algorithms compute scores for all possible splits. Versions of these new FSAs are fast because they mainly compute a measure of homogeneity (or score) for only select splits using dynamic programming (DP) techniques that speed up the calculations. These select splits have a high chance of being the best, or about the best splits (the most homogeneous splits). One or more of these algorithms used alone, in combination or repeatedly in a recursive partitioning (RP) procedure are versions of a new invention with a multitude of potential applications.

For example in the field of pharmaceutical high throughput screening (HTS), FSAs fulfill a great unmet need. These FSAs lead to new ways of sorting molecules that are possible new (candidate) drugs into subgroups of molecules that have the greatest potential to be new drugs. Just as an ordinary ruler can categorize objects by length, these new sorting methods use multi-way splitting with geometric molecular characteristics to categorize molecules into subgroups. This fuller, more natural use of geometric information makes for fast, practical computer methods that can find (and predict) molecules with molecular parts (or pharmacophores) that have a good, geometric molecular fit—just as keys fit into a lock. In the search for new drugs, these candidate drug molecules and their pharmacophores are the "better fitting molecular puzzle pieces" that are the ultimate pursuit of the pharmaceutical industry's massive high throughput computer screening projects.

By contrast, conventional computer sorting techniques used for high throughput pharmaceutical screening do not make such full use of geometric information. Even conventional techniques that use distance type characteristics of drug candidates are too slow to segment molecules into multiple categories. Instead, these slow conventional techniques use only a (binary) two category, yes-no type of classification scheme.[VI]

[VI] A simple analogy to contrast FSAs and conventional techniques that use distance type descriptors or geometry-based descriptors for pharmaceutical screening is as follows. A computer project is to screen 5,000 people to be one of 10 members of a basketball team. The height, arm length, jump heighth, and running speed down the court of each candidate person is measured. Conventional Techniques Techniques that are analogous to the slow, conventional pharmaceutical screening techniques have only a (binary) two category, yes-no type of classification scheme. These conventional techniques can only sort the candidates into two groups, such as (A1) those 6 feet tall and (A2) those not 6 feet tall, or (B1) those who jump 1 foot and (B2) those who jump a heighth other (higher or lower) than 1 foot, or (C1) those whose arms are 2 feet long and (C2) those whose arms are not 2 feet long, etc. These conventional techniques are too slow to do real segmenting. Fast Segmenting Techniques By contrast techniques that are analogous to FSAs for pharmaceutical screening, can sort the candidates into segments (A1) those 5 to 5.5 feet tall, (A2) those 5.5 to 6 feet tall, (A3) those 6 to 6.5 feet tall and (A4) those over 6.5 feet tall; (B1) those who jump 0.5 to 1 foot, (B2) those who jump 1 to 1.5 feet (B3) those who jump 1.5 to 2 feet (B4) those who jump over 2 feet; (C1) those whose arms are 1.5 to 2 feet (C2) those whose arms are 2 to 2.5 feet long and (C3) those whose arms are over 2.5 feet long; (D1) those whose run time down the court is less than 3.2 seconds, (D2) those whose run time down the court is 3.2 to 3.5 seconds, (D3) those whose run time down the court is 3.5 to 4 seconds (D4) those whose run time down the court is over 4 seconds. Suppose an ideal candidate to play guard (a certain position on the team) is generally (A2) 5.5 to 6 feet tall, (B2) jumps 1 to 1.5 feet, (C2) has arms of length 1.5 to 2 feet and (D1) runs down the court in less than 3.2 seconds. FSA techniques can generate a nodal tree such as FIG. 2 with "an ideal guard node" (or subgroup) that only contains candidates who are in all four segments (A2), (B2), (C2) and (D1). These people are good candidates to be a guard. Suppose there are 100 such good candidates in the node. FSA techniques are fast enough that they allow human interaction, so a researcher could further split the ideal guard node into three more nodes based on weight: (E1), (E2), and (E3). Suppose that generally an ideal guard's weight is in segment (E1), weight less than 175 lbs. Ideal candidates are now in the node that corresponds to the five segments (A2), (B2), (C2), (D1) and (E1). Each of the candidates in this node have the measurements that make a "good fit" for the job of basketball guard. Suppose further that this node contains 50 candidates. The 50 still have to be tested physically by playing basketball. A physical test is especially important in this case, human beings are not molecules. There may even be very good guards who are not in the node. Computers are powerful tools, but not all knowing.

Fast Segmenting Algorithms have practical uses in many fields. Many types of data that displayed in segmented form are easier work with and easier to understand. A few examples of such types of data are fast enough to allow a human user to interact meaningfully with an RP software package that uses FSAs to segment data. Furthermore, these FSAs give rise to inventions that are not just computer programs. These inventions include (but are not limited to) special purpose computers programmed for specific tasks and data structures—computer data in an arranged format.

Special score functions invented by Professor Hawkins also have numerous and similar applications. This background and summary are not necessarily exhaustive.

Patents

Some patent publications which may be useful in understanding versions of the invention are U.S. Pat. Nos. 4,719,571; 5,787,274; 6,182,058; 6,434,542; and publication T998008. U.S. Pat. No. 6,434,542 also deals with recursive partitioning of molecules and individuals. None of these patents or publications is admitted to being prior art by their mention in this background.

BRIEF DESCRIPTION OF DRAWINGS

FIG. 2 is similar to a screenshot. FIG. 2 is typical of the appearance of Nodal Trees displayed by versions of the invention on a monitor.

DESCRIPTION

The use of computer-based segmenting algorithms to segment a group of sequential data into like parts (similar subgroups) is a known technique.[1]

Computer-based segmenting techniques have continued to evolve and become more sophisticated.[2] Because it is a good teaching that is relevant to the application and is open to the public, reference 2 (Musser B J, Extensions to Recursive Partitioning. Doctoral thesis (October 1999) under the supervision of Professor Douglas M. Hawkins, School of Statistics, University of Minnesota, St. Paul, Minn. 55108 USA) is incorporated herein by reference to the fullest extent of the law. This thesis is in the public domain. A copy of the thesis in PDF format on floppy diskette is included with the U.S. provisional patent application 60/225,113 filed 14 Aug. 2000.

Some important teachings of reference 2. Reference 2 teaches the use of segmenting algorithms combined with methods of recursive partitioning.

In reference 2, some types of data are designated predictors (for example X on page 10). There are different types of predictors: for example, monotonic, free, float (pp. 4 and 6). Monotonic predictors are essentially quantitative in nature. Free predictors are essentially nominal in nature. And float predictors are commonly used to represent or accommodate "missing data". Other types of data are designated to be responses (for example Y on page 10). Pairs of predictor and response values are made (for example $(X_{(i)}, Y_{(i)})$ on page 10). Such pairings tend to conceptualize a response to be predicted by, correlated with or caused by a predictor.

As in other segmenting algorithms and methods, those taught in reference 2 (and similar methods) frequently use (1) one or more measures of the homogeneity of data (or data values) within segments, or (2) an overall measure of the homogeneity of data (or data values) within segments for all (or most of) the segments or (3) a combination of (1) and (2) to "segment" data. It is also possible for these methods (and similar methods) to use measures of inter-segment data value inhomogeneity to segment data. Some important measures of homogeneity or inhomogeneity used by these and similar methods are least square type measures, deviance measures and statistical measures. Some of the computer-based segmenting methods taught in reference 2 and similar methods generate data structures such as dendograms, nodal trees and equivalent structures. Such data structures elucidate correlation, prediction or causal type relationships between one or more predictors and a response in many cases. Several examples of nodal trees (or similar data structures) are given in reference 2.

Figure 1:
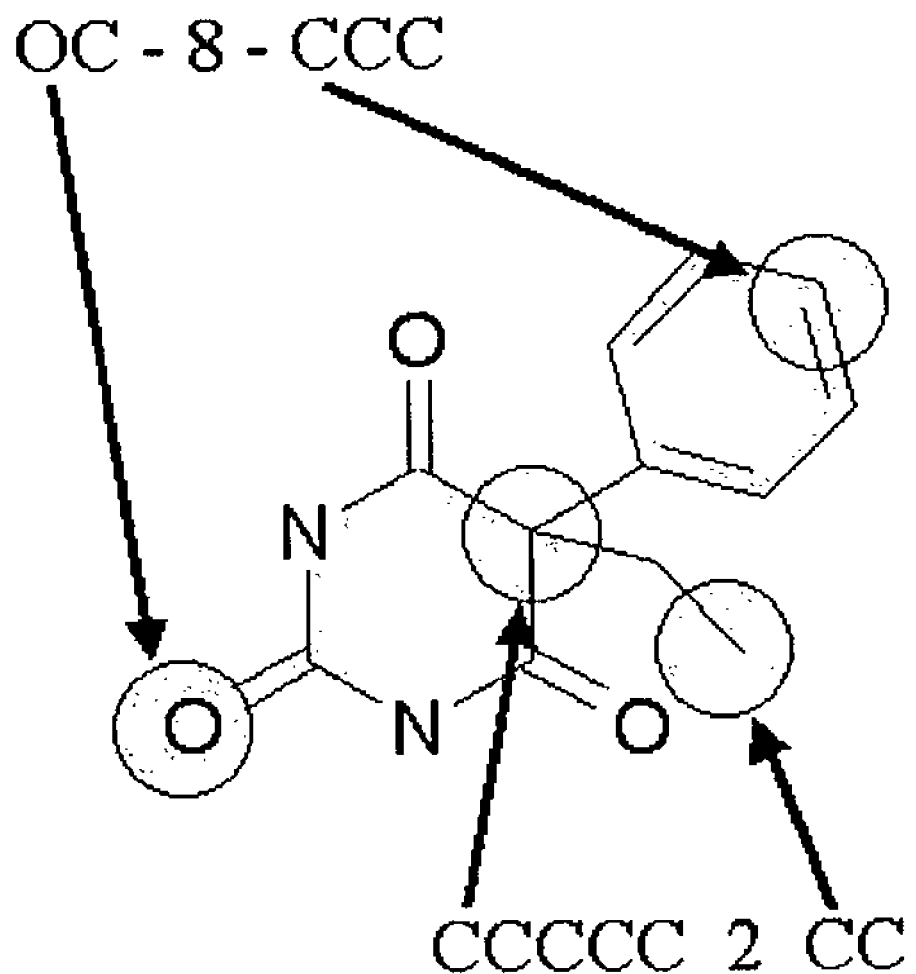
FIG. 1 is an illustration of atom class pairs and geometry-based molecular descriptors.

An example of a method of generating one or more nodes of such a nodal tree or trees is given by a flow chart in reference 2 (FIG. 1.1, page 5). Central to the teachings of reference 2 is the technique of FIRM (Formal Inference-based Recursive Modeling, chapter 1) and similar techniques of Random FIRM (chapter 6) and NextFIRM (chapter 7 and chapter A, including computer code).

Some advantages of Random FIRM are discussed on pages 113 and 114. Random FIRM has the capability of generating a tree or trees by segmenting using a predictor that does not give the best possible segmentation of the data or smallest p-value. Such capability is closely related to segmenting algorithms and methods that are less deterministic and give one or more approximately best segmentations of data. Also important in the teaching of reference 2 are techniques of dynamic programming.

Additional references that are related to those already given and that shed light on aspects of segmenting algorithms and other concepts cited in this application are given in the endnotes. These references are incorporated herein to the fullest extent of the law.[3,4,5,6,7] (No reference of reference 1 through 7 inclusive is admitted to being prior art with respect to the present invention by its discussion or mention in this description.)

The DPSA Appendix contains a more detailed description of DP Segmenting Algorithms[VII] such as the Hawkins DP algorithm and FSAs. As described above and in references 1-9 inclusive (endnotes) and the DPSA Appendix, a segmenting algorithm essentially segments data, so that the Y values (or response values) that correspond to each segment are essentially homogeneous. Each segment is an interval or a grouping of X values (or predictor values). And each Y value (or response value) is associated with an X value (or predictor value). Thus, in a simple usage, a segmenting algorithm segments using one response (variable) Y, and one predictor (variable) X.

[VII] Examples of a DP Segmenting Algorithm are the Hawkins DP Segmenting Algorithm, an FSA, or a Hawkinslike DP Segmenting Algorithm. A Hawkinslike DP Segmenting Algorithm computes an overall score for essentially all (rather than all) possible splits of a data set.

Implementation of such (1) segmenting algorithms, (2) recursive partitioning techniques or (3) a combination of (1) and (2) without undue experimentation is within the capability and understanding of those within the combined arts of computer science and statistics and neighboring arts (including computational methods of high throughput molecular screening or drug screening) after reading this description (including the DPSA Appendix, which describes versions of fast segmenting algorithms) and the references cited above.

For this application, we define a computer-based method or process that uses (1) one or more segmenting algorithms or (2) one or more recursive partitioning methods or procedures or (3) a combination of (1) and (2) as a Segmentation/Recursive Partitioning Process (or abbreviated as an S/RP P); wherein the meaning of segmenting algorithm is any meaning or similar meaning in any one of references 1 through 9 inclusive and the DPSA Appendix. The term "recursive partitioning" is well known in the art of computer science and arts cited above. A discussion of the term is found in the Introduction and early pages of reference 2 and further definition and meaning of the term and it's combination with segmentation techniques is found in reference 2.

For this application, we define a computer-based method or process that uses one or more segmenting algorithms as a segmenting process (or segmentation process), abbreviated as an SP. An SP is an S/RP Process.

Other Examples of S/RP Processes

There are other examples of S/RP Processes and similar processes. There are other versions of FIRM, some examples of other versions of FIRM include CATFIRM and CONFIRM. There are other computer-based methods that are similar to FIRM such as AID, CHAID, DP.CHAID, CART, KnowledgeSEEKER, TREEDISC, and similar techniques.

Helpful in understanding and implementing FIRM is the FIRM manual, Formal Inference-based Recursive Modeling. The latest version is release 2.2, 1999. This manual can be downloaded over the internet. This manual and software can also be ordered from the University of Minnesota bookstore for a nominal charge. The manual and software are incorporated herein by reference to the fullest extent of the law.[8] In addition, concepts useful for understanding and implementing versions of FIRM are described in Chapter 5: Automatic Interaction Detection by Hawkins and Kass pp. 269-302 in the book *Topics in Applied Multivariate Analysis;* Hawkins, D. H., Ed. Cambridge University Press.[9] This chapter is incorporated herein by reference to the fullest extent of the law. (The manual, software, and book chapter are not admitted to being prior art by their mention in this description.)

One or More of the S/RP Processes, or Similar Methods Listed Above, or One or More Similar Processes not Specifically Listed Use One or More Dynamic Programming (DP) Segmenting Algorithms such as the Hawkins DP Segmenting Algorithm, an FSA or Similar Algorithm.

As noted in the Background, Hawkins has developed a DP Segmenting Algorithm (DPSA) for segmenting sequential data (see Reference 1, pp. 390-391 and later in this Description section for more details). One or more S/RP Processes, or similar methods use (or have the potential to use) this Hawkins DP (segmenting) algorithm, or one or more similar DPSAs (such as one or more FSAs) to segment data. As described above, some versions of FIRM accommodate or manipulate data that is "floating" or "free", such as float or free predictors. In some cases, such as some versions of FIRM, an S/RP Process (or similar method) manipulates data into an essentially sequential format wherein such essentially sequential data is segmented by a Hawkins DP algorithm or similar algorithm(s).

Also as noted in the Background, the inventor has invented Fast Segmenting Algorithms (FSAs) that are much faster than the Hawkins DP algorithm (and similar algorithms) especially when segmenting large amounts of data. One or more S/RP Processes, or similar methods use (or have the potential to use) one or more FSAs to segment real-world data.

Any Computer Based Method that Uses an FSA (or wherein the Method has an FSA that is Available for Use) is a Version of the Invention.

Any computer based method (for example an S/RP Process or a similar method) that uses one or more FSAs on any kind of data, including real-world data is a version of the invention. Any computer based method (for example an S/RP Process or a similar method) wherein one or more FSAs is available for use by the method on any kind of data, including real-world data is a version of the invention.

Special Score Functions

The Binomial Score Function Professor Hawkins has also invented a novel measure of segment (or intra-segment) data homogeneity. This new score function is particularly well suited for a univariate response, wherein the response has only two (or essentially only two values). An example of the kind of data for which this new score function is particularly well suited is data wherein the (univariate, two-valued) response value(s) that are essentially associated with each segment (of one or more segments) are essentially distributed according to a binomial distribution. More details on the Binomial Score Function (abbreviated BScore or BScore Function) and homogeneity measures derived therefrom are given in the DPSA Appendix.

Measures of Segment Data Homogeneity and of Overall Segment Data Homogeneity (for a Split) that are Derived from a Binomial Score Function One or more segment homogeneity measures (or score functions) are derived from a Bscore function as described in the DPSA Appendix. One or more overall measures of segment homogeneity (for a split) are derived from a Bscore function as described in the DPSA Appendix. A measure of segment data homogeneity or a measure of overall segment data homogeneity (for a split) that is derived from a Binomial Score Function is an Binomial derived Score Function, abbreviated BdScore or BdScore Function.

Bd-DPSAs

As described in the DPSA Appendix, one or more DPSAs have the potential to use a BScore Function or a BdScore Function as a measure of homogeneity. A DPSA that uses a BScore Function or a BdScore Function is a Bd-DPSA.

Utility of the Pillai Trace Statistic for Segmenting Multi-Variate (Vector) Response Data Professor Hawkins has also discovered a special utility for the Pillai-Trace Statistic in segmenting multi-variate response data. Such data is equivalent to response data in vector form. As described in the DPSA Appendix, one or more DPSAs have the potential to use a score function that is derived from the Pillai-Trace Statistic. A PTd-DPSA is a DPSA that uses a score function that is derived from the Pillai-Trace Statistic.

Special DPSAs An FSA, a Bd-DPSA, PTd-DPSA is a special DP Segmenting Algorithm or a special DPSA.

Any Computer Based Method that uses (or has Available for Use) a Special DPSA (FSA, Bd-DPSA, PTd-DPSA) is a Version of the Invention.

Any computer based method (for example an S/RP Process or a similar method) that uses one or more special DPSAs on any kind of data, including real-world data is a version of the invention. Any computer based method (for example an S/RP Process or a similar method) wherein one or more special DPSAs is available for use by the method on any kind of data, including real-world data is a version of the invention.

Data Objects, Descriptors, Predictors and Responses

From a computational standpoint, a data object is a representation of an object. It is possible for the object that is represented by the data object to be an abstract object or a real-world object. Objects (both abstract and real) have characteristics. From a computational standpoint, a descriptor is a characteristic of an object that is represented by a data object.

Just as a real world object frequently has more than one characteristic, a data object frequently has more than one descriptor. As described in more detail below, each descriptor of a data object has a particular "descriptor value" for each descriptor of the data object.[VIII] Also as described in more detail below, a descriptor is frequently essentially quantitative or qualitative and has quantitative or qualitative values respectively.

Figure 3:
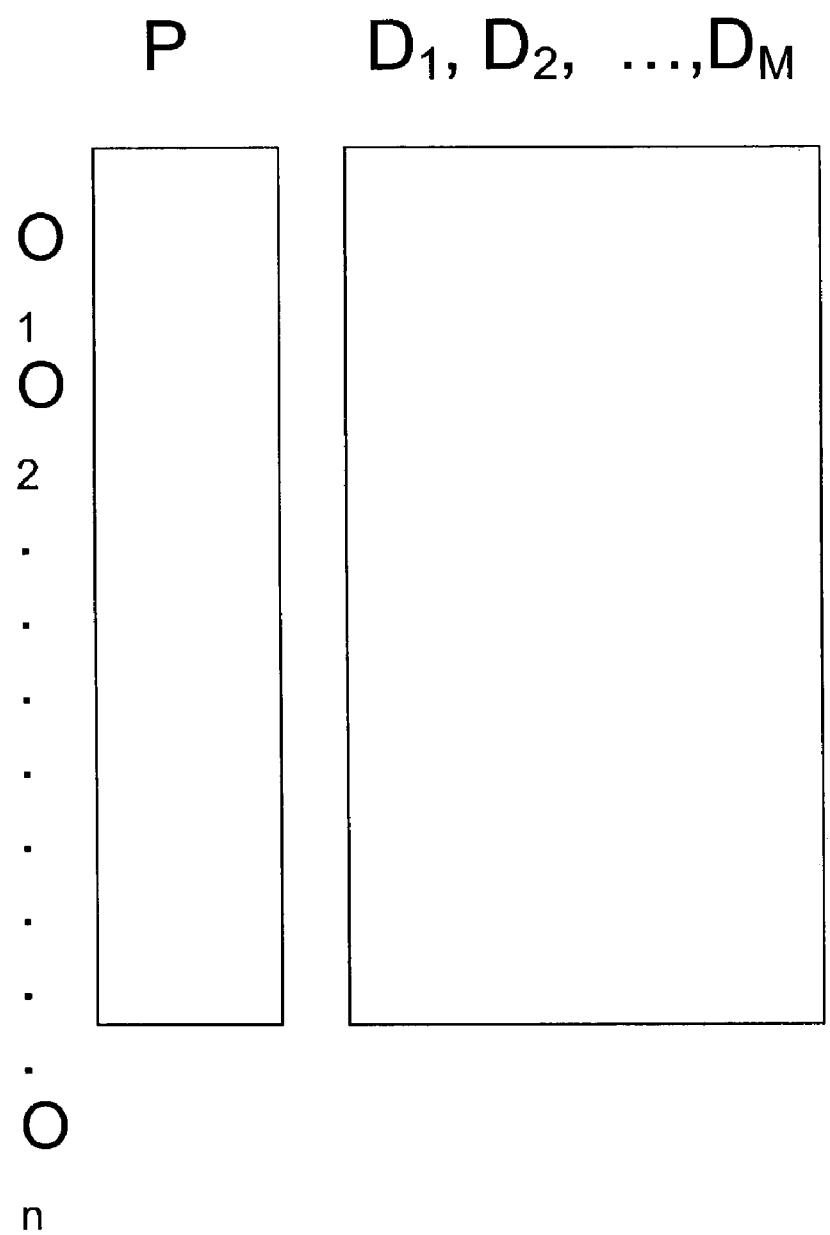
FIG. 3 Data representation for a Group (or Node) of n Data Objects, Matrix Data Representation: There are N data objects in the group (or node) of Data Objects. The data objects are denoted $O_1, O_2, \ldots, O_n$. The property is denoted as P. And the M descriptors are denoted $D_1, D_2, \ldots D_M$. Each row of the matrix corresponds to a data object. The first matrix column corresponds to the property P. And each of the other matrix columns correspond to a descriptor. The value of the property and each descriptor for each data object is recorded in the corresponding matrix cell.

[VIII] FIG. 3 is (or can be conceptualized as) an illustration of such a situation. In such a situation, a descriptor value for each one or more descriptors $D_1$, $D_2$, ..., $D_M$ belongs to each data object (each data object being one of the objects $O_1, ..., O_n$). (response) value corresponds to a descriptor (or predictor) value in that the property (response) value and descriptor (or predictor) value belong to the same data object.

Generally a real-world data object represents a real-world object such as for (nonlimiting) examples, an actual physical object, physical phenomenon, a real-world phenomenon or phenomena, a physical datum or data.

It is possible to conceptualize a first descriptor as being predicted by, correlated with or caused by a second descriptor for a group of data objects. Under such a conceptualization, for example, the first descriptor is designated to be a response and the second descriptor is designated to be a predictor (of the response).[IX] The designation of a first descriptor as a response and a second descriptor as a predictor is somewhat arbitrary. This designation is arbitrary in the sense that it is possible to designate the first descriptor as a predictor and the second descriptor as a response (of the predictor).

[IX] FIG. 3 is (or can be conceptualized as) an illustration of a situation wherein a descriptor P is designated as a response, and each of one or more descriptors $D_1, D_2, ..., D_M$ is designated as a predictor. Under such a conceptualization, each P (response) value corresponds to a descriptor (or predictor) value in that the P (response) value and descriptor (or predictor) value belong to the same data object.

The terms predictor and descriptor are used essentially interchangeably in this patent application. And the reader should be keep in mind the frequent or somewhat arbitrary nature of the distinction between a response and a predictor (or descriptor).

Versions of the Invention Segment Data Objects, wherein the Data Objects Represent Abstract or Real-World Objects Versions of the invention are methods for segmenting data objects using descriptor values, wherein a descriptor is designated a response and one or more descriptors are designated as predictors. The data objects segmented by versions of the invention are abstract or real-world objects.

Illustrative Example of the Versions of the Invention that Handle Real-World Data.

This description will now begin with an illustrative description of versions of the invention that segment a particular kind of real-world data. This real-world data is in the field of high throughput screening of candidate pharmaceuticals. Versions of the invention segment molecules, such as molecules that are drug candidates, using one or more geometry-based molecular descriptors. (For versions of the invention described herein, geometry-based descriptors are essentially equivalent to predictors.) As described in the background, multi-way segmenting of molecular drug candidates using geometry based molecular descriptors has been considered essentially impractical. Thus such multi-way segmenting of molecules (for example drug candidate molecules) using geometry based molecular descriptors is essentially novel and unobvious.

Molecules as Data Objects

Molecules are real world objects. For versions of the invention, a data object is a representation of a real world object. In this application, the term molecular data object means a data object that represents a molecule. Molecules have characteristics. These characteristics are both quantitative and qualitative in nature. Examples of quantitative molecular characteristics are various distances between parts of a molecule or molecules, such as a distance between two atoms in a molecule. An example of a qualitative molecular characteristic is the gross color of a large quantity of the molecule in pure, solid form (such as a powder).

Versions of the invention use segmenting algorithms and recursive partitioning techniques (similar to those described in references 1 through 7 inclusive above) and designate one or more of the characteristics of a group of molecules essentially as predictors; and designate a molecular characteristic of the group of molecules essentially as a response. In this application the molecular characteristic that is designated as the response is referred to as a molecular property. (The terms predictor and response are used essentially as in reference 2.) By doing this, versions of the invention are essentially a method of predicting one or more molecular properties on the basis of one or more molecular characteristics. Alternatively, versions of the invention elucidate correlation or causal type relationships between one or more molecular characteristics and one or more molecular properties. Versions of the invention do this by characterizing molecules as data objects, and molecular properties and characteristics as descriptors or molecular properties.

Descriptors

From a computational standpoint, it is possible to consider a particular molecule as a data object. And it is possible to consider one or more characteristics of a molecule as descriptors of a data object that represents the molecule.

Definition of a descriptor (for versions of the invention): A qualitative or a quantitative characteristic of a data object. A qualitative characteristic is a qualitative descriptor, a quantitative characteristic is a quantitative descriptor. An example of a quantitative descriptor is a person's age, the person being represented by a data object. An example of a qualitative descriptor is the odor of a mushroom, the mushroom being represented by a data object. An example of a quantitative molecular descriptor is a distance between two molecular parts. An example of a qualitative molecular descriptor is the color of a large quantity of the molecule in pure powder form.[x]

[x] The term molecular descriptor includes (but is not limited to) any descriptor of a drug, molecule or molecular substance used in any phase of the pharmaceutical industry. Such phases include research, development, testing, manufacture or usage of a drug or other molecule or molecular substance in the pharmaceutical industry. A molecular descriptor includes any descriptor used in animal, cell line or human studies. Any descriptor of an auxiliary molecule (that is not the, or a principally active compound) such as a molecule that is part of a drug delivery system is an example of a molecular descriptor. Any combination of one or more such molecular descriptors is also a molecular descriptor. Versions of the invention have utility and operability in many areas of chemistry outside the pharmaceutical industry as well. Therefore, for example, any descriptor of a molecular substance used in any phase of the chemical industry is an example of a molecular descriptor. Such phases include (but are not limited to) research, development, testing, manufacture or usage of a molecule in the chemical industry. Any combination of one or more such molecular descriptors is also a molecular descriptor.

Definition of the descriptor value for a data object (for versions of the invention): Each descriptor has a particular value for a particular data object. The value being (1) a quantitative value for a quantitative descriptor or a qualitative value for a qualitative descriptor or (2) the value being "missing" when a quantitative or qualitative value has not been determined. (Note that a quantitative descriptor value is similar or essentially equivalent to a "montonic predictor value" of reference 2. A qualitative descriptor value is similar or essentially equivalent to a "free predictor value" of reference 2. And the concept of a "float predictor value" of reference 2 is similar or equivalent to a descriptor value that is "missing".

An example of a value of a quantitative descriptor for an object is the age "61 years" for a particular person. An example of a value of a qualitative descriptor for an object is the odor "fishy" for a particular mushroom. An example of a value of a qualitative molecular descriptor is the color "white" for a particular molecular substance in pure powder form. An example of a value of a quantitative geometry-based molecular descriptor is the number of angstroms between two atoms of a particular molecule when the molecule is in a particular conformational state.

The use of geometry-based molecular descriptors and S/RP P techniques in versions of the invention is novel and unobvious. Any computer-based method of segmenting two or more molecular data objects using one or more geometry-based molecular descriptors by utilizing one or more S/RP Processes is a version of the invention. These geometry-based molecular descriptors (both qualitative and quantitative) are described in more detail below.

Illustrative Examples of Versions of the Invention. Other examples of quantitative molecular descriptors (predictors) are atom class pairs and various types of "through compound path lengths" between the focal atoms of atom class pairs. This type of descriptor (or predictor) is an example of a geometry-based molecular quantitative descriptor. Example 1 is an illustrative example of a version of the invention that makes use of such descriptors (or predictors). For more details on the particular descriptors used (path length low and high, PLLO and PLHI between atom class pairs) see Example 1.

Some Further Details on Geometry-Based Molecular Descriptors (or Predictors)

In example 1, the molecular features used are atom class pairs, and the focal atoms of each atom class in the pair were the distance measurement endpoints. Each geometry-based descriptor (or predictor) depends on one or more molecular features.

Molecular features include, but are not limited to, atoms, a molecular part or parts, functional groups, surface regions, quantum mechanical representations of a molecular part or parts, field or charge representations of a molecular part or parts, elements of protein, peptide, DNA, RNA, biopolymer, or polymer sequences. For some geometry-based quantitative descriptors, the value of each descriptor is determined by using one or more distance measurement endpoints. Each distance measurement endpoint of a molecular feature is a point on or within a molecular feature. It is possible for any point that is on or within a molecular part to be used as a distance measurement endpoint. A molecular feature separation distance is a distance measurement (or value) between two or more distance measurement endpoints. Examples of molecular feature separation distances include (but are not limited to) distance measurements (or values) between two centroids, nearest distances between two molecular features (or parts), farthest distances between two molecular features (or parts), and the shortest or longest (through space or through compound) connected path length between two or more distance measurement endpoints. A geometry-based quantitative or qualitative descriptor includes (but is not limited to) any descriptor whose descriptor value is determined in whole or in part by one or more molecular feature separation distances.

Examples of molecular feature separation distances include through compound path lengths, which are integer distances in a graph representation of a molecule. Two or three dimensional spatial relationship distances also constitute examples of molecular feature separation distances. Examples of such two and three dimensional spatial relationship distances are the low or the high distance in angstroms between atom class pairs across one or more of multiple conformations of a molecule.

In addition to using distance between measurement endpoint pairs to determine geometry-based molecular descriptor values, a geometry-based descriptor is any descriptor whose value is determined in whole or in part by a geometry-based metric (or measure). An example of such a metric is any metric that is derived from a combination of distances between two or more measurement endpoints. Other examples of such a geometry-based metric include a measure (or value) of any area or volume circumscribed or bounded by two or more distance measurement endpoints of molecular features. Geometry-based metrics include non-Euclidean distance metrics. Geometry-based metrics also include measures of distance that are computed in the dual plane (a concept from computational geometry).

A geometry-based metric includes any mathematical function, calculation, or the equivalent thereof that uses any of the distances or metrics mentioned above singly or in combination. Such mathematical functions or calculations include, but are not limited to, statistical functions. These include such statistical functions as mean, median, mode and other higher order statistical functions or measures. Examples of qualitative geometry-based molecular descriptors (or predictors) are one or more molecular features (or one or more measurement endpoints) that are essentially concave or convex, colinear, planar or coplanar.[XI]

[XI] A geometry-based molecular descriptor is any descriptor encompassed by the above definitions, description or discussion that is used as a molecular descriptor of a drug, molecule or molecular substance used in any phase of the pharmaceutical industry. Such phases include research, development, testing, manufacture or usage of a drug or other molecule or molecular substance in the pharmaceutical industry. A molecular descriptor includes any descriptor used in animal, cell line or human studies. Any descriptor of an auxiliary molecule (that is not the, or a principally active compound) such as a molecule that is part of a drug delivery system is an example of a molecular descriptor. Any combination of one or more such molecular descriptors is also a molecular descriptor. Versions of the invention have utility and operability in many areas of chemistry outside the pharmaceutical industry as well. Therefore, for example, any descriptor of a molecular substance used in any phase of the chemical industry that is encompassed in the definitions, discussion or description of a geometry-based molecular descriptor is an example of a geometry-based molecular descriptor. Such phases include (but are not limited to) research, development, testing, manufacture or usage of a molecule in the chemical industry. Any combination of one or more such geometry-based molecular descriptors is also a geometry-based molecular descriptor. Versions of the invention have a very wide range of applicability. Versions of the invention have operability and utility for molecules that are not man-made or are extracts or modifications of natural substances. Therefore, a descriptor of any molecule that is encompassed in the definitions, discussion or description of a geometry-based molecular descriptor in essentially any branch of chemistry, or related discipline is an example of a geometry-based molecular descriptor.

The distinction between a molecular property (or response) and a molecular descriptor (or predictor) is essentially arbitrary in that it is possible to designate a descriptor(or predictor) as a property (or response).

A molecular property (response) includes (but is not necessarily limited to) (1) any measurable, inferable or observable physical, chemical, or biological property of a molecule. In addition, any (2) molecular descriptor as described above (including predictor type descriptors) is a molecular property (3) any combination of one or more of the properties as described in (1) and (2) of this paragraph is a molecular property. Any mathematical computation that uses one or more of the properties as described in (1), (2) and (3) of this paragraph is a molecular property.

Any property of a drug, molecule or molecular substance used in any phase of the pharmaceutical industry is an example of a molecular property. Such phases include research, development, testing, manufacture or usage of a drug or other molecule or molecular substance in the pharmaceutical industry. A molecular property includes any property used in animal, cell line or human studies. Any property of an auxiliary molecule (that is not the, or a principally active compound) such as a molecule that is part of a drug delivery system is an example of a molecular property. Any combination of one or more such molecular properties is also a molecular property.

Molecular properties include (but are not limited to) drug potency, drug toxicity, solubility, drug absorption profile, positive or negative drug effects. A molecular property is any drug effect on one or more individuals that is associated with one or more descriptions (or descriptors) of the genetic make-up of the one or more individuals. Any ADMET property is a molecular property. The distinction between a property (response) and a descriptor is somewhat arbitrary in that it is possible to designate a descriptor as a property (response).[XII]

[XII] Versions of the invention have utility and operability in many areas of chemistry outside the pharmaceutical industry as well. Therefore, for example, any property of a molecular substance used in any phase of the chemical industry is an example of a molecular property. Such phases include (but are not limited to) research, development, testing, manufacture or usage of a molecule in the chemical industry. Any combination of one or more such molecular properties is also a molecular property. Versions of the invention have a very wide range of applicability. Versions of the invention have operability and utility for molecules that are not man-made or are extracts or modifications of natural substances. (Molecule: In this application, the term molecule is used in the term's broadest possible sense. It is also possible for the term molecule to mean a complex of one or more molecules (wherein the term "molecules" is used in the term's usual sense) that are in close proximity. As is evident, versions of the invention have utility and operability in the study of some such molecular complexes that are within the meaning of the term "molecule" as used in this application.)

Some further details on molecular descriptors, properties, and other descriptors can be had in Molecules 2002, 7, 566-600; An Introduction to QSAR Methodology by Richon and Young, (Network Science), http://www.netsci.org/Science/Compchem/feature19.html, published Oct. 1997; Chemometrics and Intelligent Laboratory Systems 60 (2002), pp. 5-11; Goodman & Gilman's The Pharmacological Basis of Therapeutics ISBN: 0071354697, each of these four publications is incorporated herein by reference to the fullest extent of the law.

Further General Description of Versions of the Invention

General and more specific descriptions of versions of the invention are given below. Some versions of the invention described below are-for (or handle) essentially any kind of data or data objects, including abstract data or data objects, or real-world data or data objects. Some versions of the invention described below are more specifically for (or handle) essentially molecular data (such as geometry-based molecular descriptors) or molecular data objects.

I. Some Versions of Simple Segmentation Processes

Some Simple Versions of the Invention Use one Segmenting Algorithm, one Property (Response) and one Descriptor to Segment a Group of Data Objects:

As described above in references 1-9 inclusive and the DPSA Appendix, a segmenting algorithm essentially segments data, so that the Y values (or response values) that correspond to each segment are essentially homogeneous. Each segment is an interval or a grouping of X values (or descriptor values). And each Y value (or response value) is associated with an X value (or descriptor value). Thus, in a simple usage, a segmenting algorithm segments using one response Y, and one descriptor X.

In this application, a property (for example a molecular property) is equivalent to Y (or the response); and a descriptor (for example a molecular descriptor) is equivalent to X (or the descriptor). And each property (response) value corresponds to a descriptor value in that the property (response) value and descriptor value belong to the same data object. Thus, a segmenting algorithm (in the context of versions of the invention) essentially segments a group of data objects so that the property (response) values within each descriptor value segment are essentially homogeneous. Thus, in a simple usage (for versions of the invention), a segmenting algorithm segments using one property (response), and one descriptor.

Continuing, a segmenting algorithm (in the context of some versions of the invention) essentially segments a group of molecules (or molecular data objects) so that the molecular property (response) values within each segment are essentially homogeneous; and each segment is essentially an interval of values for a single molecular descriptor. Thus, in a simple usage (for some versions of the invention), a segmenting algorithm segments a group of molecules using one molecular property (response), and one molecular descriptor.

Usage of Geometry-Based Molecular Descriptor(s) and Segmenting Algorithms for Segmenting A process (or apparatus) that essentially segments a group of molecules using one or more segmenting algorithms and one or more geometry-based molecular descriptors is a version of the invention. Such inventions and related inventions have been invented by the inventor and are described in this application.

A general description of a version of such inventions is as follows.

SSP#1 A computer-based method of segmenting a group of two or more data objects into two or more subgroups using a segmenting algorithm and a descriptor and a response, comprising:

obtaining a value for the descriptor and the response for each object in the group; and segmenting the data objects in the group into two or more subgroups using the segmenting algorithm, the response value and the descriptor value for each object in the group.

An example of the segmenting algorithm of SSP#1 is a DPSA, a special DPSA (FSA, a Bd-DPSA, PTd-DPSA). Versions of SSP#1 handle any kind of data or data objects including real-world data, such as molecular data and data objects, and geometry-based descriptors. Versions of SSP#1 output data in segmented form to a monitor, LCD, printer or equivalent device for use by a human user or users. Any computer-based method that uses data in segmented form from a version of SSP#1, wherein the method essentially outputs data to a monitor or equivalent device is a version of the invention. More specific versions of SSP#1 handle essentially molecular data or molecular data objects. A description of some more specific such versions is as follows:

SMSP#1 A computer-based method of segmenting a group of two or more data objects as SSP#1, wherein each of the data objects is a molecular data object, the response is a molecular property and the descriptor is a geometry-based descriptor.

Versions of SMSP#1 output data in segmented form to a monitor, LCD, printer or equivalent device for use by a human user or users. Any computer-based method that uses data in segmented form from a version of SMSP#1, wherein the method essentially outputs data to a monitor or equivalent device is a version of the invention.

A collection of two or more subgroups of data objects, wherein the subgroups were generated by a segmentation process that segmented a group is defined as a segmentation of the group of data objects.

Segmenting a group of data objects (such as molecular data objects) using more than one descriptor or more than one segmenting algorithm also has utility. In order to further describe these type of versions of the invention, it is helpful to examine (1) groups of data objects having more than one descriptor; and it is helpful to examine (2) segmenting algorithms in further detail as well. We start with (1) first.

(1) Groups of data objects having more than one descriptor: A very helpful (nonlimiting) way to conceptualize a group (or subgroup) of data objects, the objects' property (response) and descriptor (or predictor) values is the matrix shown in FIG. 3. The objects are denoted $O_1, \ldots, O_n$. The objects' property (response) is denoted as P and the objects' descriptors (or predictors) are denoted as $D_1, \ldots, D_M$. The particular value (quantitative or qualitative) of a particular object's property (or descriptor) is indicated in the matrix cell corresponding to the object and property (or descriptor). In cases in which it is not possible to ascertain the particular value of a descriptor, the value is indicated in the matrix as "missing". (This conceptualization is essentially applicable to any group or subgroup of data objects.)

(2) A further discussion of segmenting algorithms. Segmenting algorithms have been discussed above and in the references 1-9, and the DPSA Appendix. Characteristics of a segmenting algorithm often include a) one or more measures of homogeneity/inhomogeneity. These measures include (1) a measure of the homogeneity of property (response) values for the data objects in each segment or (2) an overall (for all the segments combined) measure of the homogeneity of the property (response) values in each segment or (3) a measure of the inter-segment property (response) value inhomogeneity (such a measure is pair-wise or for any combination of two or more segments) or (4) any combination of (1), (2) or (3). Examples of such measures of homogeneity or inhomogeneity are found in the references 1-9, and the DPSA Appendix and include statistical measures, least square type measures and deviance measures. Other characteristics of a segmenting algorithm often include a) one or more stop criteria (defined below), b) the manner in which it chooses a final segmentation from various possible segmentations, c) the number of segments it generates in segmenting, d) the manner in which it performs its calculations. This list, a) through d) is not necessarily exhaustive. It is not necessary for a segmenting algorithm to choose a best or even approximately best segmentation, although such a choice or choices have utility. "Best segmentation" means best in terms of one or more measures of homogeneity/inhomogeneity or similar measures.

A stop criterion is a criterion that tells the algorithm that there is (1) no acceptable potential segmentation or segmentations or (2) to stop seeking a potential (or candidate) segmentation or segmentations or a similar such criterion or criteria. Examples include (but are not limited to) when potential segmentations have too few objects in one or more segments or the measure of homogeneity/inhomogeneity between segments of potential segmentations is low, for example statistically insignificant. In this patent application the term "stop criterion" (or "stop criteria") includes any stop criterion (or criteria) known to a person of ordinary skill in the art of data segmenting, or recursive partitioning or neighboring art(s).

II. Some Versions of Node Segmentation Processes

Segmentation Processes that Segment a Group of Data Objects (Such as Molecular Data Objects) Using One or More Segmenting Algorithms and One or More Descriptors (Such as One or More Descriptors that are a Geometry-Based Descriptors).

A process that produces a segmentation of a group of data objects by generating one or more candidate segmentations of the group using one or more descriptors and using one or more segmenting algorithms and that elects one of the candidate segmentations as a final segmentation is referred to as a node segmentation process or as a group segmentation process. (A node or group segmentation process that uses one or more geometry-based descriptors (or predictors) to segment a group containing one or more molecular data objects is a version of the invention.) Inherent in the election of a final segmentation by a node segmentation process is the possible use of the elected segmentation for generation of one or more daughter nodes; wherein each daughter node corresponds to a segment in the elected segmentation. And in effect, the daughter nodes and the (original) node constitute a nodal tree, wherein the (original) node is the parent node of each of the daughter nodes. (The term group of data objects and node of data objects is used somewhat interchangeably in this patent application.) As the name implies, a candidate segmentation is a segmentation that could be elected by a process as a (or the) final segmentation.

Description of a Version of a Node Segmentation Process

A description of a version of a node or group segmentation process is as follows.

GenNSP#1 A computer-based method of segmenting a group (or node) of two or more data objects into two or more subgroups, wherein each data object has a response value and a value for each of one or more descriptors, comprising:

choosing one or more segmenting algorithms for each descriptor and generating one or more candidate segmentations for each descriptor; and electing one of the candidate segmentations as a final segmentation and designating all of the data objects in each of one or more segments of the final segmentation as a subgroup.

The term "node segmentation process" is abbreviated as NSP. As with some segmenting algorithms, a node segmentation process does not necessarily elect a best or approximately best segmentation. Some versions of segmentation processes elect a statistically meaningful segmentation. Versions of an NSP that elect a best or approximate best segmentation have definite utility and are preferred versions. Unless specifically stated otherwise some embodiments of each version of GenNSP#1 (or NSP described herein) handle any kind of data or data objects including real-world data, such as molecular data and data objects, and geometry-based descriptors. Unless specifically stated otherwise some embodiments of each version of GenNSP#1 (or NSP described herein) output data in segmented form to a monitor, LCD, printer or equivalent device for use by a human user or users. Any computer-based method that uses data in segmented form from a version of GenNSP#1 (or NSP described herein), wherein the method essentially outputs data to a monitor or equivalent device is a version of the invention.

Segmenting Algorithms of an NSP

It is possible for some versions of GenNSP#1 to choose one or more segmenting algorithms for each descriptor so that for each of one or more descriptor pairs, the one or more algorithms for each descriptor of each descriptor pair are different. In some cases, for technical convenience and efficiency, the same one or more segmenting algorithms are chosen for each descriptor. An example of the segmenting algorithm of GenNSP#1 is a DPSA, an FSA, a Bd-DPSA. FSAs are fast enough that they allow human interaction with one or more NSPs.

More specific versions of GenNSP#1 handle essentially molecular data or molecular data objects. A description of some more specific such versions of GenNSP#1 are as follows: GenMNSP#1 A computer-based method of segmenting a group of two or more data objects as GenNSP#1, wherein each of the data objects is a molecular data object, the response is a (molecular) property and one or more of the descriptors is a geometry-based (molecular) descriptor.

GenMNSP#2 A computer-based method of segmenting a group of two or more data objects as GenNSP#1, wherein each of the data objects is a molecular data object, the response is a (molecular) property, wherein each data object has a value for each of two or more descriptors, and wherein one or more of the descriptors is a geometry-based (molecular) descriptor.

FSA or Bd-DPSA Capable Node Segmentation Processes

A specific kind of node segmentation process is a process wherein (1) one or more FSAs, or (2) one or more Bd-DPSAs, or a combination of both (1) and (2) is available to use to segment one or more nodes. Such a node segmentation process essentially chooses one or more segmenting algorithms from a battery (or group) of one or more segmenting algorithms, wherein one or more of the segmenting algorithms in the battery is an FSA or a Bd-DPSA. Such a node segmentation process is an FSA or Bd-DPSA Capable Node Segmentation Process. A description of a version of an FSA or Bd-DPSA Capable Node Segmentation Process is as follows.

FSAorBd-DPSACapable NSP#1 A computer-based method of segmenting a group (or node) of two or more data objects into two or more subgroups, wherein each data object has a response value and a value for each of one or more descriptors, comprising:

choosing one or more segmenting algorithms for each descriptor from a battery of one or more segmenting algorithms, wherein one or more of the algorithms in the battery is an FSA or a Bd-DPSA and generating one or more candidate segmentations for each descriptor; and electing one of the candidate segmentations as a final segmentation and designating all of the data objects in each of one or more segments of the final segmentation as a subgroup.

For some versions of FSAorBd-DPSACapable NSP#1 the algorithm battery includes one or more FSAs and one or more Bd DPSAs.

More specific versions of FSAorBd-DPSACapable NSP#1: For some more specific versions of FSAorBd-DPSACapable NSP#1 the battery of algorithms is limited so that one or more of the algorithms in the battery is either (1) an FSA or (2) a Bd-DPSA. In (1) the node segmentation process is an FSA capable node segmentation process; in (2) the segmentation process is a Bd-DPSACapable node segmentation process. A description of some such versions of FSAorBd-DPSACapable NSP#1 is as follows.

(1) FSACapable NSP#1 A computer-based method of segmenting a group (or node) of data objects as FSAorBd-DPSACapable NSP#1, wherein one or more of the algorithms in the battery is an FSA.

(2) Bd-DPSACapable NSP#1, computer-based method of segmenting a group (or node) of data objects as FSAorBd-DPSACapable NSP#1, wherein one or more of the algorithms in the battery is a Bd-DPSA.

More specific versions of FSAorBd-DPSACapable NSP#1 for molecular data or data objects. More specific versions of FSAorBd-DPSACapable NSP#1 handle essentially molecular data or molecular data objects. A description of some more specific such versions of FSAorBd-DPSACapable NSP#1 is follows:

FSAorBd-DPSACapable Mol NSP#1: A computer-based method of segmenting a group (or node) of data objects as any one of the methods FSAorBd-DPSACapable NSP#1, FSACapable NSP#1, or Bd-DPSACapable NSP#1, wherein each data object is a molecular data object, wherein the response is a molecular property, wherein each descriptor is a molecular descriptor, and wherein one or more of the descriptors is a geometry-based molecular descriptor.

Special NSPs

Any NSP that uses or has available for use a special DPSA is a special NSP. Versions of NSPs that use or have available for use FSAs or Bd-DPSAs have been described. Similarly, any similar NSP that uses or has available for use one or more PTd-DPSAs is a special NSP.

Special using NSPs: An NSP that uses one or more FSAs is an FSA using NSP. An NSP that uses one or more Bd-DPSAs is a Bd-DPSA using NSP. An NSP that uses one or more PTd-DPSAs is a PTd-DPSA using NSP.

Special capable NSPs: An NSP that has one or more FSAs available for use is an FSA capable NSP. An NSP that has one or more Bd-DPSAs available for use is a Bd-DPSA capable NSP. An NSP that has one or more PTd-DPSAs available for use is a PTd-DPSA capable NSP.

Particular Special NSPs: An NSP that uses, or has available for use, one or more FSAs is an FSA special NSP. An NSP that uses, or has available for use, one or more Bd-DPSAs is a Bd-DPSA special NSP. An NSP that uses or has available for use one or more PTd-DPSAs is a PTd-DPSA special NSP.

Human Interaction NSPs

In addition, some versions of NSPs essentially allow human interaction in that a human operator (1) chooses one or more of the descriptors of the method (that an NSP uses to generate the one or more candidate segmentations), (2) gives a command for an NSP to select descriptors (for use in segmenting); for some versions of NSPs, the selection is a random selection of descriptors (3) elects one of the candidate segmentations as a final segmentation, or (4) chooses one or more of the segmenting algorithms used by the method or (5) a combination of two or more of (1), (2) or (3) of this paragraph.

A description of some examples of such versions of the invention are as follows. Each of these versions is an example of a Human Interaction NSP(abbreviated HI-NSP). Any NSP that includes human interaction or is similar to one of the HI-NSPs recited herein (HI#1-GenNSP#1, HI#2-GenNSP#1, HI#3-GenNSP#1, HI#4-GenNSP#1, HI#1-GenNSP#2, or RandHI#1-GenNSP#2), is an HI-NSP.

HI#1-GenNSP#1 A computer-based method of segmenting a group (or node) of two or more data objects into two or more subgroups as any one of the methods GenNSP#1, GenMNSP#1, GenMNSP#2, FSAorBd-DPSACapable NSP#1, FSACapable NSP#1, Bd-DPSACapable NSP#1 method, FSAorBd-DPSACapable Mol NSP#1, wherein one or more of the descriptors is chosen by a human operator.

HI#2-GenNSP#1 A computer-based method of segmenting a group (or node) of two or more data objects into two or more subgroups as any one of the methods GenNSP#1, GenMNSP#1, GenMNSP#2, FSAorBd-DPSACapable NSP#1, FSACapable NSP#1, Bd-DPSACapable NSP#1method, FSAorBd-DPSACapable Mol NSP#1, wherein the electing of the final segmentation uses one or more commands from a human operator.

HI#3-GenNSP#1 A computer-based method of segmenting a group (or node) of two or more data objects into two or more subgroups as any one of the methods GenNSP#1, GenMNSP#1, GenMNSP#2, FSAorBd-DPSACapable NSP#1, FSACapable NSP#1, Bd-DPSACapable NSP#1 method, FSAorBd-DPSACapable Mol NSP#1, wherein a human operator selects a particular candidate segmentation, and wherein the electing of the particular candidate by the method as the final segmentation uses one or more commands from the operator.

HI#4-GenNSP#1 A computer-based method of segmenting a group (or node) of two or more data objects into two or more subgroups as any one of the methods GenNSP#1, GenMNSP#1, GenMNSP#2, FSAorBd-DPSACapable NSP#1, FSACapable NSP#1, Bd-DPSACapable NSP#1 method, FSAorBd-DPSACapable Mol NSP#1, wherein the choosing of one or more segmenting algorithms for each of one or more descriptors by the method uses one or more commands from a human operator.

HI#1-GenNSP#2 A computer-based method of segmenting a group (or node) of two or more data objects into two or more subgroups, wherein each data object has a response value and a value for each of one or more descriptors, comprising:

receiving one or more commands from a human user to select one or more of the descriptors, and selecting a subset of the descriptors;

choosing one or more segmenting algorithms for each descriptor in the subset and generating one or more candidate segmentations for each in descriptor in the subset; and electing one of the candidate segmentations as a final segmentation and designating all of the data objects in each of one or more segments of the final segmentation as a subgroup.

RandHI#1 -GenNSP#2 A computer-based method of segmenting a group (or node) of two or more data objects into two or more subgroups as the method HI#1-GenNSP#2, wherein the subset is a randomly selected subset of the descriptors.

Stop Criteria and NSPs

As described above, some segmenting algorithms use one or more stop criteria to stop segmenting. Versions of NSPs choose one or more segmenting algorithms to achieve a final segmentation (or split) of a node. Each of one or more versions of an NSP chooses one or more segmenting algorithms to segment a node, wherein each of the one or more algorithms use one or more stop criteria. Thus it is possible for a node to meet one or more stop criteria of one or more segmenting algorithms chosen by each of one or more NSPs.

III. Some Versions of Processes that Generate Nodal Trees.

Use of one or more node segmentation processes to generate a nodal tree. By using such a node segmentation process on an initial group (or root node) of molecular data objects and applying one or more such node segmentation processes recursively (wherein only one process is used on one node) to zero or more descendant nodes, a nodal tree is generated. Such a nodal tree is similar to nodal trees discussed earlier in this application.

Description of a Version of a Segmenting Nodal Tree Generation Process

GenSNTGP#1 A computer-based method for clarifying a relationship between a response and one or more descriptors by generating a data structure, the response and each descriptor having a value for each data object of a group of data objects, the data structure being a nodal tree or an equivalent thereof, the root of the tree being the group of data objects, comprising:

defining a nodal tree-node segmenting procedure, comprising i), ii), iii), iv):

i)choosing an unsegmented node that has not been previously segmented;

ii) choosing a node segmentation process for the unsegmented node;

iii) segmenting the unsegmented node into two or more subgroups using the node segmentation process chosen for the unsegmented node in ii); and iv) making the unsegmented node a segmented tree parent node and making each of one or more of the subgroups of iii) an unsegmented tree daughter node of the segmented tree parent node of iv);

applying the nodal tree-node segmenting procedure to the root node first; and applying the nodal tree-node segmenting procedure recursively to zero or more unsegmented nodes of the tree.

Description of some Versions of a Segmenting Nodal Tree Generation Process that Utilize One or More Stop Criteria.

Figure 4:
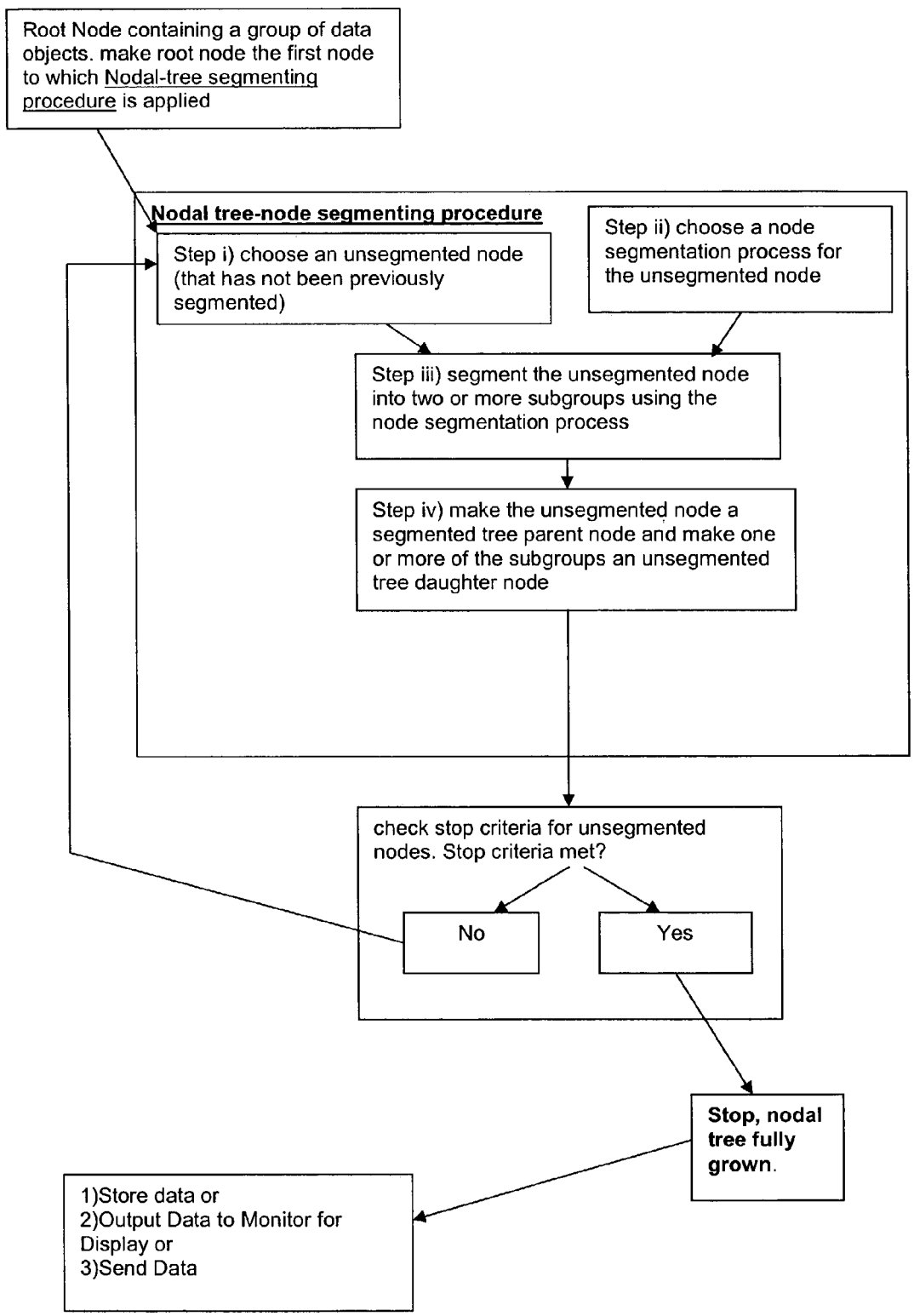
FIG. 4 is an illustration of a Segmenting Nodal Tree Generating (or Growing) Process similar to GenSNTGP#1. The Figure illustrates that versions of the Invention output data to a display device, to a storage device, or send data (such as over the internet) or some combination of two or more of these.

In addition, it is possible to practice a process such as GenSNTGP#1 until one or more stop criteria are met for one or more nodes. The nature of a stop criterion or criteria were previously discussed. An example of such a version of the invention is described next and illustrated in FIG. 4.

Description of a Version of a Segmenting Nodal Tree Generation Process that Uses One or More Stop Criteria SNTGP#2 A computer-based method for clarifying a relationship between a response and one or more descriptors by generating a data structure, the response and each descriptor having a value for each data object of a group of data objects, the data structure being a nodal tree or an equivalent thereof, the root of the tree being the group of data objects, comprising:

defining a nodal tree-node segmenting procedure, comprising i), ii), iii), iv):

i) choosing an unsegmented node that has not been previously segmented;

ii) choosing a node segmentation process for the unsegmented node;

iii) segmenting the unsegmented node into two or more subgroups using the node segmentation process chosen for the unsegmented node in ii); and iv) making the unsegmented node a segmented tree parent node and making each of one or more of the subgroups of iii) an unsegmented tree daughter node of the segmented tree parent node of iv);

applying the nodal tree-node segmenting procedure to the root node first; and applying the nodal tree-node segmenting procedure recursively to one or more unsegmented nodes of the tree until one or more stop criteria are met for each of one or more unsegmented nodes.

Further description of each of the methods GenSNTGP#1 and GenSNTGP#2. (In the above descriptions of GenSNTGP#1 and GenSNTGP#2, the indices i), ii), iii), and iv) are included only for the purpose of clarity. The indices i), ii), iii), and iv) are nonlimiting and do not necessarily limit the method to a step method, or to a specific step or steps, or to a specific number or order of steps.) Unless specifically stated otherwise some embodiments of each version of GenSNTGP#1 and GenSNTGP#2 (or any process that generates a nodal tree described herein) handle any kind of data or data objects including real-world data, such as molecular data and data objects, and geometry-based descriptors. Unless specifically stated otherwise some embodiments of each version of GenSNTGP#1 and GenSNTGP#2 (or any process that generates a nodal tree described herein) output data in segmented form to a monitor, LCD, CRT, printer or equivalent device for use by a human user or users. Any computer-based method that uses data in segmented form from a version of GenSNTGP#1 (or any process that generates a nodal tree described herein), wherein the method essentially outputs data to a monitor or equivalent device is a version of the invention.

Node Segmentation Process or Processes chosen by the nodal tree-node segmenting procedure of each of the methods GenSNTGP#1 and GenSNTGP#2. GenSNTGP#1 uses a nodal tree-node segmenting procedure. (The abbreviation of nodal tree-node segmenting procedure is NT-NSPrcdr.) In GenSNTGP#1, an node segmentation process (an NSP) is chosen by the NT-NSPrcdr in ii) one or more times. Specifically an NSP is chosen for each unsegmented node that is split (or segmented) by the NT-NSPrcdr. For some versions of GenSNTGP#1, two NSPs chosen for each of one or more pairs of unsegmented nodes[XIII] are two differing NSPs. So it is possible for a version of GenSNTGP#1 to essentially choose several differing NSPs. In some situations, for purposes of technical convenience, essentially the same NSP is chosen for each unsegmented node that is split by GenSNTGP#1. The description and details of this paragraph with respect to NSPs are also true of GenSNTGP#2. It is possible for each version of GenSNTGP#1 and GenSNTGP#2 to choose each version of an NSP described in this document one or more times. Versions of NSPs described herein include special NSPs and HI-NSPs. A NT-NSPrcdr, wherein the procedure chooses one or more special NSPs is a special NT-NSPrcdr. Such an NT-NSPrcdr uses one or more special NSPs. A special NT-NSPrcdr uses or has available for use, one or more special NSPs. And therefore, a special NT-NSPrcdr effectively uses[XIV] one or more special DPSAs.

[XIII] An NSP is chosen for each (pair) of two unsegmented nodes that are acted on by the NT-NSPrcdr, for a total of two chosen NSPs (possibly different) for each pair of nodes.

[XIV] The term "effectively uses" means that a special DPSA is effectively used or effectively available for use by the procedure. Such effective use or effective available use by the procedure is through the one or more special NSPs that the procedure uses or through the one or more special NSPs are available for use by the procedure.

Using NT-NSPrcdrs

A special NT-NS Prcdr wherein the procedure chooses one or more special NSPs is a special-using NT-NS Prcdr. Some such versions of special using NT-NS Prcdrs have been described above. A special-using NT-NS Prcdr that chooses one or more FSA special NSPs is an FSA-using NT-NS Prcdr. A special-using NT-NS Prcdr that chooses one or more Bd-DPSA special NSPs is an Bd-DPSA-using NT-NS Prcdr. A special-using NT-NS Prcdr that chooses one or more PTd-DPSA special NSPs is an PTd-DPSA—using NT-NS Prcdr.

Able NT-NSPrcdrs

A nodal tree-node segmenting procedure wherein one or more special NSPs is available for use by the procedure is a special-able NT-NS Prcdr. (A special-able NT-NS Prcdr is also a special NT-NS Prcdr.) Such a special-able NT-NS Prcdr essentially chooses one or more special NSPs from an ensemble (or group) of one or more NSPs, wherein one or more of the NSPs in the ensemble is a special NSP. Such a special-able NT-NS Prcdr essentially has available an ensemble that includes one or more special NSPs. A special-able NT-NS Prcdr that has available an ensemble with one or more FSA special NSPs is an FSA-able NT-NS Prcdr. A special-able NT-NS Prcdr that has available an ensemble with one or more Bd-DPSA special NSPs is an Bd-DPSA-able NT-NS Prcdr. A special-able NT-NS Prcdr that has available an ensemble with one or more PTd-DPSA special NSPs is an PTd-DPSA-able NT-NS Prcdr.

Particular special NT-NS Prcdrs As is clear from the above description, a special NT-NS Prcdr effectively uses one or more special DPSAs. A special NT-NS Prcdr wherein the procedure is an FSA-able NT-NS Prcdr or an FSA-using NT-NS Prcdr is an FSA-special NT-NS Prcdr. An FSA-special NT-NS Prcdr, effectively uses one or more FSAs.

A special NT-NS Prcdr wherein the procedure is an Bd-DPSA-able NT-NS Prcdr or an Bd-DPSA-using NT-NS Prcdr is an Bd-DPSA-special NT-NS Prcdr. An Bd-DPSA NT-NS Prcdr, effectively uses one or more Bd-DPSAs. A special NT-NS Prcdr wherein the procedure is an PTd-DPSA-able NT-NS Prcdr or an PTd-DPSA—using NT-NS Prcdr is an PTd-DPSA-special NT-NS Prcdr. An PTd-DPSA NT-NS Prcdr, effectively uses one or more PTd-DPSAs.

A More Formal Description of (1) a Special-Able NT-NS Prcdr and (2) a Nodal Tree Generating (or Growing) Process that Uses the Special-Able NT-NS Prcdr A process similar to GenSNTGP#1 that uses a special-able NT-NS Prcdr, specifically an FSA-able NT-NS Prcdr is described below.

FSA-able GenSNTGP#1 A computer-based method for clarifying a relationship between a response and one or more descriptors by generating a data structure, the response and each descriptor having a value for each data object of a group of data objects, the data structure being a nodal tree or an equivalent thereof, the root of the tree being the group of data objects, comprising:

defining a nodal tree-node segmenting procedure, comprising i), ii), iii), iv):
  i) choosing an unsegmented node that has not been previously segmented;
  ii) choosing a node segmentation process for the unsegmented node from an ensemble of one or more NSPS, wherein one or more of the ensemble NSPs is an FSA special NSP;
  iii) segmenting the unsegmented node into two or more subgroups using the node segmentation process chosen for the unsegmented node in ii); and
  iv) making the unsegmented node a segmented tree parent node and making each of one or more of the subgroups of iii) an unsegmented tree daughter node of the segmented tree parent node of iv);
applying the nodal tree-node segmenting procedure to the root node first; and
applying the nodal tree-node segmenting procedure recursively to zero or more unsegmented nodes of the tree.[XV]

[XV] In this example, the language "defining a nodal tree-node segmenting procedure, comprising i), ii), iii), iv)" is used. The same invention (or an essentially exact equivalent) is described by the language "defining a nodal tree-node segmenting procedure, wherein the procedure comprises i), ii), iii), iv)".

It is also possible to practice a method such as FSA-able GenSNTGP#1 above with an additional data gathering step or step-like part. For example: A method such as FSA-able GenSNTGP#1, wherein one or more of the data objects is a real-world object, further comprising: collecting one or more descriptor values or one or more property values of each of one or more of the real-world objects by physical measurement or observation.

Human Interaction in Some Versions of Each of GenSNTGP#1 and GenSNTGP#2

An important feature of some versions of each of the methods GenSNTGP#1 and GenSNTGP#2, is that human interaction/intervention is a part of growing the nodal tree. One way that human interaction is part of versions of these tree growing processes is through one or more Human Interaction NSPs chosen in ii) by the processes.

For some versions of each of GenSNTGP#1 and GenSNTGP#2, the nodal tree grown by each method is a subtree of a larger (previously generated) nodal tree, and the root node of the grown nodal tree (grown by each method) is a daughter node of the larger tree. This situation is a situation for which human interaction in growing a nodal tree by versions of each method (GenSNTGP#1 and GenSNTGP#2) is important.

A more formal description of versions of tree generating (or growing) processes that include human interaction is as follows.

HIGenSNTGP#1 A computer-based method for clarifying a relationship between a response and one or more descriptors by generating a data structure, as in any one of the methods GenSNTGP#1 or GenSNTGP#1, wherein the nodal tree-node segmenting procedure chooses one or more Human Interaction NSPs, one or more times.

Versions of each of GenSNTGP#1 and GenSNTGP#1 handle essentially any kind of data or data objects, including real-world data or real-world data objects, some more specific versions of each of GenSNTGP#1 and GenSNTGP#1 handle molecular data or molecular data objects.

A description of some such versions of the invention is as follows.

MoISNTGP#1 A computer-based method for clarifying a relationship between a response and one or more descriptors as any one of the methods GenSNTGP#1 or GenSNTGP#1, wherein each of one or more data objects is a molecular data object, wherein each of one or more of the descriptors is a geometry-based molecular descriptor, and wherein the response is a molecular property.

An example of MoISNTGP#1 is a method as MoISNTGP#1 wherein each of the data objects is a molecular data object.

EXAMPLE 1

An illustrative example of a version of the invention makes use of a novel type of descriptor (or predictor) to describe chemical compounds that are used as drugs. In this version of the invention, the descriptors (or predictors) comprise atom class pairs and the shortest (through compound) path length between the two focal atoms of the atom class pair. An example of such atom class pairs and a compound is shown in FIG. 1.

FIG. 1 shows a compound that illustrates two quantitative descriptors or predictors (with respective quantitative values) that use atom class pairs. In FIG. 1, a first quantitative descriptor and value is denoted "OC-8-CCC" and a second quantitative descriptor and value is denoted "CCCCC-2-CC". The first descriptor consists of a first atom class denoted "OC" and a second atom class denoted "CCC". The first letter in the denotation is the focal atom of the atom class and the following letters on the list represent atoms attached to the focal atom of the atom class. Thus "O" is the focal atom of the first class, and this "O" represents the Oxygen circled in FIG. 1; and the "C" of "OC" represents the single Carbon attached to the circled Oxygen. The first "C" of the second atom class pair denoted "CCC" is the circled aromatic carbon and the following "CC" represents the two aromatic Carbons attached to the circled aromatic Carbon. The number "8" is the number of bonds in the shortest path through the molecule between the focal Carbon and the focal Oxygen of the atom class pair. (Attached hydrogens are considered in some of the descriptors, but not in this particular example)

Thus, the first descriptor is partly denoted "OC-b-CCC", wherein "OC" means an oxygen attached to only one carbon, "CCC" means a carbon (focal carbon) attached to only two carbons and b is the number of bonds in the shortest path through the molecule between the focal carbon and the oxygen. For this particular compound (data object), "b" is 8.

However, this (partial) denotation of the first descriptor is not unique for the compound: there are three atom classes in the compound that are described by "OC" and there are six atom classes that are described by "CCC". And there are nine possible atom class pairs with differing "b" values that are described by "OC-b-CCC". In order to make the value of the first descriptor unique, the pair (or pairs) with the largest "b" value is specified to be the descriptor. Thus the full denotation of the first descriptor is "PLHI: OC-b-CCC", wherein PLHI stands for "Path Length High" and stipulates the pair or pairs with the largest "b" value. The criterion of selecting the largest "b" value, the PLHI is known as a selecting criterion for the descriptor.

Thus the first descriptor is a quantitative descriptor and the value of the descriptor is "b". The value "b" is a unique quantitative value for any one compound when the atom class pair of the first descriptor is present in the compound. When the atom class pair of the first descriptor is not present in a compound, the value of the descriptor is "not applicable" or "missing". ("not applicable" and "missing" are used interchangeably in this application, although making a distinction has utility in some cases.)

Similarly the second descriptor value denoted "CCCCC-2-CC" in FIG. 1 represents the circled ring Carbon (focal atom) attached to four carbons that is 2 bonds away from the terminal circled Carbon (focal atom) attached to one Carbon. The number "2" is the number of bonds in the shortest path through the molecule between the two focal carbons.

The second descriptor is partly denoted "CCCCC-b-CC", wherein "CCCCC" means a Carbon (focal carbon) attached to only four carbons, "CC" means a carbon (focal carbon) attached to only one carbon and b is the number of bonds in the shortest path through the molecule between the two focal carbons. For this particular compound (data object), "b" is 2.

Similarly the full denotation of the second descriptor is "PLLO: CCCCC-b-CC", wherein "PLLO" stands for "Path Length Low". The second descriptor is a quantitative descriptor and the value of the descriptor is "b" or "missing"; the value of the second descriptor is unique for any one compound (data object).

The following is an example of the use of such quantitative descriptors (or predictors) to analyze chemical compounds such as drugs. Quantitative descriptors (or predictors) similar the two descriptors described above are applied to a group of 159 chemical compounds. A descriptor (or predictor)value is obtained for each descriptor (or predictor)for each compound in the group. A property (or response) value is obtained for each compound in the group. In this particular case, the property (or response) is drug potency.

Figure 2:
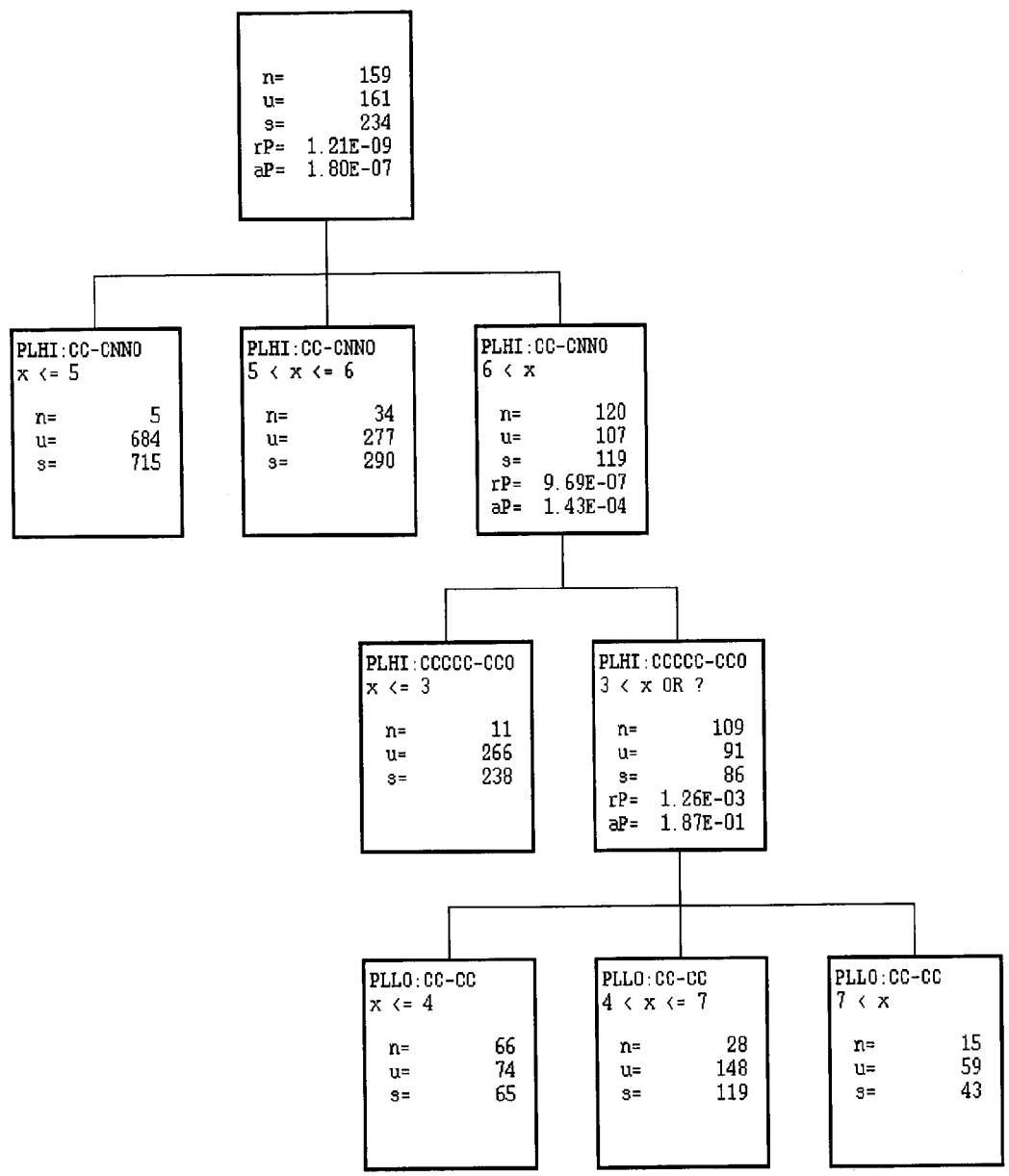
FIG. 2 Illustration of a Nodal Tree generated by a version of the invention, described in Example 1. The data objects are molecules and the descriptors are geometry-based molecular descriptors.

In FIG. 2 a root node with 159 drugs (n=159) of average potency 161 (u=161) has been split into three daughter nodes. The particular descriptor used to make the segmentation is PLHI: CC-b-CNNO. The drugs in each of the three daughter nodes of the root have a similar potency and descriptor values. The leftmost daughter node has 5 drugs (n=5) each drug of potency approximately 684 (u=684) and descriptor b values <=5, the middle daughter node has 34 drugs (n=34) each drug of potency approximately 271 (u=271) and descriptor b values 5<b<=6, and the rightmost daughter node has 120 drugs (n=120) each drug of potency approximately 107 (u=107) and descriptor b values >6.

This nodal tree is generated by using segmentation and recursive partitoning techniques, such as S/RP P techniques described in the Description. (For some versions of the invention the segmentation process used on different parent nodes uses essentially different segmenting algorithms.) This nodal tree essentially sorts drugs into nodes so that each lower level node (close to the terminal nodes or leaves of the tree) has drugs with common atom class pairs that are separated by similar path lengths and have similar potency values. Generally there is greater sorting, and greater potency and descriptor value similarity (homogeneity) of objects in lower level nodes of the tree. And generally there is less sorting, and less potency and descriptor value similarity (homogeneity) of objects in higher level nodes of the tree near the root of the tree.

Some lower level high potency nodes of the tree essentially contain drugs with high potency and similar descriptor values. It is possible to conceptualize these descriptors (or predictors) and similar values as essentially clarifying the qualities of one or more effective pharmacophores that are correlated to the high potency of the drugs. Each of these one or more effective pharmacophores essentially includes the atom class pairs of some of the descriptors (or predictors) of the high potency nodes, the focal atoms of the pairs being separated by the respective quantitative values of the descriptors. The detailed path by which drug molecules are "split out" or segmented may be used to provide information on characteristics of molecular structures that are associated with higher drug potency.

Alternatively, these lower level high potency nodes of the tree elucidate predictive, correlation or causal type relationships between one or more of the similar descriptor (or predictor) values and drug potency.

In addition, the path (through the nodal tree) to a node whose drugs have lower potency may be used to provide information on characteristics of molecular structures that have no bearing on, or that actively inhibit drug potency.

A Conceptual Device to Aid in Further Understanding the Invention

Each node of the tree in this example 1 represents a group of compounds. A very helpful (nonlimiting) way to conceptualize a group (or node) of compounds, the compounds' property (or response) and descriptor (or predictor) values is the matrix shown in FIG. 3. The compounds (or data objects) are denoted $O_1, \ldots, O_n$. The compound property (response) is denoted as P and the compound descriptors (or predictors) are denoted as $D_1, \ldots, D_M$. In this example the property (response) is drug potency, the descriptors (or predictors) are atom class pairs and distance, and generally each descriptor (or predictor)value is a distance.

(Standard graph matching algorithms are used by versions of the invention to find all instances of an atom class in a compound (see Ullman, JR. An algorithm for subgraph isomorphism. J. Assoc. Comput. Mach. 23: 31-42 (1976). This paper is incorporated herein by reference. Standard graph traversing algorithms known in the art or neighboring arts are used by versions of the invention to compute path distances.

Alternative descriptors (or predictors) for use in other embodiments of the invention In example 1 above, the molecular features used were atom class pairs, and the focal atoms of each atom class in the pair were the distance measurement endpoints. Alternate embodiments of the invention use one or more other types of descriptor, including one or more of the descriptors (or predictors) detailed under descriptors, molecular descriptors and geometry-based molecular descriptors in the Description section of the application.

Other illustrative uses of geometry-based molecular descriptors by versions of the invention are shown and described in Golden Helix sales brochure: "Are you still taking a 'brute force' approach to High Throughput Screening?". This brochure is was included with U.S. Provisional application 60/225,113 and is incorporated herein by reference to the fullest extent of the law.

The brochure presents an Example application of versions of the invention on pages 11 through 15. This example application uses compounds from the NIH Developmental Therapeutics Program AIDS Antiviral Screen. The example application generates a nodal tree (Brochure pages 12 and 13) that elucidates relationships between drug potency and molecular characteristics of the drugs. In this example application, distances between atom class pairs (PLLO, PLHI) of drugs (molecular characteristics) are used to group or "segment" drugs into nodes. Drugs within nodes of the tree have various degrees of "likeness" or homogeneity in terms of drug potency and distances between one or more atom class pairs. In this example application, high potency nodes ($u \geqq 6$) are highlighted and one such node is circled.

Each node gives a descriptor (atom class pair, distance) used in the segmentation that created the node. Nodes also contain various numbers such as "n" (the number of drugs in the node), "u" (the average potency of drugs in the node), "s" (standard deviation), "rP"(raw (unadjusted) p-value for the segmentation) and "aP" (Bonferroni adjusted p-value for the segmentation).

This Example application illustrates versions of invention's capability to use a "training set" of compounds (drugs with known potencies) to generate a first nodal tree that correlates drug potency with drug descriptor (or predictor) values (distances between atom class pairs). A nodal tree generated by such a training set, is then used to predict the potencies of other drugs based solely on the other drugs' descriptor values (distances between atom class pairs). It is possible to use such a predictive capability to greatly increase the yield or "hit rate" in high-throughput screening (HTS).

In addition, versions of the invention generate a second nodal tree using a "validation set" of compounds. The compounds in the validation set were not present in the original training set, but also have known potencies. By confirming that the first and second nodal trees are essentially the same (from a statistical standpoint), the first (training set) nodal tree is statistically validated. Such a validation procedure tends to confirm the statistical reliability of drug potency prediction made using the original training set tree.

This sales brochure also illustrates a version of the invention's capability to display actual relevant molecular structures (see screenshot, p. 12 and 13 of the brochure). Versions of the invention allow a user to click on a node and visualize the compounds therein. Versions of the invention highlight the structural features that lead to compound potencies in a node. Versions of the invention display other types of molecular structure representations. The similar such display of any molecular structure representation is a version of the invention. (These examples are of course nonlimiting. Other versions of the invention use one or more molecules or compounds that are not drugs, and use one or more properties that are not drug potency.)

Versions of the invention use human interaction/intervention as a part of growing one or more nodal trees. Such user interaction/intervention includes the selection of compounds for study, selection of molecular properties for study, selection of molecular descriptors (or predictors), selection of one or more stop criteria to terminate tree growth.

Versions of the invention also make use of molecular descriptors (or predictors) that are not geometry-based molecular descriptors in combination with one or more geometry-based molecular descriptors. Such versions of the invention group molecular data objects into nodes (or groups) that are similar in terms of both geometry-based and non geometry-based molecular descriptors (or predictors). Molecular descriptors (or predictors) and other types of descriptors (or predictors) are given in published PCT application (1) PCT/US98/07899, as well as published papers (2) Hawkins, et. al., Analysis of Large Structure-Activity Data Set Using Recursive Partitioning, Quant. Struct.—Act. Relat. 16, 296-302 (1997). (3) Rusinko, et. al., Analysis of a Large Structure/Biological Activity Data Set Using Recursive Partitioning, J. Chem. Inf. Comput. Sci. 1999, 39, 1017-1026 and the two sales brochures. References (1), (2) and (3) of the preceding sentence are incorporated herein by reference to the fullest extent of the law.

Other Examples of Real-World Data or Real-World Data Objects that are Handled by Versions of the Invention Versions of the invention handle other kinds of real world data. Examples: (1) in oil exploration: Well logs. The measures (descriptor(s) or response(s))are physical and electrical properties of the rock measured at increasing depths. A segmentation into sections of comparable physical and electrical properties yields estimates of the subsurface stratigraphy. Hawkins and Merriam, Mathematical Geology, 1974 (which is incorporated herein by reference, see ref. 5 in endnotes). (2) In mining or geology Transects across fields. The measurements (descriptor(s) or response(s)) are soil composition. A segmentation gives rise to maps showing different types of soil. (Webster, Mathematical Geology early 1970s and see ref. 1 in endnotes which are incorporated herein by reference.) (3) market segmentation research. The measures (descriptors/predictors) are demographic and the dependent (response) is the propensity to take a particular action—for example to purchase a boutique coffee. Fitting the recursive partitioning model will then lead to identification of market segments, along with the size and demographic characteristics of each segment. Any marketing use that is similar and known in the field of marketing is also a version of the invention. (4) credit card scoring: The dependent variable is a borrower's history of responsible use of credit. The explanatory variables are demographic and financial characteristics of the borrower. The object is to find valid credit scores. Any credit use that is similar and known in the field of credit is also a version of the invention. (5) demographic tax studies: The dependent variable is a measure of tax compliance. The predictors are characteristics of the tax form. The purpose is identification of forms likely to be non-compliant. (A student of Prof. Hawkins did an MS thesis research project on this topic. An official copy of the thesis is with the Univ. Minnesota library and is incorporated herein by reference. The student is David McKenzie, who graduated in 1993 and his thesis applied FIRM to Minnesota Department of Revenue tax returns.) Any tax use that is similar and known in the field of revenue is also a version of the invention. Other example applications are in U.S. Pat. Nos. 4,719,571; 5,787,274; 6,182,058; 6,434,542, U.S. patent publication T998008, book Recursive Partitioning in the Health Sciences by Zhang and Singer, 1999 Springer-Verlag. Each of these is incorporated herein by reference to the fullest extent of the law.

Hardware

For the present invention described in this application, versions of the invention and computer-based methods described herein are not limited as to the type of computer on which they run. The computer typically includes a keyboard, a display device such as a monitor, and a pointing device such as a mouse. The computer also typically comprises a random access memory (RAM), a read only memory (ROM), a central processing unit (CPU) and a storage device such as a hard disk drive, floppy disk drive or CD-ROM. It possible for the computer to comprise a combination of one or more of these components as long as such combination is operable and not mutually exclusive. For example, multiple processors are possible; or a device that functions in place of a keyboard is possible; or the keyboard is eliminated in some versions; or more peripheral storage devices such as a floppy drive or CD-ROM are eliminated. Another way to describe components of such a typical computer is processor means (or component), memory means (or component), display means (or component), pointing means (or component), peripheral memory means (or component). An Input/Output means (or component) is part of some versions of such a computer. However, as stated above, such a typical computer is described only as an example. And these examples are not limiting. And in general, versions of the invention run on any general purpose digital computer. Versions of the invention run on platforms such as Windows NT/95/98, Linux; and UNIX variants.

A Note on Data Handled

Versions of the invention handle data that is partly real world and partly simulated, e.g (1) one or more data objects real-world, one or more data objects abstract; (2) one or more descriptor values or one or more property values simulated and one or more descriptor values or one or more property values real. Other similar combinations are possible.

Genetics/Pharmacogenomics

Also included with U.S. provisional patent application 60/225,113 which is a priority document for this application is the sales brochure: "Is your company taking advantage of the revolution in pharmacogenomics?" by Golden Helix, Inc. This brochure illustrates and describes one or more versions of the invention that use segmenting algorithms or recursive partitioning (or both) in the field of genetics or pharmacogenomics. This brochure is incorporated herein by reference to the fullest extent of the law. In such a genetics or pharmacogenomics context, an example of a data object is an individual creature, such as a human being. Another example of a data object is tissue from a creature. In such a context an example of a property is a phenotypic characteristic of a creature. A description (or descriptor) of a genetic makeup (of a creature) includes, but is not necessarily limited to, (1) a combination of one or more genotypes at one or more polymorphisms (2) a combination of one or more alleles at one or more polymorphisms and (3) a combination of one or more haplotypes (4) a combination of two or more of (1), 2, or (3). An example of a property is a phenotypic characteristic A phenotypic characteristic includes (but is not limited to) positive or negative drug response. A phenotypic characteristic is an observable or inferable inherited genetic characteristic or inherited genetic trait including a biochemical or biophysical genetic trait, for example an inherited disease is a genetic characteristic, a predisposition to an inherited disease is a genetic characteristic. A phenotypic characteristic, phenotypic property or character is a genetic characteristic. The distinction between a phenotypic characteristic and a genetic descriptor is somewhat arbitrary. The above terms (such as descriptor, property, data object, creature, phenotype, genetic make-up, tissue) to describe versions of the invention, include any similar or equivalent term known to those of ordinary skill in genetics or pharmacogenomics. Such terms including any term which is essentially a descriptor, property, creature, data object, tissue in any phase of the pharmaceutical industry.

A biological property or characteristic, or an observable or inferable characteristic including a biochemical or biophysical characteristic is used by versions of the invention to characterize (using a descriptor or property value) a creature, tissue from creature.

Unless specifically stated otherwise some embodiments of each version of any process or apparatus that segments data described herein output data in segmented form (1) to a monitor, LCD, CRT, printer or equivalent device for use by a human user or users or (2) to a memory device such as a hard drive or (3) for sending over media such as the internet. Any computer-based method (or apparatus) that uses data in segmented form from a version of the invention (or equivalent invention) described herein, wherein the method essentially outputs data to a monitor or equivalent device is a version of the invention. Any apparatus that practices any process described herein that is a version of the invention is also a version of the invention.

Any data structure described herein or generated by any version of the invention (either during its operation or essentially as an end result) described herein is a version of the invention. A data structure or other version of the invention described herein that is on a computer readable medium such as a CD-ROM, flash ROM, RAM, hard drive or embedded in a computer readable transmission signal (ie electromagnetic or optical) is a version of the invention. The data in some data structures generated by versions of the invention, such as nodal trees, hierarchies of candidate score values, or during the calculation of best score subsets are functionally interrelated and also essentially require processing by a computer.

Versions of the invention that are similar to versions described herein operate by sending or receiving (or both) information (including over media such as the Internet). Versions of the invention are any one process described or claimed herein, wherein the process comprises sending or receiving information in one or more steps, step-like parts or parts of the process. And any apparatus that practices such a process is a version of the invention.

Scope of the Invention

It is generally possible for any process described herein which handles real-world data to be practiced with an additional (further included) step or step-like part of data gathering or collection, such as actual physical collection. And such a process is also a version of the invention. All the features disclosed in this specification (including any claims and drawings), and one or more of the steps of any method or process so disclosed, may be used in any combination, except combinations where at least some of such features and/or steps are mutually exclusive. Each feature disclosed in this specification (including any claims and drawings), may be replaced by alternative features of the same, equivalent or similar purpose, unless expressly stated otherwise. Thus, unless expressly stated otherwise, each feature disclosed is one example only of a generic series of equivalent or similar features.

While the description contains many specificities these represent exemplifications of versions of the invention and do not limit the scope of the invention. Therefore the reader's attention should also be directed to the claims and their legal equivalents and to equivalent versions of the invention not specifically described.

Versions of the invention illustratively disclosed herein suitably may be practiced in the absence of any element which is not specifically disclosed herein. Versions of the present invention illustratively disclosed herein suitably may be practiced wherein one or more of the terms "comprising", is replaced by one or-more of "consisting", "consisting essentially", or "consisting predominantly". The references in the endnotes are incorporated herein by reference to the fullest extent of the law. [10]

Technical Field Versions of the invention have applications in many areas, including analysis of real-world data. Some versions are specifically in the area of high-throughput screening of pharmaceuticals. Some versions are applicable in pharmacogenomics. Some versions are applicable in mining, marketing studies, and other applied areas.

DPSA Appendix: DPSAs and Fast Segmenting Algorithms

Professor Douglas Hawkins has worked in the field of segmenting data using statistical and computational methods for many years. Professor Hawkins discovered an important segmenting algorithm many years ago.[11] The algorithm is an $O(n^2)$ dynamic programming algorithm to find the optimal cutpoints for a set of segments [see references]. This algorithm, while much faster than an exhaustive search (or computation), nevertheless can run very slowly when segmenting large quantities of data. (An algorithm that runs in time $O(n^2)$ is one where the time to solve the problem is proportional to the square of the input size.)

Embodiments of our methodology (Fast Segmenting Algorithms) run in time proportional to $O(n^{1.5})$, $O(n \log n)$, or even $O(n)$. When performing segmenting on real world data, our algorithms can make the difference between solving a problem in seconds instead of hours.

We first describe the Hawkins algorithm by way of illustration in order to teach versions of the invention (Fast Segmenting Algorithm). The basic principle behind dynamic programming is that partial solutions of a problem that have been computed earlier can be stored and used later in the computation to reduce the amount of time spent. Hawkins uses this principle in his algorithm.

Hawkins's Dynamic Programming (DP) Algorithm to Find Optimal Segmentation of a Group of Data Points Discrete Data Points (or Values) in a Sequential Order.

Let $y_1, y_2, y_3, \ldots, y_{n-2}, y_{n-1}, y_n$ be a group of n discrete data values or data points. (It is also possible to speak of these n discrete data values (or points) as a vector of data, wherein the vector has length n. And it is also possible to speak of these n discrete data values as vector y.)

"Segmenting" Such a Group of Points into Nonoverlapping "Segments".

It is possible to subgroup these n data points into k segments ($k \leq n$), so that each of the n data points belongs to one and only one segment. This process of "segmenting" the n data points into k segments is a process of forming k disjoint subgroups of contiguous points. (These k segments are referred to herein as a k-way split or k segment covering. An alternative expression is a k-segment segmentation.)

Segmenting in Such a Way that the Data Points within each Segment are Homogeneous.

It is possible to segment a group of sequential data points into k segments many ways. (In particular there are $C(n, k-1) = n!/[(n-k+1)!(k-1)!]$ possible coverings of n data points into k segments.) However, it is a goal of a segmenting algorithm (or segmentation process) that the points within each segment be essentially similar in value or homogeneous. Thus a segmenting algorithm essentially chooses (or prefers) only coverings for which the data points within each segment are essentially homogeneous (in value).

A Measure of Data Point Segment Homogeneity: the Sum of Squared Deviations of the Data Points within the Segment about their Mean.

To achieve the goal homogeneity of data points within each segment of a covering, Hawkins chooses a measure of the homogeneity of the data values within each segment (for a possible covering). The measure of homogeneity used for any one segment is the sum of squared deviations of the data points within the segment about their mean. Let $1 \leq i \leq j \leq n$.

For a segment corresponding to points $i, i+1, j-1, j$, the mean of the data values within the segment is given by $$\bar{y}_{i,j} = \frac{\sum_{m=i}^{j} y_m}{j-i+1} \sum_{m=i}^{j} y \quad \text{Equation 1}$$

And the measure of homogeneity (the sum of squared deviations of the data points within the segment about their mean) is denoted as $r(i, j)$.

$$r(i, j) = \sum_{m=i}^{j} (y_m - \bar{y}_{i,j})^2 \quad \text{Equation 2}$$

The measure of homogeneity, $r(i, j)$, is a low value if the segment is homogeneous (i.e. if the data point values $y_i, y_{i+1}, \ldots, y_{j-1}, y_j$ are similar or homogeneous). The measure $r(i,j)$ is the score function for a segment.

Summing all of the $r(i, j)$ for a Covering Gives a Measure of Overall Homogeneity for the Covering.

By adding all the $r(i,j)$ values for a covering, a measure of the overall homogeneity of the data points within each segment (of the covering) is obtained. Denoting the data points within the k segments of a covering as the values from 1 to $n_1$, $n_1+1$ to $n_2, \ldots, n_{k-1}$ to n; an overall measure W, of the homogeneity of the segments (of the covering) is given by $W=r(1, n_1)+r(n_1+1, n_2)+ \ldots +r(n_{k-2}+1, n_{k-1})+r(n_{k-1}+1, n)$. Small values of W then correspond to higher degrees of homogeneity within the segments (of a covering). With such a strategy, an appropriate choice of segments (for a covering) is to choose values of $n_1, n_2, \ldots, n_{k-1}$ for which W is minimized. The overall measure W is the score function for a split or covering. Hawkins then proceeds to show how to find such an optimal set of k segments by using a dynamic programming computer algorithm.[12]

Hawkins's Dynamic Programming (DP) Algorithm for Finding an Optimal Covering of n Data Points Using k Segments.

Hawkins's algorithm is based on the following principle. Given n data points, and an optimal covering using k segments (or a best k-way split), the last endpoint (or cutpoint) of the covering is $n_{k-1}+1$. Since this k-segment covering is an optimal covering for the data points from 1 to n, it follows that this covering is composed of an optimal k-1 segment covering for the data points from 1 to $n_{k-1}$, plus the last segment covering points $n_{k-1}+1$ to n.[13] Thus if the optimal k-1 segment coverings for data points 1 to m, for each point m, $1 \leq m \leq n$ is known, then it is easy to find the optimal k segment coverings for the data points from 1 to n. This is done using a simple search.

Simple Search for Finding the Optimal K-Way Splits when the Optimal (k-1)-Way Splits are known.

The simple search is done as follows. Let the point m be the last data point in a series of points 1 to m. Let $F_{k-1}(m)$ be defined as the measure W (or score) for an optimal (k-1)-way split for the points from 1 to m. (W is then a minimum.) Similarly let $F_k(n)$ be the measure W (or score) for an optimal k-way split for the data points 1 to n. It follows that $F_k(n)=\min \{F_{k-1}(m)+r(m+1,n)\}$ for $k-1 \leq m \leq n$. The simple search is done by calculating the n−k values of $F_{k-1}(m)+r(m+1,n)$ for each value of m from k−1 to n and finding the minimum or minima.

Using the Simple Search Recursively Leads to an Algorithm for Finding the Optimal K-Way Split for Data Points 1 to n.

As we have seen above, the optimal k-way splits coverings can be deduced from the optimal k−1 splits using a simple search. Since 1 way splits are unique, the optimal 2 way splits are deduced from them. And the optimal 3 way splits are deduced from the optimal 2 way splits. Applying this process recursively, the optimal k-way splits are finally deduced from the optimal (k−1)-way splits. This then is essentially Hawkin's algorithm.

Formal Presentation of Hawkins's DP Algorithm

Using the ideas presented above, Hawkins formally presents his algorithm.[14] Algorithm: Let $F_j(m)$ be the measure W (within segment sum of squared deviations) for an optimal j-way split for the data points 1 to m. Then $F_1(m)=r(1,m)$ for m=1, 2, . . . , n. And, $F_j(m)=\min\{F_{j-1}(v)+r(v+1, m)\}$, $j-1 \leq v \leq m-1$. Computational tables of $F_j(m)$ are generated for m=1 to n and j=1, 2, 3, k. The value of W for an optimal k-way split on n data points is $F_k(n)$ and $F_k(n)$ is deduced as described above. The boundaries of the optimal segments are deduced from a "traceback" procedure. Similar algorithms are also presented.[15]

Segmenting with Missing or "Float" Values

Musser's thesis describes how to handle missing values within Hawkin's DP. It is often the case with real-world data that descriptors will take on missing or "floating" values. In this case, it is still possible to segmenting using the missing values as predictors. The missing values can either be put in their own segment, or grouped with one of the other segments. The choice of which segment the missing cases should be put with is done so as to maximize a measure r(i,j) of segment homogeneity. We can define a function $F^*_k(m)$ that gives the optimal measure for a k-way split that includes missing values, and $r^*(i,j)$ as the measure for a segment containing data values $y_i$ through $y_j$ with missing values placed within that segment. Then the recursion becomes $$F^*_j(m) = \min\begin{cases}\min\{F^*_{j-1}(v)+r(v+1,m)\}, j-1 \leq v \leq m-1 \\ \min\{F_{j-1}(v)+r^*(v+1,m)\}, j-1 \leq v \leq m-1\end{cases}$$

The top part of the equation puts the missing values somewhere among the segments in the left half of the data. The latter puts the missing values with final segment. The case where the missing values are all alone would be where $r^*(v+1,m)$ is empty and only missing values are contained in that segment. Operationally, one must tabulate separately Fj's and F*j's in order to handle missing values.

A more Detailed Examination of Hawkins's Algorithm.

To better understand the Hawkins DP algorithm, the following table is presented that illustrates the workings of the algorithm. (There is no such actual pictorial table in Hawkins's published papers on this topic.) This table illustrates the tabulation of values of $F_j(m)$ that are generated for m=1 to n and j=1, 2, . . . , k by the algorithm. In this illustration we essentially diagram the process of obtaining the tables of values of $F_j(m)$ in a pictorial form.

By making the pictorial table, we diagram the process so it can be further understood. First we compute a vector that has in positions 1 . . . n the values for $F_1(1), F_1(2) \ldots F_1(n)$. Then we compute $F_2(2), F_2(3) . F_2(n)$ in terms of $F_1(1), F_1(2) \ldots F_1(n)$. We continue this process up until k=4 segments, depicted in the following table. (Such a table is exemplary, nonlimiting and merely illustrative and can be drawn for any value of k.) The table, Table 1, is given on the following page.

TABLE 1

|  | F(1) | F(2) | F(3) | F(4) | F(5) | ... | F(n) |
|---|---|---|---|---|---|---|---|
| $F_1()$ | r(1, 1) | r(1, 2) | r(1, 3) | r(1, 4) | r(1, 5) | ... | r(1, n) |
| $F_2()$ | 0 | $F_2(2)$ = $F_1(1) + r(2, 2)$ | $F_2(3)$ = min $\{F_1(1) + r(2, 3),$ $F_1(2) + r(3, 3)\}$ | $F_2(4)$ = min $\{F_1(1) + r(2, 4),$ $F_1(2) + r(3, 4),$ $F_1(3) + r(4, 4)\}$ | $F_2(5)$ = min $\{F_1(1) + r(2, 5),$ $F_1(2) + r(3, 5),$ $F_1(3) + r(4, 5),$ $F_1(3) + r(5, 5)\}$ | ... | $F_2(n)$ = min $\{F_1(1) + r(2, n),$ $F_1(2) + r(3, n),$ $F_1(3) + r(4, n),$ $F_1(3) + r(5, n),$ . . . $F_1(n-1) + r(n, n)\}$ |
| $F_3()$ | 0 | 0 | $F_3(3)$ = min $\{F_2(2) + r(3, 3)\}$ | $F_3(4)$ = min $\{F_2(2) + r(3, 4),$ $F_2(3) + r(4, 4)\}$ | $F_3(5)$ = min $\{F_2(2) + r(3, 5),$ $F_2(3) + r(4, 5),$ $F_2(4) + r(5, 5)\}$ | ... | $F_3(n)$ = min $\{F_2(2) + r(3, n),$ $F_2(3) + r(4, n),$ $F_2(4) + r(5, n),$ . . . $F_2(n-1) + r(n, n)\}$ |
| $F_4()$ | 0 | 0 | 0 | $F_4(4)$ = min $\{F_3(3) + r(4, 4)\}$ | $F_4(5)$ = min $\{F_3(3) + r(4, 5),$ $F_3(4) + r(5, 5)\}$ | ... | $F_4(n)$ = min $\{F_3(3) + r(4, n),$ $F_3(4) + r(5, n),$ . . . $F_3(n-1) + r(n, n)\}$ |

The zeros in the table are where it is impossible to have a k-way split when there are only k−1 or less data points. The score for the optimal 4-way split is given by $F_4(n)$, which is the bottom rightmost entry in the table. The actual positions where the splits occur can be traced if you keep an additional table of the position where the minimum value occurred for each cell in the table. The algorithm is $O(kn^2)$. For a given row past the first row, the rightmost column takes the minimum of n−1 items, the next to the left takes n−2, so on down to zero.

The running time for a given row is thus given by $O(n^2)$. Because there are k rows for a k-way split, and it costs $O(n^2)$ to compute the entries for a row, the total running time is thus $O(kn^2)$.

Fast Segmenting Algorithm Description

By drawing the computations for the Hawkins $O(n^2)$ in a tabular form, it is possible to make some novel observations about the computation, and derive new faster algorithms. Consider the cells that compute the values for $F_3(4)$ and $F_3(5)$. The first element (or candidate score) of the minimum for these two rows is given by $F_2(2)+r(3,4)$ and $F_2(2)+r(3,5)$ respectively. Suppose that $F_2(2)+r(3,5)$ was the lowest score for that cell. It does not follow that $F_2(2)+r(3,4)$ will be the lowest score for its cell, but because the score computation differs only by a single element (or data point, $y_5$), and the same element (or data point or observation) is removed from the score of each potential minimum in the cell, it is reasonable to expect that it will be among the lowest scores for its cell. This is a key concept. (The values $F_2(2)+r(3,5)$ and $F_2(2)+r(3,4)$ are equal level candidate values of adjacent cells of a row in the table. These two values differ only by the data point $y_5$. $F_2(2)+r(3,5)=C_3(2,5)$ and $F_2(2)+r(3,4)=C_3(2,4)$, see definitions section for more on candidate values and equal level candidate values.)

If we can take the smallest c scores for the rightmost cell in a row, if c is sufficiently large, we are guaranteed with high certainty that the minimum score in the next column to the left will be among those c scores, adjusted to remove the observation (or data point) dropped out of the cell to the left. Furthermore, if c is sufficiently large, we are likely to find the best score for subsequent columns among those c scores. However, because we drop an observation (or data point) each time, thus changing the score a bit each time, we will eventually have to recompute a new set of scores from scratch. These ideas lead to the following new algorithms.

FSA TEACHING EXAMPLE 1

1. Compute $F_1(1) \ldots F_1(n)$ in $O(n)$ time using a cumulative sum.
2. Compute $F_2(n)$, saving the best $\sqrt{n}$ scores. Computing the smallest $\sqrt{n}$ elements of an n element vector can be done in $O(n)$ time. This is done with a selection algorithm (or similar algorithm, or one or more algorithms that achieve essentially the same result) in $O(n)$ time, see chapter ten of reference Cormen (1990).
3. Compute $F_2(n-1)$ by removing the observation from the $\sqrt{n}$ best scores, and computing the minimum of those updated scores. This can be done in $\sqrt{n}$ time. Repeatedly do this updating procedure to compute $F_2(n-2) \ldots F_2(n-\sqrt{n})$.
4. At this point as in step 2, we go through all of the approximately $n-\sqrt{n}$ scores and save the smallest $\sqrt{n}$ scores. Then as in step 3, compute the next $\sqrt{n}$ entries of the table using the updating procedure.
5. Repeat steps 3 and 4 $\sqrt{n}$ times until all entries in the row have been computed.
6. We have now computed $F_2(1) \ldots F_2(n)$. We can repeat the same steps 2 through 5 to compute $F_3(1) \ldots F_3(n)$, and so on up until we have computed k rows of the table to find the best k-way split.

The running time of this algorithm is $O(n\sqrt{n})=O(n^{1.5})$. It costs us $O(n)$ steps to compute a subset. We compute a subset $\sqrt{n}$ times, giving a running time of $O(n\sqrt{n})$. We also do an updating procedure on $\sqrt{n}$ items n times, giving a running time of $O(n\sqrt{n})$.

Versions of the invention take smaller subsets, and recompute less frequently. This speeds up the algorithm, possibly at the expense of giving less optimal splits. Another embodiment of the invention that runs faster but has a higher chance of giving suboptimal splits is as follows.

FSA TEACHING EXAMPLE 2

1. Compute $F_1(1) \ldots F_1(n)$ in $O(n)$ time using a cumulative sum.
2. Compute $F_2(n)$, saving the best log n scores. This is done with a randomized selection algorithm (or similar algorithm, or one or more algorithms that achieve essentially the same result) in $O(n)$ time.
3. Compute $F_2(n-1)$ by removing the observation from the log n best scores, and computing the minimum of those updated scores. This can be done in log n time. Repeatedly do this updating procedure n/log n times to compute $F_2(n-2) \ldots F_2(n-(n/\log n))$.
4. At this point as in step 2, we go through all of the approximately $n-(n/\log n)$ scores and save the smallest log n scores. Then as in step 3, compute the next n/log n entries of the table using the updating procedure.
5. Repeat steps 3 and 4 log n times until all entries in the row have been computed.
6. We now have computed $F_2(1) \ldots F_2(n)$. We can repeat the same steps 2 through 5 to compute $F_3(1) \ldots F_3(n)$, and so on up until we have computed k rows of the table to find the best k-way split.

The running time of this algorithm is $O(n \log n)$. It costs us $O(n)$ steps to compute a subset. We compute a subset log n times, since we recompute every n/log n steps. We also do an updating procedure on log n items n times.

FSA TEACHING EXAMPLE 3

1. Compute $F_1(1) \ldots F_1(n)$ in $O(n)$ time using a cumulative sum.
2. Compute $F_2(n)$, saving the best $c_1$ scores, where $c_1$ is a constant. This is done with a randomized selection algorithm (or similar algorithm, or one or more algorithms that achieve essentially the same result) in $O(n)$ time.
3. Compute $F_2(n-1)$ by removing the observation from the $c_1$ best scores, and computing the minimum of those updated scores. This can be done in constant time. Repeatedly do this updating procedure $n/c_1$ times to compute $F_2(n-2) \ldots F_2(n-(n/c_1))$.
4. At this point as in step 2, we go through all of the approximately $n-(n/c_1)$ scores and save the smallest $c_1$ scores. Then as in step 3, compute the next $n/c_1$ entries of the table using the updating procedure.
5. Repeat steps 3 and 4 $c_1$ times until all entries in the row have been computed.
6. We now have computed $F_2(1) \ldots F_2(n)$. We can repeat the same steps 2 through 5 to compute $F_3(1) \ldots F_3(n)$, and so on up until we have computed k rows of the table to find the best k-way split.

The running time of this algorithm is $O(n)$. It costs us $O(n)$ steps to compute a subset. We compute a subset a constant $c_1$ times, since we recompute every $n/c_1$ steps. We also do an updating procedure on $c_1$ items n times.

Alternate embodiments of the invention take various subset sizes and recompute the subset at various intervals. Rather than having subset sizes of exactly $\sqrt{n}$, it is desirable in some cases to take some constant factor multiplied by $\sqrt{n}$. Similarly this is the case with the other quantities. As is well known in analysis of algorithms, changing these constant factors will not change the overall asymptotic functional form of running time of the algorithm. However, it could have large consequences in the actual time spent, and on the optimality of the solution.

Reference: Cormen, T. H.; Leiserson, C. E. and Rivest, R. L. (1990) *Introduction to Algorithms,* Cambridge, Mass.: The MIT Press.

Versions of fast segmenting algorithms are described above. The use of a computer-based method that uses one or more of these algorithms (or similar algorithms) to segment data objects, including data objects that represent real world objects is a version of the invention. Any invention, process or apparatus, or similar entity that includes one or more of these (or similar) algorithms is a version of the invention.

Versions of the fast segmenting algorithm calculate by adding or removing an observation from a cell using techniques of "running sums", a well known technique in computer science. Versions of the invention (algorithm) described above compute F values in each of the cells of the table by following a certain "path" of computation. This path computes $F_1()$ values first, then down to the rightmost cell in the second row and backwards. Other versions of the invention follow different computational paths to calculate F values. For example, a version calculates $F_1()$ values first, then calculates $F_2()$ values for an interior cell first (saving the best c scores), and then follows a path to the right and to the left along the second row computing c $F_2()$ scores for second row cells. Similar variations of the computational path described above are followed by various versions of the invention to compute all or essentially all cells in the table.

Some such versions recompute all or essentially all the scores in a cell at various intervals as described above. Some versions of the invention do not recompute all or essentially all scores in a cell at periodic intervals or any interval. Versions of the invention are operable and have utility for score functions, deviance measures, statistical measures of homogeneity or equivalent measures other than the sum of squares type score function described above. These include measures of homogeneity or equivalent measures similar to those discussed in references 1-9.

General Definitions

Some concepts behind versions of Fast Segmenting Algorithms have been described above, general definitions are given here to allow a more general description of versions of the invention (Fast Segmenting Algorithms).

General definition of a measure of segment homogeneity, r(i, j), (measure of homogeneity of data points within a segment. Let $y_1, y_2, y_3 \ldots, y_{n-2}, y_{n-1}, y_n$ be a group of n discrete data values or data points in a sequential order. And let $1 \leq i \leq j \leq n$. For a segment corresponding to points i, i+1, ..., j-1, j. Specific examples of a measure of segment homogeneity include (1) sum of squared deviations of the data points within the segment about their mean, (2) sum of the absolute values of the deviation of each data point within the segment from the within segment data point mean, (3) a measure of the variance of the data points within the segment. Other examples are given in equations 3 and 4 below, wherein z is a positive number. The values 1 and 2 are preferred values for z.

$$r(i, j) = \sum_{m=i}^{j} |(y_m - \bar{y}_{i,j})|^z \qquad \text{Equation 3}$$

$$r(i, j) = z\sqrt{\sum_{m=i}^{j} |(y_m - \bar{y}_{i,j})|^z} \qquad \text{Equation 4}$$

$$\bar{y}_{i,j} \cong \frac{\sum_{m=i}^{j} y_m}{j - i + 1} \qquad \text{Equation 5}$$

In equation 5, the mean is an exact or approximate mean.

Versions of the invention segment responses $y_i$ that are from a binomial distribution, where there are only two possible values that the $y_i$ responses can take. Let us denote these values as zero (0) or one (1). Then a measure of segment homogeneity that is preferred for versions of the invention that use binomial responses is given by equation 6.

$$r(i,j) = -2(j-i+1)(\bar{y}_{i,j}\log(\bar{y}_{i,j}) + (1-\bar{y}_{i,j})\log(1-\bar{y}_{i,j})) \qquad \text{Equation 6}$$

Multivariate Versions of the Invention

Up until now, we have considered the cases where $y_i$ are univariate values. Versions of the invention use multivariate or vector valued responses, where we have a sequence of p-component multivariate vectors $Y_i$, i=1, 2, ..., n. Measures of homogeneity between vector-valued responses known to a person of ordinary skill in statistics define versions of the invention. One such measure of homogeneity is the Pillai-Bartlett-Nanda trace (or Pillai trace for short) statistic. Define the mean vector of the multivariate vectors as:

$$\bar{Y}_{i,j} = \frac{\sum_{m=i}^{j} Y_m}{j - i + 1}. \qquad \text{Equation 7}$$

Define the total sum of squares and cross-products matrix as:

$$S = \sum_{m=1}^{n} (Y_m - \bar{Y}_{1,n})(Y_m - \bar{Y}_{1,n})^T. \qquad \text{Equation 8}$$

Then the following multivariate segment homogeneity measure defines a version of the invention that operates on multivariate responses:

$$r(i, j) = \text{trace}\left(S^{-1/2} \sum_{m=i}^{j} (Y_m - \bar{Y}_{i,j})(Y_m - \bar{Y}_{i,j})^T (S^{-1/2})^T\right) \qquad \text{Equation 9}$$

The matrix inverse square root of S serves to standardize the data, and the trace of the matrix gives a single number as a value for r(ij), allowing us to use the rest of the dynamic program unaltered. This measure of homogeneity is most appropriate when the data vectors are essentially normally distributed. When the data vectors are binary, then a more appropriate statistic is to use a higher dimensional analog of equation 6. If the vector is p-dimensional, we simply sum up the one-dimensional r(ij) measures for each dimension of the vector. Other measures known by a person of ordinary skill in statistics may be used to test for segment homogeneity, including the Hotelling T_0 squared statistic.

Other examples of a measure of segment homogeneity is any function that is a monotonic or essentially monotonic function (including linear or essentially linear function) of any one of the above described measures of segment homogeneity. Also any measure of segment homogeneity known to a person of ordinary skill in statistics or the segmenting of data by statistical or computational methods is an example of an segment measure of homogeneity.

General definition of a measure of overall homogeneity, $W^*$, of a covering of s segments (or an s-way split or segmentation) of d consecutive data points. By adding all the $r(i,j)$ values for a covering, a measure of the overall homogeneity of the data points within each segment (of the covering) is obtained. Denoting the d data points within the s segments of a covering as the values from 1 to $n_1$, $n_1+1$ to $n_2$, ..., $n_{k-1}$ to n; an overall measure $W^*$, of the homogeneity of the segments (of the covering) is given by $W^* = r(1, n_1) + r(n_1+1, n_2) + \ldots + r(n_{k-2}+1, n_{k-1}) + r(n_{k-1}+1, n)$. Preferred measures of overall homogeneity $W^*$ is any measure derived from a preferred measure of segment homogeneity (such as sum of squared deviations or sum of absolute value deviations type measures). Other examples of a general overall measure of homogeneity of a covering is any function that is a linear or essentially linear function of any one of the above described $W^*$. Also any measure of overall homogeneity of a covering known to a person of ordinary skill in statistics or the segmenting of data by statistical or computational methods is an example of a measure of overall segment homogeneity. Smaller values of $W^*$ correspond to higher degrees of homogeneity within the segments (of a covering) for some measures $W^*$. (It is also possible for larger values of $W^*$ to correspond to higher degrees of homogeneity within the segments (of a covering) for some measures $W^*$.)

Let $F_{k,W^*}(n)$ be the value of $W^*$ for an optimal k-way split for the data points 1 to n for some measure $W^*$. ($W^*$ is then a maximum or a minimum.)

A computational segmenting table is a nonlimiting pictorial characterization of the operation of a segmenting algorithm that finds a k-way split of n sequential data points ($y_1$, $y_2$, ..., $y_n$). Splits found by such a segmenting algorithm include definite optimal, approximate definite optimal, probable optimal, approximate probable optimal and statistically meaningful k-way splits. (In some cases an algorithm finds other types of splits.) Table 1 is an example of a computational segmenting table.

A computational segmenting table is similar to a matrix in format, with one or more rows and one or more columns. Each computational segmenting table has a value for $F_j(m)$, for a pair of values of j and m, wherein $1 \leq j \leq k$, $1 \leq m \leq n$. Each pair j, m) corresponds to a cell in the table. For a given pair and cell, j corresponds to the row number and m corresponds to the column number of the cell. For each computational segmenting table, $F_j(m)$ is an overall homogeneity score function value for a j-way split of m sequential data points ($y_1, Y_2, \ldots y_m$); or $F_j(m)$ does not correspond to a split and the value of $F_j(m)$ is "undetermined".

For each computational segmenting table, each $F_j(m)$ corresponds to one and only one cell of the table. The value $F_j(m)$ for any one cell is "elected" from the set or a subset of "candidate scores" for the cell. The value of $F_j(m)$ for any one (or each) cell of the table is the elected score value for the (or each) cell. So, $F_j(m)$ is the elected score value for the cell (to which $F_j(m)$ corresponds).

Election of an $F_j(m)$ Value to be the Elected Value for a Cell of a Computational Segmenting Table.

For each computational segmenting table, each $F_j(m)$ corresponds to one and only one cell of the table. Each segmenting algorithm determines a value of $F_j(m)$ for each cell of a table that characterizes the algorithm. Each value of $F_j(m)$ is determined (or elected) so that each value of $F_j(m)$ is (1) a (definite) optimal score value, (2) an approximate (definite) optimal score value, (3) a probable optimal score value, (4) an approximate probable optimal score value, or (5) a statistically meaningful value (a value that corresponds to a statistically meaningful split). If $F_j(m)$ is not reliably or reasonably described by one (or more) of the categories (1) through (5), then $F_j(m)$ does not correspond to a split and $F_j(m)$ is assigned the value (6) "undetermined".

Each of the categories (1)-(6) in the above paragraph is an election category. For each value of $F_j(m)$, the election category of any one $F_j(m)$ is the lowest number category (1)-(6) which reliably or reasonably describes the $F_j(m)$. Put another way, the election category of each $F_j(m)$ is the lowest number category (1)-(6) which reliably or reasonably describes each $F_j(m)$. For example, in the Hawkins DP algorithm, $F_j(m)$ is determined using the relation $F_j(m) = \min \{F_{j-1}(v) + r(v+1, m)\}$, wherein v takes on each possible value between $j-1$ and $m-1$; ($j-1 \leq v \leq m-1$). And in the Hawkins DP algorithm, each $F_j(m)$ is a definite optimal value for its cell. In FSA Teaching Example 1, only proper subsets of candidate scores are calculated for some cells and each $F_j(m)$ of each such cell is a probable optimal value. In FSA Teaching Example 1, the set of all candidate scores is calculated for the reference cell corresponding to $F_2(n)$ and the elected value $F_2(n)$ is a definite optimal (minimal) value.

As described above, some cells of Table 1 are empty or have a "0" in them due to the fact that m<j. A cell of a computational segmenting table is always essentially empty with undetermined $F_j(m)$ value, when m<j. A cell wherein m<j is an impossible cell.

A computational segmenting table that characterizes the operation of a segmenting algorithm is a table that includes details of the operation of the algorithm to obtain each piece of information used to find the endpoints (or changepoints, or cutpoints) of each segment of the k-way split made by the algorithm.

Candidate score values of a cell of a computational segmenting table. For each computational segmenting table, each value of $F_{j-1}(v) + r(v+1, m)$ in a cell is a possible candidate score value to be the elected score value $F_j(m)$. The candidate score value $F_{j-1}(v) + r(v+1, m)$ is denoted $C_j(v,m)$. $C_j(v,m)$ is the score or score value (overall measure of homogeneity) for a j-way split on m data points ($y_1, y_2 \ldots, y_m$), wherein the last segment of the split includes only the points $v+1$ to m. $F_{j-1}(v) + r(v+1, m) = C_j(v,m)$. In FSA Teaching Example 1, the optimal candidate score for the cell that corresponds to $F_2(n)$ (in a table similar to Table 1) is chosen to be the elected score value for the cell.

The set of (all) candidate score values of a cell of a table is the set of all possible values of $C_j(v, m)$, where v takes on each value from $j-1$ to $m-1$, ($j-1 \leq v \leq m-1$).

A subset of the set of all candidate score values of a cell of a table is a set of possible values of $C_j(v, m)$, wherein v takes on one or more of the values from $j-1$ to $m-1$, ($j-1 \leq v \leq m-1$). The term a subset of the set of all candidate score values of a cell is sometimes abbreviated as a subset of possible candidate scores for a cell, subset of candidate scores for a cell, subset of all possible scores or similar language. (Unless stated otherwise, in this patent application the term subset of a set means the set itself or a proper subset of the set. A proper subset of a set is a subset (of the set) wherein at least one member of the set is not a member of the (proper) subset.)

A subset of the c best values of the set of candidate score values for a cell is a proper subset that contains the c most optimal scores of the set of all possible candidate scores (for the cell). Such a subset is a best score subset of the cell, and the number c is the size of the best score subset.

A candidate score within a cell that is a member of a selected best score subset is a best score (or best candidate score) for the cell.

A subset of c approximate best values of the set of candidate score values for a cell is a proper subset that contains c candidate scores of the cell, wherein the c scores are approximately the c most optimal scores of the set of all possible candidate scores (for the cell). Such a subset is an approximate best score subset of the cell, and the number c is the size of the approximate best score subset.

A candidate score within a cell that is a member of a selected approximate best score subset is an approximate best score (or an approximate best candidate score) for the cell.

Equal level (or same level) candidate score values of adjacent cells in a row of a computational table. In Table 1, the candidate score value expressions $F_2(2)+r(3,4)$ and $F_2(2)+r(3,5)$ are at the same level (or equal levels) of two adjacent cells in the same row of the table. ($F_2(2)+r(3,5)=C_3(2,5)$ and $F_2(2)+r(3,4)=C_3(2,4)$). Similarly, given the two candidate score values $C_j(v,m)$ and $C_j(v,m+1)$, the two candidate values are in adjacent cells of the same row. These two values are equal level values. In terms of calculation, $C_j(v,m+1)-C_j(v,m)=r(v+1, m+1)-r(v+1, m)$. So these two values differ from each other by only one data point (or observation) in the expression for r( ). That data point is $y_{m+1}$. These two values are related by the fact that it is possible to calculate each value of the pair from the other value of the pair by using the dynamic programming technique of running sums (or similar technique that performs the same function). This calculation is done by adding or removing the data point $y_{m+1}$ from the calculation. Similarly, the two candidate values $C_j(v,m-1)$ and $C_j(v,m)$ are equal level values. Each candidate value of a cell of a table has either one or two equal level candidate values in one or two adjacent cells (respectively) of the same row. Equal level value pairs in adjacent cells are related in that it is possible to calculate each value of the pair from the other value of the pair by using running sums (or a similar technique) and adding or removing the same data point from the calculation.

(see FSA Teaching Example 1 and $F_2(2)+r(3,5)=C_3(2,5)$ and $F_2(2)+r(3,4)=C_3(2,4)$ as an example of equal level candidate scores.)

Some possible routes of calculation for a candidate score value in a cell. It is possible to calculate each candidate score value $C_j(v,m)$ in different ways, using different "routes". Using the equation, $C_j(v,m)=F_{j-1}(v)+r(v+1, m)$ for example, it is possible to calculate $C_j(v,m)$ from either $C_j(v,m+1)$ or $C_j(v,m-1)$ using running sums and removing or adding a data point. Such a calculation is a horizontal calculation, in that the candidate value has been calculated from other candidates in the same row (in this case also at the same level). A horizontal calculation has a direction, to the right when a data point is added to $C_j(v,m-1)$ to obtain $C_j(v,m)$, and to the left when a data point is removed from $C_j(v,m+1)$ to obtain $C_j(v,m)$. So there are horizontal rightward and leftward calculations. Some other routes are vertical. For example, using the equation, $C_j(v,m)=F_{j-1}(v)+r(v+1, m)$, it is possible to calculate $C_j(v,m)$ when $F_{j-1}(v)$ is known by calculating $r(v+1, m)$. The direction of the calculation is downward in that $C_j(v,m)$ is calculated using $F_{j-1}(v)$ results from a row above. For example, in some preferred embodiments of a Fast Segmenting Algorithm, all values of $C_2(v,n)$ are calculated from known values of $F_1(v)$ using vertical calculations (see FSA Teaching Examples 1 and 2). In this patent application, the term FSA is sometimes used in place of fast segmenting algorithm.

Equal level (or same level) candidate score values of separated cells in a row of a computational table. As noted above, $F_2(2)+r(3,5)=C3(2,5)$ and $F_2(2)+r(3,4)=C_3(2,4)$ in Table 1 are equal level candidate scores of adjacent cells (of the same row). Similarly the candidate scores $F_2(2)+r(3,5)=C_3(2,5)$ and $F_2(2)+r(3,3)=C_3(2,3)$ in Table 1 are same level candidate scores of separated cells (of the same row). In terms of calculation, $C_3(2,5)-C_3(2,3)=r(3,5)-r(3,3)$, so these two values differ from each other by only two data points ($y_4$ and $y_5$) in the expression for r( ).

Similarly, $C_j(v,m+2)$ and $C_j(v,m)$ are same level candidate scores of separated cells. And, in terms of calculation, $C_j(v, m+2)-C_j(v,m)=r(v+1, m+2)-r(v+1, m)$. So these two values differ from each other by only two data points (or observations) in the expression for r( ). The two data points are $Y_{m+1}$ and $Y_{m+2}$. These two values are related by the fact that it is possible to calculate each value of the pair from the other value of the pair by using the dynamic programming technique of running sums (or similar technique that performs the same function). This calculation is done by adding or removing the data points $y_{m+1}$ and $Y_{m+2}$ from the calculation.

Generalizing, $C_j(v, m+g)$ and $C_j(v, m)$ are same level candidate scores of separated cells (of the same row), $g \geq 2$. These two values are related by the fact that it is possible to calculate each value of the pair from the other value of the pair by using the dynamic programming technique of running sums (or similar technique that performs the same function). This calculation is done by adding or removing the data points $y_{m+1}$, $y_{m+2}, \ldots, y_{m+g}$ from the calculation. The candidate scores $C_j(v, m-g)$ and $C_j(v, m)$ are same level candidate scores of separated cells and have equivalent characteristics in terms of calculation.

Horizontal skip calculations. As noted above, $C_j(v, m+g)$ and $C_j(v, m)$, $g \geq 2$, are same level candidate score values of separated cells. And it is possible to calculate each value of the pair from the other value of the pair by adding or removing the data points $y_m+1$, $y_{m+2}, \ldots, y_{m+g}$ from the dynamic programming (DP) calculation. Such a dynamic programming calculation does not require calculation or storage of the values $C_j(v, m+1)$, $C_j(v, m+2), \ldots, C_j(v, m+g-1)$ when calculating $C_j(v, m+g)$ or $C_j(v, m)$. Such a dynamic programming calculation essentially skips the values $C_j(v, m+1)$, $C_j(v, m+2), \ldots, C_j(v, m+g-1)$. This calculation is horizontal in orientation, but essentially skips equal level candidate score values in the calculation. Such a DP calculation is a horizontal skip calculation.

The number g−1 is the skip number of the horizontal skip calculation. For a true horizontal skip calculation, the skip number is greater than or equal to 1. The skip number is zero when a horizontal calculation calculates a candidate value using a same level candidate value in an adjacent cell. When the skip number of a horizontal calculation is zero, the horizontal calculation is a nonskip horizontal calculation. Like nonskip horizontal calculations, each horizontal skip calculation has a rightward or leftward direction. Like nonskip horizontal calculations, it is possible to use horizontal skip calculations recursively. One or more versions of FSAs use one or more horizontal skip calculations and zero or more horizontal nonskip calculations recursively.

Calculating candidate score values at an equal level of a row recursively. As described above, versions of an FSA calculate one or more candidate score values at the same level of a row by using a horizontal calculation (in one direction) recursively. Similarly versions of an FSA calculate one or more candidate score values at the same level of a row using one or more horizontal calculations (in one or both directions) recursively.

Some versions of FSAs calculate one or more same level (same row) candidate score using a horizontal nonskip calculation (in one direction) recursively. (see for example, FSA Teaching Examples 1 and 2)

The length of a recursive horizontal nonskip calculation that calculates one or more same level candidate scores in an unbroken chain of adjacent row cells is the number of row cells in the unbroken chain.

A same level horizontal score string is a group of one or more same level candidate scores of an unbroken chain of adjacent same row cells, wherein each same level candidate score is calculated by an identical recursive horizontal nonskip calculation. (The identical calculation, is of course, unidirectional.) The length of a same level horizontal score string is the number of scores in the string.

Reference cells of a computational segmenting table. For the fast segmenting algorithm in FSA Teaching Example 1, all of the possible candidate values in the rightmost cell of the second row of the table (corresponding to $F_2(n)$) are calculated and are used to determine (or elect) $F_2(n)$. A selection algorithm (or similar algorithm) is also used to select a subset of the best $\sqrt{n}$ candidate scores in the cell. In like manner, all of the possible candidate values are calculated and the best $\sqrt{n}$ scores selected in some cells of the table as described in 4. of FSA Teaching Example 1. (The calculations in 4. of FSA Teaching Example 1 for a cell is essentially a "recomputation" of all candidate scores.) Each cell for which all of the candidate scores are calculated and a best score subset selected in FSA Teaching Example 1 is a reference cell. (A reference cell may essentially be conceptualized (for versions of FSAs) as a reference-point from which further calculations in neighboring cells begin.)

Similarly, there are zero or more reference cells in a table characterizing versions of FSAs. A reference cell of an FSA is any cell with the following two characteristics. (1) A large number of the possible candidate score values, $C_j(v,m)$, is computed in (or for) the cell. (2) And a proper subset of the best or approximately best scores of the large number computed for the cell is selected. The term large number includes (but is not limited to) (a) all, (b) essentially all, (c) a high percentage, (d) most, (e) a random sample of the set of all candidate scores in the cell or (f) a statistically suitable number of the set of all possible candidate values for a cell. (The term "statistically suitable number" here means a number great enough that there is a reasonable or high probability that an $F_j(m)$ value for the cell is determinable using the number. A value of $F_j(m)$ that is determinable is one that is reliably or reasonably described by one or more of the election categories (1)-(5). In some cases, the magnitude of a statistically suitable number depends on the data point values $y_1, y_2, \ldots, y_n.)^{XVI}$

[XVI] Some FSAs have no reference cells. In some of these FSAs, two or more pseudoreference cells substitute for each of one or more reference cells. Two or more pseudoreference cells serve a similar purpose as a single reference cell. The number of candidate scores in a pseudoreference cell does not qualify as "large number of scores" as defined for a reference cell. However, the total number of candidate scores computed for two or more pseudoreference cells is effectively "a large number". For example, if a large number is $c^A$, but $c^A/2$ is not a large number, $c^A/2$ scores are computed in each of two adjacent (or nearby) same row cells. (The computed scores in each cell are at different levels.) A best score subset of the $c^A/2$ scores in each cell is computed and used as a horizontal start subset for each cell. Horizontal calculations in both leftward and rightward directions imitate the effect of a single reference cell wherein $c^A$ scores were calculated. The two reference cells have imitated a single reference cell in effect.

Selecting a best score subset or an approximate best score subset for a reference cell. As described in the FSA Teaching Example 1, a best score subset is chosen from the set of all possible candidate scores for each reference cell, using a selection algorithm or an equivalent thereof. (The size of each best score subset in FSA Teaching Example 1 is $\sqrt{n}$). Similarly, versions of FSAs select a best score subset or an approximate best score subset for each reference cell in a table that characterizes the operation of these versions of FSAs. The size of a best (or approximate best) score subset is the number of scores in the subset.

Using a best score subset or an approximate best score subset of a reference cell to calculate candidate scores for nearby cells using one or more horizontal calculations. Each of one or more versions of FSAs selects a best or an approximate best score subset in each reference cell of a table that characterizes each of the one or more versions of FSAs. And each of the one or more versions of FSAs uses one or more of the scores in the selected subset to form a horizontal start subset. Each score in the start subset is then used (by these FSAs) to calculate one or more candidate scores in nearby cells of the same row with one or more horizontal calculations.

Such a version of an FSA is described in each of FSA Teaching Examples 1 and 2. In these examples, the set of all possible candidate scores is calculated for each reference cell. A best score subset of size c is selected for each reference cell. And these c scores are used to in one or more recursive (leftward) horizontal calculations to calculate c of the candidate scores in each of one or more same row cells of a table (similar to Table 1). (So that each horizontal start subset has c scores as members of each start subset.) The length of each of these recursive horizontal nonskip calculations is essentially c cells. The number c is $\sqrt{n}$ and log n respectively for Examples 1 and 2.

The size of a horizontal start subset is the number of scores in the subset. In FSA Teaching Examples 1 and 2, the size of each horizontal start subset is equal to c, the size of the best score subset selected for each reference cell.

Candidate score values that originated with a (score of) horizontal start subset (of a reference cell). Versions of FSAs use one or more recursive horizontal (skip or nonskip, or skip and nonskip) calculations to calculate one or more candidate scores in one or more same row cells of a table. Each such calculation starts with a score of a horizontal start subset. A candidate score that is calculated using a horizontal calculation that started with, or crossed, a score of a horizontal start subset is a score that a horizontal start subset. Alternatively such a candidate score originated with a score of a horizontal start subset.

Size limited cells. As seen from examining Table 1, the size of the set of all possible candidate scores in a cell decreases the further the cell is to the left of the table. For example, the cell corresponding to $F_2(3)$ has only two candidate scores. For a cell corresponding to $F_j(m)$ the number of candidate scores in Table 1 is m−j+1. Similarly, the maximum number of possible candidate scores for any cell of any computational segmenting table is m−j+1. Defining the size of a cell of a table as the total number of candidate scores computed in (or for) the cell, it is clear that each cell has a maximal possible size. That maximal possible size is m−j+1. So each cell of a computational segmenting table is limited to each cell's maximal possible size, m−j+1.

FSA Teaching Examples 1 and 2 each describe preferred versions of FSAs. In each of these FSA versions, a subset of c best candidate scores is selected in each reference cell. And c scores are calculated in each of one or more same row cells using one or more recursive horizontal nonskip calculations.

However, it is impossible for each of one or more (size limited) cells to have c candidate scores calculated for each of the one or more cells. This is because, m−j+1<c for those cells.

Completeness of a Computational Segmenting Table. It is not necessary that a computational segmenting table be complete in order to characterize the operation of a segmenting algorithm. For example, for some versions of an FSA, all of the candidate values for $F_k(n)$ are calculated using a vertical calculation. For some such-versions of an FSA, the cells corresponding to j=k (last row)-and m<n are empty and $F_j(m)$ is undetermined. This is because there is no need to calculate candidate scores (or determine $F_j(m)$) in those cells in order to determine $F_k(n)$.

Void cells. For some versions of FSAs, computational segmenting tables that characterize the operation of the FSAs have an empty cell (or an undetermined value for $F_j(m)$) even when j<k and m≧j. Such a cell is a void cell. For a void cell, $F_j(m)$ is undetermined for a particular value of j and m. This means that whatever the final k-way split of the n data points (done by such an FSA), the final split does not include a j-way split of the m data points $y_1, y_2, \ldots, y_m$ for the particular values of j and m. Similarly when one of more void cells is present in a table, the final k-way split of the n data points (done by an FSA characterized by the table), does not include a j-way split of the m data points $y_1, y_2, \ldots, y_m$ for the particular values of j and m that correspond to the void cells. (When a void cell is present in a table, then $C_j(v,m)$ is not calculated for any value of v for the particular values of j and m corresponding to the void cell.)

Fast cells of a computational segmenting table. A cell of a computational segmenting table wherein a proper subset of all possible candidate scores is computed using one or more horizontal calculations is a fast cell of the table. In addition, the total group of candidate scores computed (by any means) for a fast cell is also a proper subset of the set of all possible candidate scores. So that a cell wherein all possible candidate scores are computed is not a fast cell. An example of a fast cell is the cell corresponding to $F_2(n-1)$ in FSA Teaching Example 1.

For some versions of Fast Segmenting Algorithms, a cell is a fast cell and a reference cell. A fast cell that is also a reference cell is a fast reference cell. A fast cell that is not a reference cell is a simple fast cell. A fast cell wherein one or more of the candidates scores calculated for the cell originated with a score of a horizontal start subset (of a reference cell) is a select fast cell. A select fast cell that is not reference cell is a simple select fast cell, abbreviated ss fast cell.

A string of same origin candidate scores is a sequence of equal level candidate scores in an unbroken chain of adjacent row cells, wherein each candidate score in the sequence originated with the same score of a horizontal start subset. The length of a string of same origin candidate scores is the number of scores in the string. The direction of a string is the direction of the horizontal recursive calculation that generated the string. The first score of a string is the first score in the sequence of candidate scores. The cell that contains the first score in the string is the first cell of the string. And the last score of a string is the last score in the sequence. The cell that contains the last score in the string is the last cell of the string.

A chain of same origin simple select fast cells. An unbroken chain of adjacent same row ss fast cells, wherein each cell has a candidate a score that originated with the same score of a horizontal start subset is a chain of same origin simple select fast cells. A chain of same origin simple select fast cells is abbreviated as-a chain of soss fast cells. (One or more chains of soss fast cells are described in FSA Teaching Example 1.

The length of each of these chains is essentially $\sqrt{n}$ cells.) The length of an soss fast cell chain is the number of cells in the chain. A chain of soss fast cells is essentially an unbroken sequence of adjacent row cells, wherein the sequence of cells contains one or more strings of same origin candidate scores.

The size of a cell. The size of a cell is the total number of candidate score values computed in the cell. The size of a cell is maximal if the set of all possible candidate scores is computed for the cell. The size of a reference cell is the total number of candidate score values computed in the cell. For example, in the FSA described under FSA Teaching Example 1, the sizes of the cells corresponding to $F_2(n)$ and $F_3(n)$, are n−1 and n−2 respectively. For versions of fast segmenting algorithms, each particular reference cell has a particular size. So for versions of FSAs, it is possible for two different reference cells to have two different sizes.

The size of a fast cell is the total number of candidate score values computed in the cell. For some versions of fast segmenting algorithms, each particular fast cell has a particular size. So for some versions of FSAs it is possible for two different fast cells to have two different sizes. For example, in the FSA described under FSA Teaching Example 1, essentially all of the fast cells have the same size, that size is $\sqrt{n}$.

The horizontal size and vertical size of a cell. Each cell has a size. The size of each such cell is further divided into a horizontal size and a vertical size. The horizontal size of a cell is the total number of candidate score values computed in the cell using a horizontal calculation. For example, in the FSA described under FSA Teaching Example 1, essentially all of the fast cells have the same horizontal size, that horizontal size is $\sqrt{n}$. (The vertical size of each of the fast cells is zero, because all of the candidate scores of each fast cell is computed using a horizontal calculation.)

The vertical size of a cell is the total number of candidate score values computed in the cell using a vertical calculation. For example, in the FSA described under FSA Teaching Example 1, the vertical size of the cell corresponding to $F_2(n)$ is n−1. (The horizontal size of the cell corresponding to $F_2(n)$ is zero, because all of the candidate scores in the cell are computed using a vertical calculation.)

A directional rectangle of same origin candidate scores is a group of one or more strings of same origin candidate scores of equal length, wherein each string in the group has the same first cell and each string in the group has the same last cell. A candidate score in a string of the group, is a score in, within or contained in the rectangle. The length of the rectangle is the number of scores in each score string (in the rectangle). And the width of the rectangle is the number of strings in the group. The first cell and last cell of the rectangle is respectively the first cell and last cell of each string in the group. A first or last cell of the rectangle is an end cell of the rectangle. If each score in each string of the group originated with a score of a horizontal start subset of one (same) reference cell, then the rectangle arises from the reference cell. If the last cell of the rectangle is adjacent to a reference cell, then the rectangle terminates on the reference cell. If the rectangle arises from a first reference cell and terminates on a second reference cell, then the rectangle is compatible with the pair of reference cells (wherein the pair consists of the first and second reference cells). The direction of the rectangle (leftward or rightward) is the direction of each string in the rectangle. (As is seen from FSA Teaching Examples 1 and 2, a rectangle of same origin candidate scores that is compatible with a pair of reference cells is a preferred rectangle.)

A cell block that fits a rectangle of same origin candidate scores is an unbroken chain of adjacent same row cells wherein each score in the rectangle is a score within a cell of the chain. And each cell of the chain contains one or more candidate scores in the rectangle. An end cell of the block is a first cell or last cell of the rectangle. (It is possible for a cell block to fit two or more rectangles, wherein one or more of the rectangles have a different direction.)

A pair of nearest same row reference cells is a pair of reference cells (in the same row of a table) that has no reference cell (in the same row of the table) between the pair.

An soss fast cell block is a chain of soss fast cells that fits one or more rectangles of same origin candidate scores. If one or more the rectangles is compatible with a pair of (nearest same row) reference cells, then the soss fast cell block is congruent with the reference cell pair. The length of the fast cell block is the length of the soss fast cell chain. In FSA Teaching Example 1, essentially each soss fast cell block is congruent with a (nearest same row) reference cell pair. (In contrast to a pure block, below, it is possible for a cell of an soss fast cell block to contain one or more scores that are not in one rectangle. It is possible for the vertical size of one or more of the soss fast cells in the chain to be greater than zero. It is possible for two different fast cells in the chain to have different horizontal sizes.)

A pure soss fast cell block is a chain of soss fast cells, wherein each cell of the chain contains only one or more candidate scores in a largest rectangle of one or more rectangles (of same origin candidate scores, of the same direction and length). And each candidate score in the largest rectangle is contained in a cell of the chain of soss fast cells. A candidate score that is not contained in the largest rectangle is not a cell of the block. If the largest rectangle is compatible with a (nearest same row) reference cell pair, then the pure soss fast cell block is congruent with the reference cell pair. Expressed another way, a pure soss fast cell block is essentially an soss fast cell chain that contains only one or more strings of same origin candidate scores, and each of the strings has the same direction and length. Each cell of the soss fast cell chain has the same horizontal size. And the vertical size of each cell of the chain is zero. And each pair of same level candidate scores (of two cells in the soss fast cell chain) are part of the identical horizontal score string. The length of the fast cell block is the length of the soss fast cell chain. The width of the block is the horizontal size of each cell of the soss fast cell chain. The last and first cells of the block are the last and first cells respectively of a rectangle, wherein the block fits the rectangle. (In FSA Teaching Examples 1 and 2, the length and width of each pure soss fast cell block are essentially equal (and equal the number c). In these Examples, essentially each pure soss fast cell block is congruent with a (nearest same row) reference cell pair.)

The interval length between a pair of nearest same row reference cells is the number of cells in the same row that are between the two reference cells of the pair. For example, in the fast segmenting algorithm described under FSA Teaching Example 1, the interval length between a pair of nearest same row reference cells is essentially $\sqrt{n}$. In fact, in FSA Teaching Example 1, the interval length between essentially all pairs of nearest same row reference cells is $\sqrt{n}$. So that for this example of versions of fast segmenting algorithms, the reference cells occur periodically (or essentially periodically), with a period of essentially $\sqrt{n}$ (cells).

More on the election (or determination) of an $F_j(m)$ value. Each elected value $F_j(m)$ is determined using one or more candidate score values. And each of one or more FSAs calculate each candidate value using a horizontal or a vertical calculation. It follows that each of one or more FSAs determine each of one or more $F_j(m)$ values using a combination of one or more vertical calculations combined with one or more horizontal calculations.

Determination (or election) of $F_k(n)$. $F_k(n)$ is an overall score function value for a k-way split of n sequential data points $(y_1, y_2, \ldots, y_n)$. $F_k(n)$ is a score that is (1) a (definite) optimal score value, (2) an approximate (definite) optimal score value, (3) a probable optimal score value, (4) an approximate probable optimal score value, or (5) a statistically meaningful value (a value that corresponds to a statistically meaningful split). If $F_k(n)$ is not reliably or reasonably described by one (or more) of the categories (1) through (5), then $F_k(n)$ does not correspond to a split and $F_k(n)$ is assigned the value (6) "undetermined".

A computational segmenting table that characterizes some versions of segmenting algorithms that determine $F_k(n)$ has essentially only j−1 complete rows. In some such cases, for example, $F_k(n)$ is elected from candidate values that have been calculated using a vertical calculation with one or more $F_{k-1}(m)$ values previously generated.

A computational segmenting table that characterizes some versions of segmenting algorithms that determine $F_k(n)$ has essentially j complete rows. In some such cases, for example, $F_k(n)$ is elected from candidate values that have been calculated using one or more horizontal calculations with one or more $F_k(m)$ values previously generated, wherein $m \leq n-1$.

In addition, for some other versions of segmenting algorithms, $F_k(n)$ is determined using a combination of vertical and horizontal calculations.

Storing or recording information on the candidate score value in a cell that is determined to be $F_j(m)$. A candidate score value $C_j(v^\Delta, m)$ for a particular value of v, $v^\Delta$, is determined by a segmenting algorithm to be $F_j(m)$. In such a case, $C_j(v^\Delta, m) = F_j(m) = F_{j-1}(v^\Delta) + r(v^\Delta+1, m)$. By recording (or storing) the value $v^\Delta$, or $v^\Delta+1$, or an equivalent value, a traceback procedure is used determine one or more endpoints of the segment(s) of the split associated with $F_k(n)$. Inherent in any computational segmenting table is the storage or recording of values of $v^\Delta$ for cells of the table. (It is possible to conceptualize the storage of values of $v^\Delta$ (or an equivalent) in cells of a computational segmenting table or in a corresponding table.)

Utility of Versions of FSAs wherein a Table that Characterizes each of the FSAs Includes One or More Void Cells or One or More Horizontal Skip Calculations.

Figure 5:
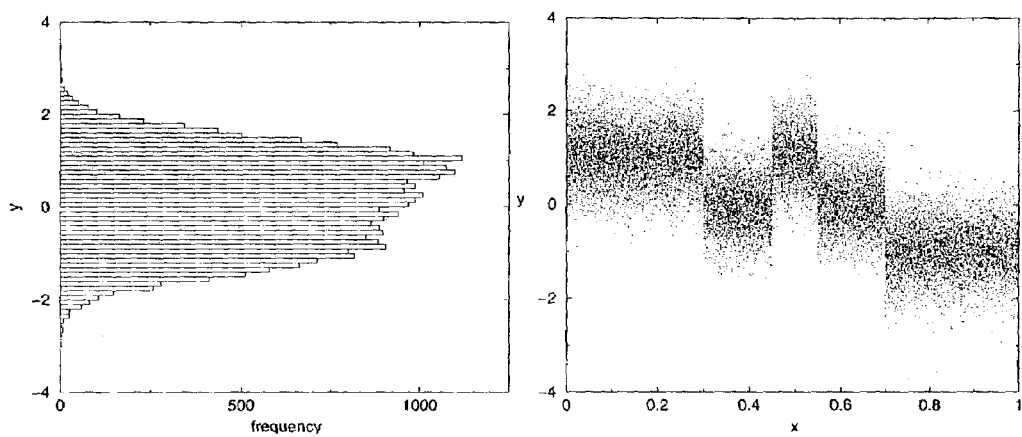
FIG. 5 Data Segmentation Example The histogram of y is depicted at left. It is unobvious without plotting y versus x that there is any pattern to the data. We see at right, that the mean of y is constant within certain ranges of x. The optimal segmentation of this data would be to divide x with cutpoints at 0.3, 0.45, 0.55, and 0.7.

Some versions of FSAs essentially use one or more void cells or one or more horizontal skip calculations in segmenting. When a void cell is present in a table, then $C_j(v,m)$ is not calculated for any value of v for the particular values of j and m corresponding to the void cell. Given a level of a cell of a table that corresponds to particular values of v, j and m, when a horizontal skip calculation skips the level (of the cell), then no candidate score $C_j(v,m)$ is calculated for the particular values of v, j and m. When an FSA essentially uses one or more void cells or one or more horizontal skip calculations in segmenting, then particular component splits are eliminated from being part of the final k-way split chosen by the FSA. In some cases (such as for certain types of data points) the elimination of one or more component splits does not cause difficulties. For example, if the number of data points, n, is very large and the number of segments, k, is much smaller than the number of data points (such as in FIG. 5), and the transition between one or more "segments" is not abrupt, then an exact endpoint for each segment is frequently not critical. In some such situations, a k-way split by an FSA that uses one or more void cells or one or more horizontal skip calculations has increased speed without significantly sacrificing meaningfulness of the splits found by the FSA. This is one nonlimiting example.

Utility of Versions of FSAs wherein each FSA Employs a Measure of Segment Homogeneity that uses an Approximate Mean.

As noted by examining equations 3, 4 and 5, some measures of segment data point homogeneity employ deviation from an exact or an approximate mean. A nonlimiting example wherein a measure of segment data point homogeneity that employs deviation from an approximate mean has utility is seen in the following situation. As noted above, versions of FSAs use a horizontal calculation to calculate $C_j(v,m)$ from $C_j(v,m+1)$. This is done using the equations $C_j(v,m)=F_{j-1}(v)+r(v+1, m)$ and $C_j(v,m+1)=F_{j-1}(v)+r(v+1, m+1)$. The two values $C_j(v,m)$ and $C_j(v,m+1)$ differ from each other by only one data point (or observation) in the expression for $r(\ )$. That data point is $y_{m+}$. By removing $y_{m+1}$ from the expression for $r(v+1, m+1)$, $C_j(v,m)$ is calculated. However the expressions $r(v+1, m)$ and $r(v+1, m+1)$ use different means. By using the mean of the data points $y_{v+1}, Y_{v+2}, \ldots, Y_{m+1}$ (the mean used in the expression for $r(v+1, m+1)$) as an approximate mean for the data points $y_{v+1}, Y_{v+2}, \ldots, y_m$ in the expression for $r(v+1, m)$ is obtained. This approximate value is likely to be meaningful if the number of data points, n and m-v, is very large and the number of segments, k, is much smaller than the number of data points (such as in FIG. 5). Moreover, the use of the approximate mean in the expression for $r(v+1, m)$ saves a calculation and increases speed.

Description of Versions of FSAs

The operation of each Fast Segmenting Algorithm is characterized by a computational segmenting table. Each table characterizing an FSA has one or more fast cells in the table. (In contrast, a table characterizing a Hawkins DP algorithm has no fast cells in the table.) Some versions of FSAs have one or more reference cells in a table characterizing each of these versions of FSAs. Some versions of FSAs have one or more candidate scores in one or more fast cells (of a table characterizing each of these versions of FSAs), wherein each of the one or more candidate scores originated with a score of a horizontal start subset.

A General Description of Versions of Fast Segmenting Algorithms

A general description of versions of FSAs is given below. (This general description is not necessarily limiting. There are other general descriptions of versions of FSAs that are supported by the subject matter contained herein.) This general description uses a computational segmenting table that characterizes the operation of the generally described versions of FSAs, wherein the table has one or more fast cells.

1) A computer-based segmenting algorithm (or method) for finding one or more k-way splits of n data points (in sequential order), comprising:

calculating a subset of the candidate score values for each of one or more cells of a computational segmenting table, wherein the operation of the algorithm is characterized by the table, wherein one or more cells of the table is a fast cell (, wherein only a proper subset of the set of all candidate scores is calculated in each fast cell, and each of one or more of the candidate scores calculated in each fast cell is calculated using a horizontal calculation);

electing a score value $F_j(m)$ for each cell in the table using zero or more candidate score values in each cell, so that the score value $F_j(m)$ for each cell of the table is reliably or reasonably described by one or more election categories;

determining $F_k(n)$ using one or more values of $F_j(m)$ from the table, so that $F_k(n)$ is reliably or reasonably described by one or more election categories; and determining a k-way split of the n data points using $F_k(n)$, the table and a traceback procedure to find one or more endpoints of the split.

Some specific versions of Fast Segmenting Algorithms are also described in terms of attributes of a computational segmenting table that characterizes the operation of an FSA. A computational segmenting table that characterizes the operation of a segmenting algorithm is a table that includes details of the operation of the algorithm to obtain each piece of information used to find the endpoints (or changepoints, or cutpoints) of each segment of the k-way split made by the algorithm. Such details include FSA attributes. When a table that characterizes an FSA has one or more attributes, the FSA is said to have the attributes. These FSA attributes include (but are not necessarily limited to) the following attributes:

(1) the measure of segment homogeneity, $r(\ )$ in the table
(2) the measure of overall homogeneity, $F(\ )$ for each cell of the table
(3) the manner in which each candidate score value $C_j(v,m)$ (used to determine each value of $F_j(m)$ was calculated), the calculation route that led to each such candidate score value, the type of calculation that led to each such candidate score value
(4) the election category for each $F_j(m)$ value of each cell of the table
(5) the location of each reference cell of the table (and the total number of reference cells in the table)
   i) whether a best or approximate best score subset is selected for each reference cell; the size of each horizontal start subset
   ii) the size of each best or approximate best score subset selected
   iii) the size of each horizontal start subset
   iv) the interval length between each pair of nearest same row reference cells
(6) the location of each fast cell of the table (and the total number of fast cells in the table)
   i) the horizontal size of each fast cell
   ii) the location of each simple fast cell, and the number of simple fast cells
   iii) the location of each simple select fast cell and the number of simple select fast cells
(7) the number and distribution of void cells in the table
(8) the size of each cell of the table
   i) the vertical size of each cell of the table
   ii) the horizontal size of each cell of the table
(9) the length, direction, starting cell and level of each horizontal recursive calculation
(10) the length, direction, starting cell, level and skip number of each horizontal skip calculation
(11) the number and length of each soss fast cell chain
(12) the number of soss fast cell blocks, the number of pure soss fast cell blocks
(13) the length and width of each block; the first and last cells of each block
(14) the number of directional rectangles of same origin candidate scores, the length, width, and first and last cells of each rectangle.
(15) the number and location of pseudoreference cells Possible FSAs. The following are descriptions of some possible versions of FSAs. An FSA need only have one fast cell. It is possible for an FSA to have any combination of attributes or characteristics described herein, as long as the FSA has one fast cell. It is possible for an FSA to have no reference cells or pseudoreference cells. It is possible for the spacing between pairs of nearest same row reference cells of an FSA to be different. It is possible for the sizes of best or approximately best score subsets of reference cells of an FSA to be different. The spacing of the reference cells of an FSA need not be periodic or essentially periodic. For some FSAs the spacing of one or more pairs of nearest same row reference cells is other than the size of respective horizontal start subsets or best score subsets of one or both of the cells of the pair. Candidate scores in one or more of the same cells of some FSAs are calculated using both right and left horizontal calculations. An FSA need not contain a fast cell block. An FSA with fast cell blocks need not contain a pure fast cell block. It is possible for the length and width of each pure fast cell block of an FSA to be substantially different. There are numerous other possible combinations that characterize other FSAs.

Some preferred versions of fast segmenting algorithms. Versions of FSAs as described in FSA Teaching Examples 1, 2 and 3 are preferred versions of FSAs. Versions of FSAs that are similar to the versions described in FSA Teaching Examples 1, 2, or 3 are preferred versions of FSAs. Generally, the closer (or more similar) a version of an FSA is to one or more of the versions of FSAs described in FSA Teaching Examples 1, 2, and 3 the more preferred the version of FSA. In addition, preferred versions of FSAs have one or more of the following preferred FSA attributes. Generally, the more of the preferred attributes an FSA has, the more preferred the FSA.

Preferred FSA Attributes:

(1) preferred measures of segment homogeneity, r( ), are described above.

(2) preferred measures of overall homogeneity, F( ), are described above.

(3) one or more preferred manners in which each candidate score value $C_j(v,m)$ is calculated are as follows. In preferred versions of FSAs, each candidate score in a reference cell is calculated using a horizontal or a vertical calculation. In preferred versions of FSAs, each candidate score in a fast cell is calculated using a horizontal calculation.

(4) preferred election categories for each $F_j(m)$ value of each cell of a table characterizing a preferred FSA are as follows. The most preferred election category is (1) a (definite) optimal score value, and the least preferred category is (6) "undetermined". The lower the number of the election category, the more preferred the category. The more cells in a table for which $F_j(m)$ is reliably or reasonably described by a more preferred category, the more preferred the FSA (or versions of FSAs) characterized by the table.

(5) preferred locations and numbers of reference cells of preferred versions of FSAs. A preferred location for reference cells is a table is each cell of the rightmost column in a table characterizing an FSA. More on preferred locations and numbers of reference cells is given below.

i) a best score subset is more preferable than an approximate best score subset ii) for some preferred FSAs, the size of each selected best or approximate best score subset is the same or about the same size, c, for each preferred FSA (or table).

Preferred values for c are closest integer values of $\sqrt{n}$ and log n. It is possible for c to be any integer wherein $c \leq n$. Other values of c are closest integer values given by the following equations: $c = n^{1/q}$ or $c = \log_q n$, wherein $q \geq 1$.

ii)

iii) a preferred interval length between each pair of nearest same row reference cells is about the size (in terms of cells) of one or both of the reference cells of each pair. When all of the reference cells of a table characterizing an FSA are of equal or about equal size c, then a preferred interval length is c or about c. A preferred spacing of reference cells is essentially periodically in each table row. A preferred period is c or about c cells.

(6) one or more preferred locations of one or more simple fast cells of a table characterizing one or more preferred FSAs is wherein each simple fast cell is one of an unbroken chain of same row simple fast cells that occur between nearest same row reference cells.

i) A preferred horizontal size for a simple fast cell is the same or about the same size as a selected best or approximate best score subset of one or both reference cells of a pair of nearest same row reference cells, wherein the simple fast cell is between the pair of reference cells. A preferred horizontal size for a simple fast cell is the same or about the same size as a selected best or approximate best score subset of a nearest same row reference cell. A preferred horizontal size for each of one or more simple fast cells of a table that characterizes a preferred FSA is the size c (or about c), wherein c is the size of a selected best or approximate best score subset of each reference cell of the table. Preferred values for c are $\sqrt{n}$ and log n.

(7) Generally a preferred value for the number of void cells in a table that characterizes an FSA is a small percentage of the total number of cells in the table. Generally a more preferred value for the number of void cells in a table that characterizes an FSA is less than about 10% of the total number of cells in the table. Generally a most preferred value for the number of void cells in a table that characterizes an FSA is less than about 1 %. And generally an optimal number of void cells is zero or about zero. A preferred distribution of void cells is essentially periodic in terms of position in a row of a table.

(8) Some possible sizes for a reference cell are (a)all, (b)essentially all, (c)a high percentage, (d)most, or (e)a statistically suitable number of the set of all possible candidate values for a cell. A most preferred size for one or more reference cells of a table that characterizes one or more preferred FSAs is (a) all, a least preferred size is (e). Generally, the closer the size is to (a), the more preferred the size for one or more reference cells.

i) a preferred vertical size of each of one or more simple fast cells of a table that characterizes one or more preferred FSAs is zero or about zero ii) information on preferred horizontal sizes for one or more simple fast cells is given above (9) a preferred starting point for each of one or more horizontal recursive calculations is essentially a reference cell, a preferred length for each of one or more horizontal recursive calculations is essentially the number of same row cells between two nearest same row reference cells. Other starting points and lengths are possible.

(10) a preferred starting point for each of one or more horizontal skip calculations is essentially a reference cell; generally smaller skip numbers are preferred a preferred skip number is less than 10% of n, a more preferred skip number is less than 1%, a most preferred skip number is zero. Skip numbers greater than 10% are possible.

(11) One or more soss fast cell chains are more preferred than one or more isolated simple select fast cells.
(12) Soss fast cell blocks are preferred. Pure soss fast cell blocks are more preferred than soss fast cell blocks. One or more pure soss fast cell blocks of about equal length and width are preferred. One or more pure blocks wherein all of the pure blocks have approximately equal length and width are more preferred. Each pure block contains a largest rectangle. One or more pure blocks, wherein the length and width of the largest rectangle (contained in each block) is about equal to the size of a best or approximate best score subset of a reference cell from which the rectangle arises are preferred. Pure blocks that are congruent with a reference cell pair are preferred.
(13) One or more directional rectangles of same origin candidate scores, wherein each rectangle is compatible with a nearest same row pair of reference cells are preferred. One or more rectangles of approximately equal length and width are more preferred. One or more rectangles wherein all of the rectangles have approximately equal length and width are more preferred. One or more rectangles wherein the length and width of each rectangle is equal or approximately equal to the size of a best or approximate best score subset of a reference cell from which each rectangle arises are preferred.
(14) Reference cells are preferred over pseudoreference cells. Although numerous preferred attributes have been listed, less preferred versions of FSAs have advantages in some situations. These situations are often dependent on the types of data points being segmented.

The present patent application claims priority from U.S. provisional patent application 60/225,113 filed 14 Aug. 2000 and all of the contents U.S. provisional application 60/225,113 are incorporated herein by reference and to the fullest extent of the law. The present application is a CIP of PCT/US01/25519 (having the same title) filed 14 Aug. 2001 and PCT/US01/25519 is incorporated herein by reference in its entirety and to the fullest extent of the law. The present application claims priority from U.S. provisional patent application 60/358,631 filed 20 Feb. 2002 and all of the contents 60/358,631 are incorporated herein by reference and to the fullest extent of the law.

I TYPE FSA APPENDIX

Discrete Data Points (or Values) in a Sequential Order.

Let $y_1, y_2, y_3 \ldots, y_{n-2}, y_{n-1}, y_n$ be a group of n discrete data values or data points. (It is also possible to speak of these n discrete data values (or points) as a vector of data, wherein the vector has length n. And it is also possible to speak of these n discrete data values as vector y.)

"Segmenting" Such a Group of Points into Nonoverlapping "Segments".

As taught in PCT/US01/25519 (i.e. pp. 35 and 36) and elsewhere, it is possible to subgroup these n data points into k segments ($k \leq n$), so that each of the n data points belongs to one and only one segment. As taught in PCT/US01/25519 (referred to herein as 25519) and elsewhere it is possible to perform such as segmentation of data points using measures of inter-segment data value inhomogeneity (see for example p. 9, line 8 of 25519). There are many different kinds of inhomogeneity measures taught in the art.

Segmenting in Such a Way that the Data Points within Each Segment are Homogeneous or Alternatively so that there is Inter-Segment Data Point Inhomogeneity.

It is possible to segment a group of seguential data points into k segments many ways. However, it is a coal of a segmenting algorithm (or segmentation process) that the points within each segment be essentially similar in value or homogeneous. Or alternatively it is a goal of a segmenting algorithm that there be inter-segment data value inhomogeneity. Thus a segmenting algorithm essentially chooses (or prefers) only coverings for which the data points within each segment are essentially homogeneous (in value). Or alternatively a segmenting algorithm essentially chooses (or prefers) only coverings for which there is inter-segment data value inhomogeneity.

An Example of a Measure of Inter-Segment Data Value Inhomogeneity.

Let consecutive data points $y_b, y_{b+1}, y_{b+2}, y_{b+3}, \ldots y_c, y_{c+1}, \ldots y_{e-2}, y_{e-1}, y_e$ be a subset of the group of n discrete consecutive data points $y_1, y_2, y_3, \ldots, y_{n-2}, y_{n-1}, y_n$. The data points from $y_b$ to $y_c$ and the data points from $y_{c+1}$ to $y_e$ are two subsets of points belonging to adjacent segments. Define the following intra-segment point means (or approximate means):

$$\overline{y}_{b,c} \cong \frac{\sum_{m=b}^{c} y_m}{c-b+1} \qquad \text{Equation Inhom 1}$$

$$\overline{y}_{c+1,e} \cong \frac{\sum_{m=c+1}^{e} y_m}{e-c} \qquad \text{Equation Inhom 2}$$

In equations Inhom 1 and 2, the mean is an exact or approximate mean. (The exact mean is a preferred value.)

Define a measure of inter-segment data value inhomogenity for these two segments as:

$$d(b:c,c+1:e) \cong |\overline{y}_{b,c} - \overline{y}_{c+1,e}| \qquad \text{Equation Inhom 3}$$

In Equation Inhom 3 the Measure is an Exact or Approximate Value. (the Exact Value is a Preferred value.)

The measure d(b:c, c+1:e) is a hiqh value if there is inter-segment inhomogeneity (i.e. if the data point values $y_b, y_{b+1}, \ldots, y_c$, and $y_{c+1}, y_{c+2}, \ldots, y_e$ are inhomogeneous with respect to each other). The measure d(b:c, c+1:e) is an inter-segment inhomogeneity score function for two adjacent segments. Summinq all of the d(b:c, c+1:e) for a covering gives a measure of overall homogeneity for the covering.

By adding all the d(b:c, c+1:e) values for a covering, a measure of the overall inter-segment inhomogeneity of the covering is obtained. Denoting the data points within the k segments of a covering as the values from 1 to $n_1$, $n_1+1$ to $n_2, \ldots, n_{k-1}$ to n; an overall measure Wd, of the inter-segment inhomogeneity of the segments (of the covering) is given by Wd=d(1:$n_1$, $n_1+1$: $n_2$)+d($n_2+1$:$n_3$, $n_3+1$: $n_4$)+ . . . +d($n_{k-2}+1$: $n_{k-1}$, $n_{k-1}+1$: n). High values of Wd then correspond to higher degrees of inter-segment inhomogeneity of a covering. With such a strategy, an appropriate choice of segments (for a covering) is to choose values of $n_1, n_2, \ldots, n_{k-1}$ for which Wd is maximized. The overall measure Wd is an inter-segment inhomogeneity score function for a split or covering. In 25519 Hawkins work is cited. This work shows how to find such an optimal set of k segments by using a dynamic programming computer algorithm.[16] This algorithm can be easily adapted to using measures of inter-segment inhomogeneity. This is because a principle (cited just below) applies to both overall measures of intra-segment data value homogeneity and inter-segment data value inhomogeneity.

Hawkins's Dynamic Programming (DP) Algorithm for Finding an Optimal Covering of n Data Points Using K Segments.

Hawkins's algorithm is based on the following principle. Given n data points, and an optimal covering using k segments (or a best k-way split), the last endpoint (or cutpoint) of the covering is $n_{k-1}+1$. Since this k-segment covering is an optimal covering for the data points from 1 to n, it follows that this covering is composed of an optimal k−1 segment covering for the data points from 1 to $n_{k-1}$ plus the last segment covering points $n_{k-1}+1$ t n.[17] Thus if the optimal k−1 segment coverings for data points 1 to m, for each point m, $1 \leq m \leq n$ is known, then it is easy to find the optimal k segment coverings for the data points from 1 to n. This is done using a simple search. This simple search essentially calculates "forward" by starting 1-way splits, then deduces optimal 2-way splits from the 1-way spits, and this process is repeated recursively to deduce optimal q-way splits from the optimal (q−1)-way splits. This process is repeated until the optimal k-way split of n data points is found. The boundaries of the optimal segments are deduced from a "traceback" procedure.

Adapting the Hawkins DP Algorithm for Use with a Measure of Inter-Segment Inhomogeneity The adapted algorithm is as follows. This adapted algorithm uses the principles cited above that are utilized by the Hawkins DP algorithm. Adapted Algorithm: Let $F_j(m)$ be the measure Wd for an optimal j-way split for the data points 1 to m; and define $F_1(m)=0$ for all m. (Wd is a measure of overall inter-segment data value inhomogeneity as defined above, wherein Wd is the sum of d( ) values; and each d( ) value is an absolute difference of the means of data point values of adjacent segments. Therefore defining $F_1(m)=0$ is appropriate, as well as being appropriate when substituted into the relation $F_j(m)=\max \{F_{j-1}(v)+d(x_{j-1,v}:v,v+1:m)\}$ given below.)

Then $F_j(m)=\max \{F_{j-1}(v)+d(x_{j-1,v}:v,v+1:m)\}$, $j-1 \leq v \leq m-1$ for $m=2, \ldots, n$; $j \leq m$, wherein $x_{j-1,v}$ is the first point of the last segment of the optimal j−1 way split of v data points. (It is clear that $F_2(m)=\max \{d(x_{1,v}:v,v+1:m)\}$, $1 \leq v \leq m-1$.) Computational tables of $F_j(m)$ are generated for m=2 to n and j=2, 3, . . . , k. The value of Wd for an optimal k-way split on n data points is $F_k(n)$ and $F_k(n)$ is deduced as described above. The boundaries of the optimal segments are deduced from a "traceback" procedure.

In 25519, Table 1, a computational segmenting table, is used to illustrate the operation of the Hawkins DP algorithm. The following table, Table 2, is similar to Table 1 and illustrates the operation of the adapted algorithm (a segmenting algorithm that finds an optimal split using measures of inter-segment inhomogeneity by calculating a measure for each possible split).

There are some differences between Table 2 below and Table 1 in 25519, however these differences do not affect the speed of the algorithm which is comparable to the Hawkins DP algorithm. One difference is that $F_1(m)=0$ for all m, meaning the top row of Table 2 has zeros for all values of the table.

Another difference is that for each cell of the table (in row j, column m) the calculation of candidate score values to be $F_j(m)$ require a knowledge of $x_{j-1,v}$, for values of v wherein $j-1 \leq v \leq m-1$, $x_{j-1,v}$ being the first point of the last segment of the optimal j−1 way split of v data points. However, this is not really a significant departure from the operation of the Hawkins DP algorithm or similar algorithms. Because the value of $x_{j-1,v}$ is saved and used by the Hawkins DP Algorithm (and similar modified algorithms, such as FSA Teaching Examples 1-3) in order to practice the traceback procedure. Finally, a candidate score value becomes an actual $F_j(m)$ value by being a maximum in the adapted algorithm, rather than a minimum as in the Hawkins DP algorithm.

There are, however, major similarities between Tables 1 and 2. For example, candidate score values in Table 2 that are in adjacent cells of the same row and at the same level differ from each other by only one data point (or observation). Thus this adapted algorithm is modifiable so that one or more modified adapted algorithms have speed that is comparable to the modified algorithms of 25519. (Modified algorithms of 25519 are FSAs including those of FSA Teaching Examples 1-3. FSAs are modifications of the Hawkins DP Algorithm.)

A modified adapted algorithm uses the DP technique of running sums or similar techniques, along with calculating only candidate score values that have a high or reasonable probability of being an optimal score value (as opposed to exhaustively calculating all scores as the unmodified adapted algorithm and the Hawkins DP algorithm calculate all candidate scores.)

In fact by simply changing the wording of 25519 slightly, for example changing maximum to minimum, and using measures of inter-segment inhomogeneity, a description of modified adapted algorithms, that are fast and use measures of inter-segment inhomogeneity, as opposed to measures of intrasegment homogeneity, is obtained. We will refer to these algorithms as I Type FSAs (Inhomogeneity Type Fast Segmenting Algorithms). This is done below, after Table 2.

TABLE 2

|  | F(2) | F(3) | F(4) | F(5) | ... F(n) |
|---|---|---|---|---|---|
| $F_1$ | $F_1(2) = 0$ | $F_1(3) = 0$ | $F_1(4) = 0$ | $F_1(5) = 0$ | ... $F_1(n) = 0$ |
| $F_2$ | $F_2(2) =$ d(1:1, 2:2) | $F_2(3) = \max \{$ d(1:1, 2:3), d(1:2, 3:3)$\}$ | $F_2(4) = \max \{$ d(1:1, 2:4), d(1:2, 3:4), d(1:3, 4:4)$\}$ | $F_2(5) = \max \{$ d(1:1, 2:5), d(1:2, 3:5), d(1:3, 4:5), d(1:4, 5:5)$\}$ | $F_2(n) = \max \{$ d(1:1, 2:n), d(1:2, 3:n), d(1:3, 4:n) . . . d(1:n − 1, n:n)$\}$ |
| $F_3$ | 0 | $F_3(3) = \max \{$ $F_2(2) + d(2:2, 3:3)\}$ | $F_3(4) = \max \{$ $F_2(2) + d(2:2, 3:4)$, $F_2(3) + d(x_{2,3}:3, 4:4)\}$ | $F_3(5) = \max \{$ $F_2(2) + d(2:2, 3:5)$, $F_2(3) + d(x_{2,3}:3, 4:5)$, $F_2(4) + d(x_{2,4}:4, 5:5)\}$ | ... $F_3(n) = \max \{$ $F_2(2) + d(2:2, 3:n)$, ... $F_2(3) + d(x_{2,3}:3, 4:n)$, ... $F_2(4) + d(x_{2,4}:4, 5:n)$, ... $F_2(5) + d(x_{2,5}:5, 6:n)$, . . . |

TABLE 2-continued

| | F(2) | F(3) | F(4) | F(5) | ... F(n) |
|---|---|---|---|---|---|
| $F_4$ | 0 | 0 | $F_4(4) = \max \{$ $F_3(3) + d(3:3, 4:4)\}$ | $F_4(5) = \max \{$ $F_3(3) + d(3:3, 4:5),$ $F_3(4) + d(x_{3,4}:4, 5:5)\}$ | $F_2(n-1) +$ $d(x_{2,n-1}:n-1, n-1:n) \}$ ... $F_4(n) = \max \{$ ... $F_3(3) + d(3:3, 3:n),$ ... $F_3(4) + d(x_{3,4}:4, 4:n),$ ... $F_3(5) + d(x_{3,5}:5, 5:n)$ . . . |
| $F_5$ | 0 | 0 | 0 | $F_5(5) = \max \{$ $F_4(4) + d(4:4, 5:5)\}$ | $F_3(n-1) +$ $d(x_{3,n-1}:n-1, n-1:n)\}$ ... $F_5(n) = \max \{$ ... $F_4(4) + d(4:4, 5:n),$ ... $F_4(5) + d(x_{4,5}:5, 6:n),$ $F_4(6) + d(x_{4,6}:6, 7:n)$ . . . $F_4(n-1) +$ $d(x_{4,n-1}:n-1, n:n)\}$ |

The zeros in the table of rows lower than the first row are where it is impossible to have a k-way split when there are only k-1 or less data points. The score for the optimal 5-way split is given by $F_5(n)$, which is the bottom rightmost entry in the table. The actual positions where the splits occur can be The zeros in the table of rows lower than the first row are where it is impossible to have a k-way split when there are only k-1 or less data points. The score for the optimal 5-way split is given by $F_5(n)$, which is the bottom rightmost entry in the table. The actual positions where the splits occur can be traced if you keep an additional table of the position where the maximum value occurred for each cell in the table. The algorithm is about $O(kn^2)$. For a given row past the first row, the rightmost column takes the minimum of n−1 items, the next to the left takes n−2, so on down to zero. The running time for a given row is thus given by about $O(n^2)$. Because there are k rows for a k-way split, and it costs about $O(n^2)$ to compute the entries for a row, the total running time is thus about $O(kn^2)$.

Description of I Type FSAs

By drawing the computations for the unmodified adapted algorithm (that is similar to Hawkins DP Algorithm that is $O(n^2)$), in a tabular form in Table 2, it is possible to make some novel observations about the computation, and derive new I Type FSAs. Consider the cells that compute the values for $F_3(4)$ and $F_3(5)$. The first element (or candidate score) of the minimum for these two rows is given by $F_2(2)+d(2:2,3:4)$ and $F_2(2)+d(2:2,3:5)$ respectively. Suppose that $F_2(2)+d(2:2,3:5)$ was the lowest score for that cell. It does not follow that $F_2(2)+d(2:2,3:4)$ will be the lowest score for its cell, but because the score computation differs only by a single element (or data point, $y_5$), and the same element (or data point or observation) is removed from the score of each potential minimum in the cell, it is reasonable to expect that it will be among the lowest scores for its cell. This is a key concept. (The values $F_2(2)+d(2:2,3:5)$ and $F_2(2)+d(2:2,3:4)$ are equal level candidate values of adjacent cells of a row in the table. These two values differ only by the data point $y_5$. $F_2(2)+d(2:2,3:5)=C_3(2,5)$ and $F_2(2)+d(2:2,3:4)=C_3(2,4)$, see definitions section for more on candidate values and equal level candidate values.[18]) If we can take the largest d scores for the rightmost cell in a row, if d is sufficiently large, we are guaranteed with high certainty that the maximum score in the next column to the left will be among those d scores, adjusted to remove the observation (or data point) dropped out of the cell to the left. Furthermore, if d is sufficiently large, we are likely to find the best score for subsequent columns among those d scores. However, because we drop an observation (or data point) each time, thus changing the score a bit each time, we will eventually have to recompute a new set of scores from scratch. These ideas lead to the following new algorithms, I Type FSAs.

I Type FSA Teaching Example 1

1. Set $F_1(1) \ldots F_1(n)=0$ for all n, and compute d(1:c, c+1:n) for each value of c=1, 2, 3, ..., n in about O(n) time using a cumulative sum.
2. Compute $F_2(n)$, saving the best (largest) $\sqrt{n}$ scores. Computing the largest $\sqrt{n}$ elements of an n element vector can be done in about O(n) time. This is done with a selection algorithm (or similar algorithm, or one or more algorithms that achieve essentially the same result) in about O(n) time, see chapter ten of reference Cormen (1990).
3. Compute $F_2(n-1)$ by removing the observation from the $\sqrt{n}$ best scores, and computing the maximum of those updated scores. This can be done in about $\sqrt{n}$ time. Repeatedly do this updating procedure to compute $F_2(n-2) \ldots F_2(n-\sqrt{n})$.

What is claimed is:

1. A computer-based Segmentation/Recursive Partitioning process (S/RP process) for clarifying a relationship to a human user, wherein the relationship is between a response and one or more predictors in a real-world data set, comprising:

generating a nodal tree, the response and each predictor having a value for each data object of a group of real-world data objects, the group of data objects is the root node of the tree;

processing the real-world data set, wherein the real-world data is genetics data, chemistry data, clinical trials data, geological data, market research data, data to determine credit scores, demographic data, industrial quality improvement data, pharmacogenomics data, pharmaceutical high-throughput screening data, computational chemistry data or nosocomial infection data;

using one or more FSAs (Fast Segmenting Algorithms), wherein each FSA uses one or more measures of intrasegment homogeneity, wherein each FSA has one or more fast cells, wherein each FSA achieves increased speed by computing an overall measure of segment homogeneity for each of only some of the possible segmentations of the data set, wherein the operation of each FSA is characterized by a computational segmenting table, wherein each FSA is a computer-based segmenting method for finding one or more k-way splits on n data points in sequential order, comprising:

calculating a subset of the candidate score values for each of one or more cells of the computational segmenting table, wherein one or more cells of the table is a fast cell, wherein only a proper subset of the set of all candidate scores is calculated in each fast cell, and each of one or more of the candidate scores calculated in each fast cell is calculated using a horizontal calculation;

electing a score value $F_j(m)$ for each cell in the table using zero or more candidate score values in each cell, so that the score value $F_j(m)$ for each cell of the table is reliably or reasonably described by one or more of five cell score election categories, wherein the five cell score election categories are: (1) a definite optimal score value, (2) an approximate definite optimal score value, (3) a probable optimal score value, (4) an approximate probable optimal score value, or (5) a statistically meaningful score value that corresponds to a statistically meaningful split;

determining an overall score function value for a k-way split of the n sequential data points, wherein the overall score function value is $F_k(n)$, wherein $F_k(n)$ is determined by using one or more values of $F_j(m)$ from the table, so that $F_k(n)$ is reliably or reasonably described by one or more of five overall score election categories, wherein the five overall score election categories are: (1) a definite optimal overall score value, (2) an approximate definite optimal overall score value, (3) a probable optimal overall score value, (4) an approximate probable optimal overall score value, or (5) a statistically meaningful overall score value that corresponds to a statistically meaningful split; and determining a k-way split of the n data points using $F_k(n)$, the table and a traceback procedure to find one or more endpoints of the split;

and displaying the nodal tree on a monitor or equivalent device for use by the human user or storing the nodal tree on a computer readable medium for use by the human user.

2. A process as in claim 1, wherein each FSA has more than one fast cell, wherein the number of data objects in the group of data objects that is the root node is n, wherein n is a positive integer number greater than 100.

3. A process as in claim 2, wherein each FSA has more than one reference cell.

4. A process as in claim 3, wherein all of the possible candidate score values are computed for each reference cell and a best score subset is calculated for each reference cell.

5. A process as in claim 4, wherein the real-world data is pharmacogenomics data or pharmaceutical high-throughput screening data or computational chemistry data.

6. A process as in claim 4, wherein the real-world data is genetics data or chemistry data or clinical trials data.

7. A process as in claim 4, wherein (1) each data object is a molecular data object, whereby each data object represents a molecule and each predictor is a molecular descriptor and the response is a molecular property or wherein (2) each data object represents a human being or tissue from a human being, and each of one or more of the predictors is a combination of one or more alleles or one or more haplotypes at one or more polymorphisms, wherein the response is a phenotypic characteristic.

8. A process as in claim 4, wherein a best score subset and a horizontal start subset is computed for each reference cell, wherein the best score subset and horizontal start subset computed for each reference cell are the same subset, wherein each best score subset and each horizontal start subset have the same size, and the same size is c scores, wherein c is the closest integer number to $\sqrt{n}$ or wherein $c=c_1$, $c_1$ being a positive integer constant less than n, wherein each FSA uses only one measure of intra-segment homogeneity, wherein the one measure of intra-segment homogeneity is r(i,j), wherein the overall measure of segment homogeneity for each of only some of the possible segmentations of the data set is the sum of all the r(i,j) values for each of the possible segmentations.

9. A process as in claim 8, wherein the real-world data is genetics data, pharmacogenomics data, pharmaceutical high-throughput screening data, or computational chemistry data.

10. A process as in claim 8, wherein (1) each data object is a molecular data object, whereby each data object represents a molecule and each predictor is a molecular descriptor and the response is a molecular property or wherein (2) each data object represents a human being or tissue from a human being, and each of one or more of the predictors is a combination of one or more alleles or one or more haplotypes at one or more polymorphisms, wherein the response is a phenotypic characteristic.

11. A process as in claim 8, wherein each FSA uses only one measure of intra-segment homogeneity, wherein the one measure of intra-segment homogeneity is the sum of squared deviations of the data points within a segment about their mean, wherein each fast cell of each FSA has the size of c scores, wherein each fast cell of each FSA also has the horizontal size of c scores, wherein there is a best score for each fast cell, wherein c is sufficiently large that it is likely that the best score for each fast cell is among the c scores computed for each fast cell, wherein c is the closest integer number to $\sqrt{n}$, wherein there are only two cell score election categories: a definite optimal score or a probable optimal score and wherein there is only one overall score election category: a probable overall optimal score value.

12. A process as in claim 11, wherein the real-world data is chemistry data or computational chemistry data.

13. A process as in claim 11, wherein the real-world data is genetics data, pharmacogenomics data, or pharmaceutical high-throughput screening data.

14. A process as in claim 11, wherein each data object is a molecular data object, whereby each data object represents a molecule and each predictor is a molecular descriptor and the response is a molecular property.

15. A process as in claim 11, wherein each data object represents a human being or tissue from a human being, and each of one or more of the predictors is a combination of one or more alleles at one or more polymorphisms, wherein the response is a phenotypic characteristic.

16. A computer readable medium containing a computer software program for controlling a computer-based process, wherein the computer-based process is a Segmentation/Recursive Partitioning process (S/RP process) for clarifying a relationship to a human user, wherein the relationship is between a response and one or more predictors in a real-world data set, comprising:

generating a nodal tree, the response and each predictor having a value for each data object of a group of real-world data objects, the group of data objects is the root node of the tree;

processing the real-world data set, wherein the real-world data is genetics data, chemistry data, clinical trials data, geological data, market research data, data to determine credit scores, demographic data, industrial quality improvement data, pharmacogenomics data, pharmaceutical high-throughput screening data, computational chemistry data or nosocomial infection data;

using one or more FSAs (Fast Segmenting Algorithms), wherein each FSA uses one or more measures of intra-segment homogeneity, wherein each FSA has one or more fast cells, wherein each FSA achieves increased speed by computing an overall measure of segment homogeneity for each of only some of the possible segmentations of the data set, wherein the operation of each FSA is characterized by a computational segmenting table, wherein each FSA is a computer-based segmenting method for finding one or more k-way splits on n data points in sequential order, comprising:

calculating a subset of the candidate score values for each of one or more cells of the computational segmenting table, wherein one or more cells of the table is a fast cell, wherein only a proper subset of the set of all candidate scores is calculated in each fast cell, and each of one or more of the candidate scores calculated in each fast cell is calculated using a horizontal calculation;

electing a score value $F_j(m)$ for each cell in the table using zero or more candidate score values in each cell, so that the score value $F_j(m)$ for each cell of the table is reliably or reasonably described by one or more of five cell score election categories, wherein the five cell score election categories are: (1) a definite optimal score value, (2) an approximate definite optimal score value, (3) a probable optimal score value, (4) an approximate probable optimal score value, or (5) a statistically meaningful score value that corresponds to a statistically meaningful split;

determining an overall score function value for a k-way split of the n sequential data points, wherein the overall score function value is $F_k(n)$, wherein $F_k(n)$ is determined by using one or more values of $F_j(m)$ from the table, so that $F_k(n)$ is reliably or reasonably described by one or more of five overall score election categories, wherein the five overall score election categories are: (1) a definite optimal overall score value, (2) an approximate definite optimal overall score value, (3) a probable optimal overall score value, (4) an approximate probable optimal overall score value, or (5) a statistically meaningful overall score value that corresponds to a statistically meaningful split; and determining a k-way split of the n data points using $F_k(n)$, the table and a traceback procedure to find one or more endpoints of the split;

and displaying the nodal tree on a monitor or equivalent device for use by the human user or storing the nodal tree on a computer readable medium for use by the human user.

17. A computer readable medium containing a computer software program for controlling a computer-based process as in claim 16, wherein each FSA has more than one fast cell.

18. A computer readable medium containing a computer software program for controlling a computer-based process as in claim 16, wherein each FSA has more than one fast cell, wherein the number of data objects in the group of data objects that is the root node is n, wherein n is a positive integer number greater than 100.

19. A computer readable medium containing a computer software program for controlling a computer-based process as in claim 18, wherein each FSA has more than one reference cell.

20. A computer readable medium containing a computer software program for controlling a computer-based process as in claim 19, wherein all of the possible candidate score values are computed for each reference cell and a best score subset is calculated for each reference cell.

21. A computer readable medium containing a computer software program for controlling a computer-based process as in claim 20, wherein the real-world data is genetics data or chemistry data or clinical trials data.

22. A computer readable medium containing a computer software program for controlling a computer-based process as in claim 20, wherein the data set is real-world data and the real-world data is pharmacogenomics data, pharmaceutical high-throughput screening data or computational chemistry data.

23. A computer readable medium containing a computer software program for controlling a computer-based process as in claim 20, wherein each data object is a molecular data object, whereby each data object represents a molecule and each predictor is a molecular descriptor and the response is a molecular property.

24. A computer readable medium containing a computer software program for controlling a computer-based process as in claim 20, wherein each data object represents a human being or tissue from a human being, and each of one or more of the predictors is a combination of one or more alleles or one or more haplotypes at one or more polymorphisms, wherein the response is a phenotypic characteristic.

25. A computer readable medium containing a computer software program for controlling a computer-based process as in claim 20, wherein a best score subset and a horizontal start subset is computed for each reference cell, wherein the best score subset and horizontal start subset computed for each reference cell are the same subset, wherein each best score subset and each horizontal start subset have the same size, and the same size is c scores, wherein c is the closest integer number to $\sqrt{n}$ or wherein $c=C_1$, $C_1$ being a positive integer constant less than n, wherein each FSA uses only one measure of intra-segment homogeneity, wherein the one measure of intra-segment homogeneity is $r(i,j)$, wherein the overall measure of segment homogeneity for each of only some of the possible segmentations of the data set is the sum of all the $r(i,j)$ values for each of the possible segmentations.

26. A computer readable medium containing a computer software program for controlling a computer-based process as in claim 25, wherein the real-world data is genetics data or chemistry data or clinical trials data.

27. A computer readable medium containing a computer software program for controlling a computer-based process as in claim 25, wherein the data set is real-world data and the real-world data is pharmacogenomics data or pharmaceutical high-throughput screening data or computational chemistry data.

28. A computer readable medium containing a computer software program for controlling a computer-based process as in claim 25, wherein each data object is a molecular data object, whereby each data object represents a molecule and each predictor is a molecular descriptor and the response is a molecular property.

29. A computer readable medium containing a computer software program for controlling a computer-based process as in claim 25, wherein each data object represents a human being or tissue from a human being, and each of one or more of the predictors is a combination of one or more alleles, wherein the response is a phenotypic characteristic.

30. A computer readable medium containing a computer software program for controlling a computer-based process as in claim 20, wherein a best score subset and a horizontal start subset is computed for each reference cell, wherein the best score subset and horizontal start subset computed for each reference cell are the same subset, wherein each best score subset and each horizontal start subset have the same size, and the same size is c scores, wherein c is the closest integer number to $\sqrt{n}$ or wherein $c=c_1$, $c_1$ being a positive integer constant less than n, wherein each FSA uses only one measure of intra-segment homogeneity, wherein the one measure of intra-segment homogeneity is the sum of squared deviations of data points within a segment about their mean, wherein each fast cell of each FSA has the size of c scores, wherein each fast cell of each FSA also has the horizontal size of c scores, wherein there is a best score for each fast cell, wherein c is sufficiently large that it is likely that the best score for each fast cell is among the c scores computed for each fast cell, wherein c is the closest integer number to $\sqrt{n}$, wherein there are only two cell score election categories: a definite optimal score or a probable optimal score and wherein there is only one overall score election category: a probable overall optimal score value.

31. A computer readable medium containing a computer software program for controlling a computer-based process as in claim 30, wherein the data set is chemistry data.

32. A computer readable medium containing a computer software program for controlling a computer-based process as in claim 30, wherein the real-world data is genetics data or chemistry data or clinical trials data.

33. A computer readable medium containing a computer software program for controlling a computer-based process as in claim 30, wherein the data set is real-world data and the real-world data is pharmacogenomics data or pharmaceutical high-throughput screening data or genetics data.

34. A computer readable medium containing a computer software program for controlling a computer-based process as in claim 30, wherein each data object is a molecular data object, whereby each data object represents a molecule and each predictor is a molecular descriptor and the response is a molecular property.

35. A computer readable medium containing a computer software program for controlling a computer-based process as in claim 30, wherein each data object represents a human being or tissue from a human being, and each of one or more of the predictors is a combination of one or more alleles, wherein the response is a phenotypic characteristic.

36. A computer readable medium containing a computer software program for controlling a computer-based process as in claim 30, wherein one or more of the predictors is a geometry-based molecular descriptor, wherein the process (1) displays the nodal tree on a monitor or equivalent device for use by the human user by transmitting the nodal tree over the internet or (2) stores the nodal tree on a computer readable medium for use by the human user by transmitting the nodal tree over the internet.

37. A computer readable medium containing a computer software program for controlling a computer-based process as in claim 30, wherein each data object represents an individual creature or tissue from an individual creature and each of one or more of the predictors is a genetic make-up descriptor, wherein the response is a phenotypic characteristic.

38. A computer readable medium containing a computer software program for controlling a computer-based process as in claim 20, wherein the relationship is a complex relationship, wherein the complex relationship is an interaction effect, threshold effect or nonlinearity, wherein the data set is simulated data in the field of pharmacogenomics.

39. An apparatus, wherein the apparatus includes a computer, wherein the computer is programmed to practice a computer-based process, wherein the computer-based process is a Segmentation/Recursive Partitioning process (S/RP process) for clarifying a relationship to a human user, wherein the relationship is between a response and one or more predictors in a real-world data set, comprising:

generating a nodal tree, the response and each predictor having a value for each data object of a group of real-world data objects, the group of data objects is the root node of the tree;

processing the real-world data set, wherein the real-world data is genetics data, chemistry data, clinical trials data, geological data, market research data, data to determine credit scores, demographic data, industrial quality improvement data, pharmacogenomics data, pharmaceutical high-throughput screening data, computational chemistry data or nosocomial infection data;

using one or more FSAs (Fast Segmenting Algorithms), wherein each FSA uses one or more measures of intra-segment homogeneity, wherein each FSA has one or more fast cells, wherein each FSA achieves increased speed by computing an overall measure of segment homogeneity for each of only some of the possible segmentations of the data set, wherein the operation of each FSA is characterized by a computational segmenting table, wherein each FSA is a computer-based segmenting method for finding one or more k-way splits on n data points in sequential order, comprising:

calculating a subset of the candidate score values for each of one or more cells of the computational segmenting table, wherein one or more cells of the table is a fast cell, wherein only a proper subset of the set of all candidate scores is calculated in each fast cell, and each of one or more of the candidate scores calculated in each fast cell is calculated using a horizontal calculation;

electing a score value $F_j(m)$ for each cell in the table using zero or more candidate score values in each cell, so that the score value $F_j(m)$ for each cell of the table is reliably or reasonably described by one or more of five cell score election categories, wherein the five cell score election categories are: (1) a definite optimal score value, (2) an approximate definite optimal score value, (3) a probable optimal score value, (4) an approximate probable optimal score value, or (5) a statistically meaningful value that corresponds to a statistically meaningful split;

determining an overall score function value for a k-way split of the n sequential data points, wherein the overall score function value is $F_k(n)$, wherein $F_k(n)$ is determined by using one or more values of $F_j(m)$ from the table, so that $F_k(n)$ is reliably or reasonably described by one or more of five overall score election categories, wherein the five overall score election categories are: (1) a definite optimal overall score value, (2) an approximate definite optimal overall score value, (3) a probable optimal overall score value, (4) an approximate probable optimal overall score value, or (5) a statistically meaningful overall value that corresponds to a statistically meaningful split; and determining a k-way split of the n data points using $F_k(n)$, the table and a traceback procedure to find one or more endpoints of the split;

and displaying the nodal tree on a monitor or equivalent device for use by the human user or storing the nodal tree on a computer readable medium for use by the human user.

40. An apparatus as in claim 39, wherein each FSA has more than one fast cell.

41. An apparatus as in claim 39, wherein each FSA has more than one fast cell, wherein the number of data objects in the group of data objects that is the root node is n, wherein n is a positive integer number greater than 100.

42. An apparatus as in claim 41, wherein each FSA has more than one reference cell.

43. An apparatus as in claim 42, wherein all of the possible candidate score values are computed for each reference cell and a best score subset is calculated for each reference cell.

44. An apparatus as in claim 43, wherein a best score subset and a horizontal start subset is computed for each reference cell, wherein the best score subset and horizontal start subset computed for each reference cell are the same subset, wherein each best score subset and each horizontal start subset have the same size, and the same size is c scores, wherein c is the closest integer number to $\sqrt{n}$ or wherein $c=c_1$, $c_1$ being a positive integer constant less than n, wherein the data set is real-world data, wherein each FSA uses only one measure of intra-segment homogeneity, wherein the one measure of intra-segment homogeneity is $r(i,j)$, wherein the overall measure of segment homogeneity for each of only some of the possible segmentations of the data set is the sum of all the $r(i,j)$ values for each of the possible segmentations.

45. An apparatus as in claim 44, wherein the real-world data is genetics data, pharmacogenomics data, pharmaceutical high-throughput screening data, or computational chemistry data.

46. An apparatus as in claim 44, wherein each FSA uses only one measure of intra-segment homogeneity, wherein the one measure of intra-segment homogeneity is the sum of squared deviations of data points within a segment about their mean, wherein the data set is real-world data, wherein each fast cell of each FSA has the size of c scores, wherein each fast cell of each FSA also has the horizontal size of c scores, wherein there is a best score for each fast cell, wherein c is sufficiently large that it is likely that the best score for each fast cell is among the c scores computed for each fast cell, wherein c is the closest integer number to $\sqrt{n}$, wherein there are only two cell score election categories: a definite optimal score or a probable optimal score and wherein there is only one overall score election category: a probable overall optimal score value.

47. An apparatus as in claim 46, wherein the real-world data is genetics data, pharmacogenomics data, or pharmaceutical high-throughput screening data.

* * * * *